(12) United States Patent
Kondo et al.

(10) Patent No.: US 6,337,034 B1
(45) Date of Patent: Jan. 8, 2002

(54) VINYLENE COMPOUNDS AND LIQUID-CRYSTAL COMPOSITION

(75) Inventors: Tomoyuki Kondo; Shuichi Matsui; Kazutoshi Miyazawa; Yasuko Sekiguchi; Etsuo Nakagawa, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/125,685

(22) PCT Filed: Feb. 7, 1997

(86) PCT No.: PCT/JP97/00312

§ 371 Date: Aug. 24, 1998

§ 102(e) Date: Aug. 24, 1998

(87) PCT Pub. No.: WO97/30966

PCT Pub. Date: Aug. 28, 1997

(30) Foreign Application Priority Data

Feb. 23, 1996 (JP) .............................................. 8-061935

(51) Int. Cl.[7] .......................... C09K 19/30; C09K 19/20; C09K 19/12; C07C 69/76; C07C 19/08; C07D 319/06

(52) U.S. Cl. ............................ 252/299.63; 252/299.67; 252/299.66; 252/299.61; 560/54; 570/129; 549/369

(58) Field of Search ....................... 252/299.67, 299.63, 252/299.66, 299.61; 560/54; 570/129

(56) References Cited

U.S. PATENT DOCUMENTS

| | | | |
|---|---|---|---|
| 4,642,199 A | 2/1987 | Sugimori et al. | 252/299.61 |
| 5,204,018 A | * 4/1993 | Kelly | 252/299.63 |
| 5,372,745 A | 12/1994 | Yoshinaga et al. | 252/299.01 |

FOREIGN PATENT DOCUMENTS

| | | |
|---|---|---|
| FR | 2404040 | 4/1979 |
| JP | 61-1664 | 1/1986 |
| JP | 62-502966 | 11/1987 |
| JP | 4-279560 | 10/1992 |
| JP | 4-330019 | 11/1992 |
| JP | 5-5905 | 1/1993 |
| JP | 7-72148 | 8/1995 |
| WO | WO86/06372 | 11/1986 |

OTHER PUBLICATIONS

Destrade et al., "Chirality in Polar Mesogens: Reentrant Cholesteric and New Smectic Phases", Mol. Cryst. Liq. Cryst., 1985, vol. 127, 273–282.

Levelut, "X–ray Diffraction by Incommensurate Liquid Crystal", NATO ASI Ser., Ser. B, 1987, vol. 166, 283–296.

Sigaud et al., "Generalization of the polymorphism with 2D fluid smectic phases", J. Physique Lett., 1985, vol. 46, 825–830.

Kelly, "Four unit linking groups IV. Liquid crystals of positive dielectric anisotrophy", Liquid Crystals, 1991, vol. 10, No. 2, 273–287.

Leblanc et al., "Aromatic Copolyesters with Stilbene Mesogenic Groups. 1. Liquid Crystalline Properties of Compounds Containing a Stilbene, Terephthaloyl, or Hydroquinone Central Group", Macromolecules, 1993, vol. 26, No. 17, 4391–4399.

Bonini et al., "New mesogenic compounds with trans–stilbene oxide as the central chiral core", Liquid Crystals, 1993, vol. 13, No. 1, 13–22.

Koden et al., "Liquid Crystallinities of Some Homologous Series Having Bent Linkages –CO–, –O–, –S–, and –CH$_2$–", Mol. Cryst. Liq. Cryst., 1984, vol. 106, 31–44.

Tinh, "Reentrant Behavior and Cyano Substituted Aryl p–Alkoxycinnamates", Mol. Cryst. Liq. Cryst., 1983, vol. 91, 285–294.

Druon et al., "Study of $S_A$ Phase Structure Using Dielectric Relaxation", Mol. Cryst. Liq. Cryst., 1983, vol. 98, 201–208.

* cited by examiner

*Primary Examiner*—Shean C. Wu
(74) *Attorney, Agent, or Firm*—Wenderoth, Lind & Ponack, L.L.P.

(57) ABSTRACT

Liquid crystalline compounds which have a wide temperature range of liquid crystal phase, low viscosity, and improved threshold voltage; liquid crystal compositions; and liquid crystal display devices comprising the composition can be provided; and the liquid crystalline compounds are expressed by the general formula (1)

$$Ra—A_1—Z_1—A_2—Z_2—A_3—(Z_3—A_4)_m—Rb \qquad (1)$$

wherein Ra represents an alkyl group having 1 to 20 carbon atoms one or more —CH$_2$— in which alkyl group may be replaced by —O— or the like, and one or more hydrogen atoms in which alkyl group may be replaced by a halogen atom; Rb represents Ra, a halogen atom, or cyano group; $A_1$, $A_2$, $A_3$, and $A_4$ independently represent a divalent ring group; $Z_1$, $Z_2$, and $Z_3$ independently represent an alkenylene group having 2 to 4 carbon atoms, —COO—, a covalent bond, or the like provided that at least one of $Z_1$ to $Z_3$ represents an alkenylene group having 2 to 4 carbon atoms, and at least one of $Z_1$ to $Z_3$ represents —COO— or —OCO—; and m is 0 or 1.

19 Claims, No Drawings

VINYLENE COMPOUNDS AND LIQUID-CRYSTAL COMPOSITION

TECHNICAL FIELD

The present invention relates to a liquid crystalline compound and liquid crystal composition. More specifically, it relates to a novel liquid crystalline compound which has an alkenylene group having 2 to 4 carbon atoms and ester bond as bonding group at the same time, relates to a liquid crystal composition comprising the compound, and relates to a liquid crystal display device comprising the liquid crystal composition.

BACKGROUND ART

Liquid crystal display devices comprising liquid crystalline compounds (the term "liquid crystalline compound" as used hereinafter is intended to use as a general name for compounds exhibiting a liquid crystal phase, or compounds which do not exhibit a liquid crystal phase but are useful as a component of liquid crystal compositions) are widely used in displays such as watches, tabletop calculators, and word processors. These display devices utilize optical anisotropy and dielectric anisotropy of liquid crystalline compounds.

Liquid crystal phase includes nematic liquid crystal phase, smectic liquid crystal phase, and cholesteric liquid crystal phase, and display devices utilizing nematic liquid crystal phase are most widely used.

As display mode using a liquid crystal, there have been devised dynamic scattering (DS) mode, deformation of aligned phases (DAP) mode, guest/host (GH) mode, twisted nematic (TN) mode, super twisted nematic (STN) mode, and thin film transistor (TFT) mode.

Liquid crystalline compounds used in these display devices have to exhibit liquid crystal phase in a wide temperature range with room temperature being its center, have to be sufficiently stable under conditions in which the display devices are used, and have to have properties sufficient to drive the display devices. However, no liquid crystalline compounds which satisfy these requirements by a single compound have been found up to now. Accordingly, it is actual circumstances that several kind or several tens kind of liquid crystalline compounds are mixed to produce liquid crystal compositions having required properties. These liquid crystal compositions are required to be stable against moisture, light, heat, and air which usually present under conditions in which the display devices are used, required to be stable against electric field and electromagnetic radiation, and further required to be chemically stable against the compounds to be mixed. The liquid crystal compositions are required to have proper values of such physical properties as optical anisotropy ($\Delta n$) and dielectric anisotropy ($\Delta\epsilon$) depending on display mode and the shape of display devices. Further, it is important that each component in the liquid crystal compositions has an excellent solubility with one another.

Especially, it is desired to still more lower threshold voltage which largely contributes to high speed response necessary for expanding the size of screen of liquid crystal display, and contributes to saving of electric power (E. Jakeman et al., Phys. Lett., 39A. 69 (1972)). For the high speed response, low viscosity of the compositions is also important. Moreover, environments in which liquid crystal display devices are used are diversified in recent years, and keeping with such circumstance, development of liquid crystalline compounds which exhibit liquid crystal phase in a wider temperature range is earnestly desired.

In order to achieve these purposes, various compounds have heretofore been developed, for instance, the compound expressed by the following formula (a) or (b) is proposed in Laid-open Japanese Patent Publication No. Hei 4-279560, and the compound expressed by the following formula (c) is proposed in Japanese Patent Publication No. Hei 7-72148, respectively.

However, the compound expressed by the formula (a) can not be said to be sufficiently wide in temperature range of liquid crystal phase, and the compound expressed by the formula (b) has a problem that its viscosity is high.

Whereas the compound expressed by the formula (c) is a three ring compound containing an alkenylene group as bonding group, its disclosure is insufficient. That is, the physical properties of the compound are not shown, and besides, specific data are not disclosed at all about the utility expected when it is used as a component of liquid crystal compositions.

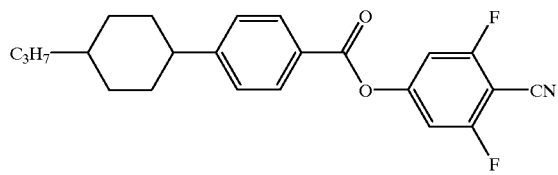

(a)

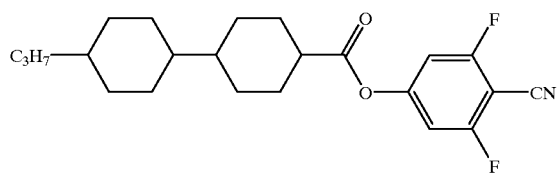

(b)

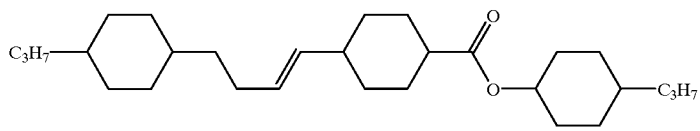

(c)

DISCLOSURE OF THE INVENTION

An object of the present invention is to remove the problems in the background art described above. Another object of the present invention is to provide novel liquid crystalline compounds which are wide in temperature range of liquid crystal phase, are low in viscosity, have a low threshold voltage, and are excellent in stability and mutual solubility with other liquid crystal materials, to provide liquid crystal compositions comprising the liquid crystalline compound, and to provide liquid crystal display devices comprising the liquid crystal composition.

The present invention for achieving the purposes described above is summarized as follows:

(1) A vinylene compound expressed by the general formula (1)

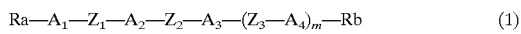

wherein Ra represents an alkyl group having 1 to 20 carbon atoms one or more —$CH_2$— in which alkyl group may be replaced by —O—, —S—, —CO—, —CH=CH—, or —C≡C—, but in no case —O— and/or —S— continues, and one or more hydrogen atoms in which alkyl group may be replaced by a halogen atom; Rb represents Ra, a halogen atom, or cyano group; $A_1$, $A_2$, $A_3$, and $A_4$ independently represent trans-1,4-cyclohexylene group, cyclohexenylene group, 1,4-phenylene group one or more hydrogen atoms on which ring may be replaced by a halogen atom or cyano group, pyridine-2,5-diyl group, pyrimidine-2,5-diyl group, or 1,3-dioxane-2,5-diyl group; $Z_1$, $Z_2$, and $Z_3$ independently represent an alkenylene group having 2 to 4 carbon atoms, —COO—, —OCO—, —$(CH_2)_2$—, —C≡C—, —$CH_2$O—, —O$CH_2$—, or a covalent bond provided that at least one of $Z_1$ to $Z_3$ represents an alkenylene group having 2 to 4 carbon atoms, and at least one of $Z_1$ to $Z_3$ represents —COO— or —OCO—; and m is 0 or 1.

(2) The vinylene compound recited in (1) above wherein m is 0.

(3) The vinylene compound recited in (1) above wherein m is 1.

(4) The vinylene compound recited in (2) above wherein either $Z_1$ or $Z_2$ is vinylene or butenylene.

(5) The vinylene compound recited in (3) above wherein either $Z_1$ or $Z_2$ is vinylene or butenylene.

(6) The vinylene compound recited in (4) above wherein $A_1$ and $A_2$ are independently trans-1,4-cyclohexylene group, or 1,4-phenylene group one or more hydrogen atoms on which ring may be replaced by a halogen atom or cyano group.

(7) The vinylene compound recited in (5) above wherein $A_1$ and $A_2$ are independently trans-1,4-cyclohexylene group, or 1,4-phenylene group one or more hydrogen atoms on which ring may be replaced by a halogen atom or cyano group.

(8) A liquid crystal composition comprising at least one vinylene compound recited in any one of (1) to (7) above.

(9) A liquid crystal composition comprising, as a first component, at least one vinylene compound recited in any one of (1) to (7) above, and comprising, as a second component, at least one compound selected from the group consisting of the compounds expressed by any one of the general formulas (2), (3), and (4)

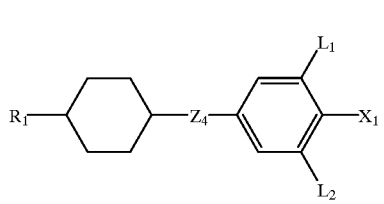

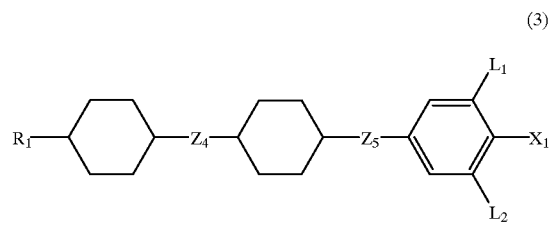

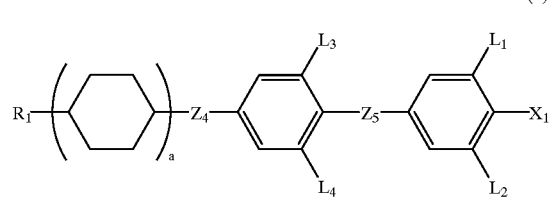

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent —$(CH_2)_2$—, —CH=CH—, or a covalent bond; and a is 1 or 2.

(10) A liquid crystal composition comprising, as a first component, at least one vinylene compound recited in any one of (1) to (7) above, and comprising, as a second component, at least one compound selected from the group consisting of the compounds expressed by any one of the general formulas (5), (6), (7), (8), and (9)

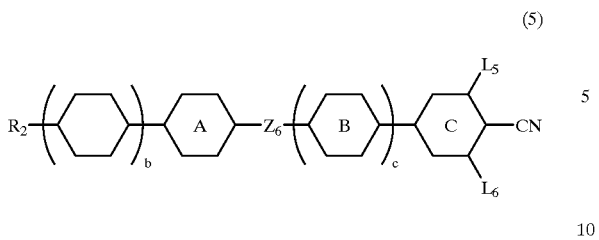

(5)

wherein $R_2$ represents F, an alkyl group having 1 to 10 carbon atoms, or an alkenyl group having 2 to 10 carbon atoms any methylene group (—$CH_2$—) in which alkyl or alkenyl group may be replaced by oxygen atom (—O—), but in no case two or more methylene groups are continuously replaced by oxygen atom; ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —($CH_2$)$_2$—, —COO—, or a covalent bond; $L_5$ and $L_6$ independently represent H or F; and b and c are independently 0 or 1,

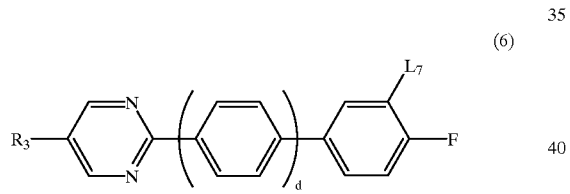

(6)

wherein $R_3$ represents an alkyl group having 1 to 10 carbon atoms, $L_7$ represents H or F; and d is 0 or 1,

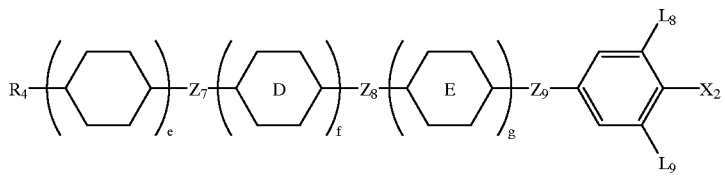

(7)

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or a covalent bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$; and e, f, and g are independently 0 or 1,

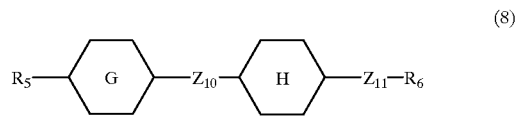

(8)

wherein $R_5$ and $R_6$ independently represent an alkyl group having 1 to 10 carbon atoms or an alkenyl group having 2 to 10 carbon atoms any methylene group (—$CH_2$—) in which alkyl or alkenyl group may be replaced by oxygen atom (—O—), but in no case two or more methylene groups are continuously replaced by oxygen atom; ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents —C≡C—COO—, —($CH_2$)$_2$—, —CH=CH—C≡C—or a covalent bond; and $Z_{11}$ represents —COO— or a covalent bond,

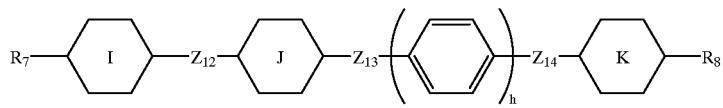

(9)

wherein $R_7$ and $R_8$ independently represent an alkyl group having 1 to 10 carbon atoms or an alkenyl group having 2 to 10 carbon atoms any methylene group (—$CH_2$—) in which alkyl or alkenyl group may be replaced by oxygen atom (—O—), but in no case two or more methylene group are continuously replaced by oxygen atom; ring I represents trans-1,4-cyclohexylene group, 1,4-phenylene group, or pyrimidine-2,5-diyl group; ring J represents trans-1,4-cyclohexylene group, 1,4-phenylene group one or more hydrogen atoms on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —($CH_2$)$_2$—, or a covalent bond; $Z_{13}$ represents —CH=CH—, —C≡C—, —COO—, or a covalent bond; and h is 0 or 1.

(11) A liquid crystal composition comprising, as a first component, at least one vinylene compound recited in any one of (1) to (7) above, comprising, as a part of a second component, at least one compound selected from the group consisting of the compounds expressed by any one of the general formulas (2), (3), and (4), and comprising, as another part of the second component, at least one compound selected from the group consisting of the compounds expressed by any one of the general formulas (5), (6), (7), (8), and (9).

(12) A liquid crystal display device comprising the liquid crystal composition recited in any one of (8) to (11) above.

Liquid crystalline vinylene compounds of the present invention expressed by the general formula (1) are wide in temperature range of liquid crystal phase, are low in viscosity, and have a low threshold voltage. These liquid crystalline compounds are sufficiently stable chemically and physically under the conditions in which liquid crystal display devices are ordinarily used. Further, liquid crystalline compounds having desired physical properties can be obtained by selecting proper rings, substituents and/or bonding groups from molecule forming elements.

Accordingly, when the compounds of the present invention are used as component of liquid crystal compositions, novel liquid crystal compositions having preferable properties can be provided.

Liquid crystalline compounds of the present invention expressed by the general formula (1) are classified as shown below. In the formulas shown below, ak represents an alkenylene group having 2 to 4 carbon atoms, E represents ester bond, and Ra, Rb, $A_1$ to $A_4$, and $Z_1$ to $Z_3$ have the same meaning as defined above.

Compounds having three six-membered rings:

Ra—$A_1$—ak—$A_2$—E—$A_3$—Rb (1a)

Ra—$A_1$—E—$A_2$—ak—$A_3$—Rb (1b)

Compounds having four six-membered rings:

Ra—$A_1$—$A_2$—ak—$A_3$—E—$A_4$—Rb (1c)

Ra—$A_1$—$A_2$—E—$A_3$—ak—$A_4$—Rb (1d)

Ra—$A_1$—ak—$A_2$—$A_3$—E—$A_4$—Rb (1e)

Ra—$A_1$—E—$A_2$—$A_3$—ak—$A_4$—Rb (1f)

Ra—$A_1$—ak—$A_2$—E—$A_3$—$A_4$—Rb (1g)

Ra—$A_1$—E—$A_2$—ak—$A_3$—$A_4$—Rb (1h)

Ra—$A_1$—ak—$A_2$—ak—$A_3$—E—$A_4$—Rb (1i)

Ra—$A_1$—E—$A_2$—ak—$A_3$—ak—$A_4$—Rb (1j)

Ra—$A_1$—(CH$_2$)$_2$—$A_2$—ak—$A_3$—E—$A_4$—Rb (1k)

Ra—$A_1$—ak—$A_2$—(CH$_2$)$_2$—$A_2$—E—$A_4$—Rb (1l)

Ra—$A_1$—ak—$A_2$—E—$A_3$—(CH$_2$)$_2$—$A_4$—Rb (1m)

Ra—$A_1$—E—$A_2$—ak—$A_3$—(CH$_2$)$_2$—$A_4$—Rb (1n)

Ra—$A_1$—C≡C—$A_2$—ak—$A_3$—E—$A_4$—Rb (1o)

Ra—$A_1$—ak—$A_2$—C≡C—$A_3$—E—$A_4$—Rb (1p)

Ra—$A_1$—ak—$A_2$—E—$A_3$—C≡C—$A_4$—Rb (1q)

Ra—$A_1$—CH$_2$O—$A_2$—ak—$A_3$—E—$A_4$—Rb (1r)

Ra—$A_1$—ak—$A_2$—CH$_2$O—$A_3$—E—$A_4$—Rb (1s)

Ra—$A_1$—ak—$A_2$—E—$A_3$—CH$_2$O—$A_4$—Rb (1t)

Ra—$A_1$—OCH$_2$—$A_2$—ak—$A_3$—E—$A_4$—Rb (1u)

Ra—$A_1$—ak—$A_2$—OCH$_2$—$A_3$—E—$A_4$—Rb (1v)

Ra—$A_1$—ak—$A_2$—E—$A_3$—OCH$_2$—$A_4$—Rb (1w)

While the compounds expressed by one of the formulas (1a) to (1w) are preferable, the compounds expressed by one of the following formulas (1Xa) to (1Xq) are especially preferable among the former compounds:

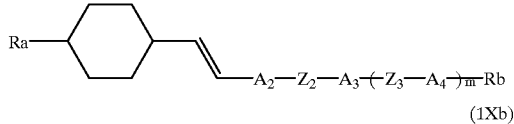

(1Xa)

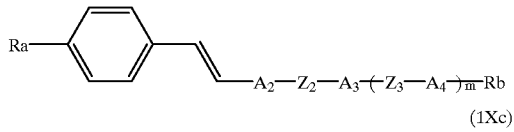

(1Xb)

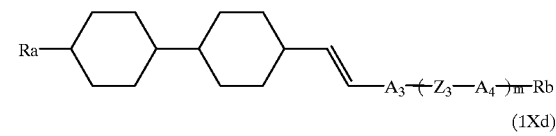

(1Xc)

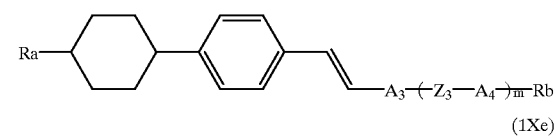

(1Xd)

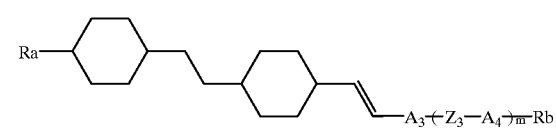

(1Xe)

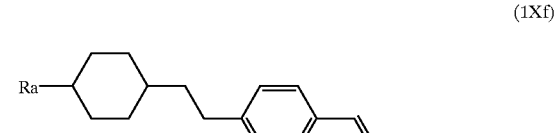

(1Xf)

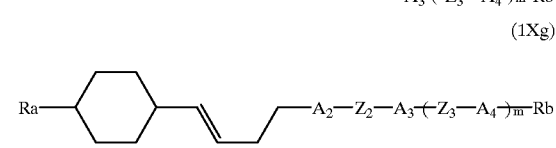

(1Xg)

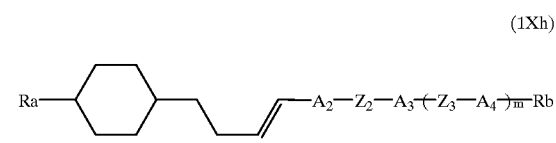

(1Xh)

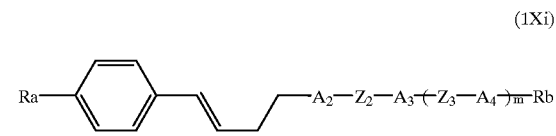

(1Xi)

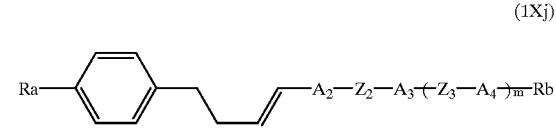

(1Xj)

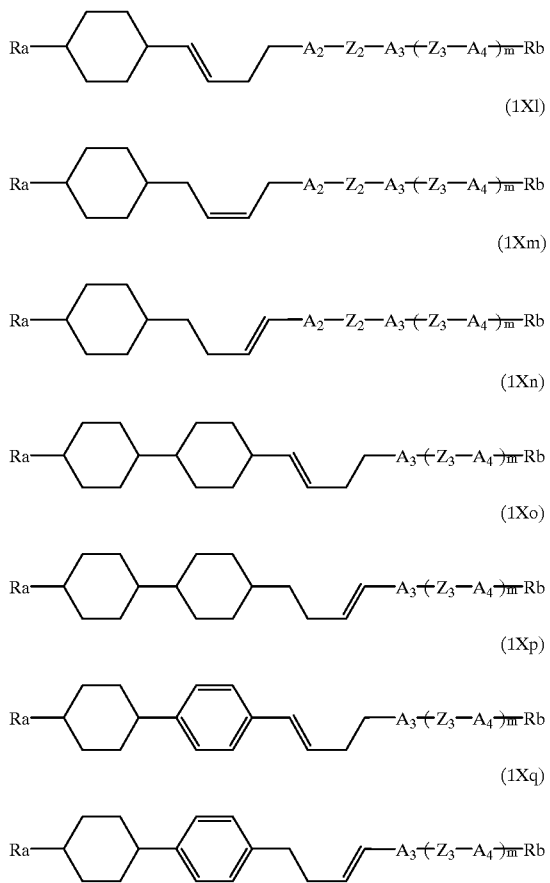

wherein Ra, Rb, $A_2$ to $A_4$, $Z_2$, $Z_3$, and m have the same meaning as described above.

As described above, the liquid crystalline compounds of the present invention are expressed by the general formula (1).

In the formula, Ra is a straight chain or branched alkyl group having 1 to 20 carbon atoms. As the straight chain alkyl group, methyl, ethyl, propyl, butyl, pentyl, hexyl, heptyl, decyl, pentadecyl, and icosyl can specifically be mentioned. As the branched alkyl group, isopropyl, 2-methylbutyl, sec-butyl, tert-butyl, isopentyl, isohexyl, 3-ethyloctyl, 3,8-dimethyltetradecyl, and 5-ethyl-5-methylnonadecyl can specifically be mentioned. The branched alkyl groups described above may be ones which exhibit an optical activity.

One or more —$CH_2$— in these alkyl groups may be replaced by —O—, —S—, —CO—, —CH=CH—, or —C≡C—, unless —O— and/or —S— continues. Among the alkyl groups, alkoxy groups and alkoxyalkyl groups can be mentioned as examples in which —$CH_2$— is replaced by —O—; alkylthioalkyl groups as examples in which —$CH_2$— is replaced by —S—; alkenyl groups, alkoxyalkenyl groups, alkenyloxy groups, alkenyloxyalkyl groups, and alkadienyl groups as examples in which —$CH_2$— is replaced by —CH=CH—; and alkynyl groups, alkynyloxy groups, and alkoxyalkynyl groups as examples in which —$CH_2$— is replaced by —C≡C—. One or more hydrogen atoms in the alkyl groups described above may be replaced by a halogen atom, and halogen substituted alkyl groups, halogen substituted alkoxy groups, halogen substituted alk-enyl groups, and halogen substituted alkynyl groups can be mentioned as their examples.

Specific examples of these substituted alkyl groups are as follows:

As alkoxy groups, such groups as methoxy, ethoxy, propoxy, butoxy, pentyloxy, and nonyloxy, as alkoxyalkyl groups, such groups as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl, and octyloxymethyl, as alkylthioalkyl groups, such groups as methylthiomethyl, methylthioethyl, methylthiopropyl, methylthiobutyl, methylthiooctyl, ethylthiomethyl, ethylthioethyl, ethylthioheptyl, propylthiomethyl, propylthioethyl, propylthiopropyl, propylthiopentyl, hexylthiomethyl, and heptylthioethyl, as the groups in which —CO— substituted, such groups as methylcarbonyl, ethylcarbonyl, propylcarbonyl, methoxycarbonyl, ethoxycarbonyl, propoxycarbonyl, butoxycarbonyl, heptyloxycarbonyl, 2-oxopropyl, 2-oxobutyl, 3-oxobutyl, 2-oxopentyl, 4-oxopentyl, 3-oxohexyl, 5-oxohexyl, 2-oxoheptyl, 3-oxoheptyl, 6-oxoheptyl, 2-oxooctyl, 4-oxooctyl, 7-oxooctyl, 3-oxononyl, 6-oxononyl, 8-oxononyl, 2-oxodecyl, 5-oxodecyl, and 9-oxodecyl, as alkenyl groups, such groups as vinyl, propenyl, butenyl, pentenyl, hexenyl, and decenyl, as alkoxyalkenyl groups, such groups as methoxypropenyl, ethoxypropenyl, pentyloxypropenyl, methoxybutenyl, ethoxybutenyl, pentyloxybutenyl, methoxypentenyl, propoxypentenyl, methoxyhexenyl, propoxyhexenyl, methoxyheptenyl, and methoxyoctenyl, as alkenyloxy groups, such groups as propenyloxy, butenyloxy, pentenyloxy, octenyloxy, and propenyloxymethyl, as alkenyloxyalkyl groups, such groups as propenyloxyethyl, propenyloxybutyl, butenyloxymethyl, butenyloxyethyl, butenyloxypentyl, pentenyloxymethyl, pentenyloxypropyl, hexenyloxymethyl, hexenyloxyethyl, heptenyloxymethyl, and octenyloxymethyl, as alkadienyl groups, such groups as butadienyl, pentadienyl, hexadienyl, heptadienyl, octadienyl, and icosadienyl, as alkynyl groups, such groups as ethynyl, propynyl, butynyl, pentynyl, and octynyl, as alkynyloxy groups, such groups as ethynyloxy, propynyloxy, butynyloxy, pentynyloxy, and tetradecynyloxy, as alkoxyalkynyl groups, methoxypropynyl, methoxypentynyl, ethoxybutynyl, propoxypropynyl, hexyloxyheptynyl, methoxymethylbutynyl, methoxypropylethynyl, and butoxymethylpropynyl, as halogen substituted alkyl groups, such groups as fluoromethyl, difluoromethyl, trifluoromethyl, 2-fluoroethyl, 1,2-difluoroethyl, 1,1,2,2-tetrafluoroethyl, 2-bromo-1,2-difluoroethyl, 3-fluoropropyl, 1,2,3,3-tetrafluoropropyl, 1,1,2,3,3,3-hexafluoropropyl, 4-fluorobutyl, 1,1,2,4- tetrafluorobutyl, 5-fluoropentyl, 2,3,3,4,5-pentafluoropentyl, 6-fluorohexyl, 2,3,4,6-tetrafluorohexyl, 7-fluoroheptyl, and 8,8-difluorooctyl, as halogen substituted alkoxy groups, such groups as difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 1,1,2,3,3,3-hexafluoropropoxy, and perfluoropropoxy, and as halogen substituted alkenyl groups, such groups as 3-fluoropropenyl, 4-fluoro-1-butenyl, 4-fluoro-2-butenyl, 5-fluoro-1-pentenyl, 5-fluoro-2-pentenyl, 5-fluoro-3-pentenyl, 6-fluoro-1-hexenyl, 6-fluoro-3-hexenyl, 7-fluoro-5-heptenyl, 2,2-difluorovinyl, 1,2-difluorovinyl, 2-chloro-2-fluorovinyl, 2-bromo-2-fluorovinyl, 2-fluoro-2-cyanovinyl, 3,3-difluoro-2-propenyl, 3-chloro-3-fluoro-1-propenyl, 2,3-difluoro-1-propenyl, 1,3-difluoro-2-propenyl, 1,3,3-trifluoro-2-propenyl, 1,2,4,4-tetrafluoro-3-butenyl, 5,5-difluoro-4-pentenyl, 3,3-difluoro-5-hexenyl, and 8,8-difluoro-7-octenyl.

While Rb is a group selected from the Ra described above, a member selected from halogen atoms including F, Cl, Br, and I, or cyano group, it is preferably F, Cl, or cyano group from the viewpoint, for example, of stability.

$A_1$, $A_2$, $A_3$, and $A_4$ are independently selected from trans-1,4-cyclohexylene group, cyclohexenylene group, 1,4-phenylene group one or more hydrogen atoms on which ring may be replaced by a halogen atom or cyano group, pyridine-2,5-diyl group, pyrimidine-2,5-diyl group, or 1,3-dioxane-2,5-diyl group.

Among the groups in which one or more hydrogen atoms may be replaced by a halogen atom or cyano group, for example, 2-fluoro-1,4-phenylene, 3-fluoro-1,4-phenylene, 2,3-difluoro-1,4-phenylene, 3,5-difluoro-1,4-phenylene, 2,3-5-trifluoro-1,4-phenylene, 2-chloro-1,4-phenylene, 3-chloro-1,4-phenylene, 2,3-dichloro-1,4-phenylene, 3,5-dichloro-1,4-phenylene, 3-bromo-1,4-phenylene, 2-iodo-1,4-phenylene, 2-chloro-3-fluoro-1,4-phenylene, 3-fluoro-5-chloro-1,4-phenylene, 2-cyano-1,4-phenylene, 3-cyano-1,4-phenylene, and 2,3-dicyano-1,4-phenylene can be mentioned as examples in which the ring is 1,4-phenylene.

At least one of $Z_1$, $Z_2$, and $Z_3$ is an alkenylene group having 2 to 4 carbon atoms, vinylene or butenylene can be mentioned as their preferable examples, and the vinylene or butenylene in which alkenylene group is in trans form can be mentioned as more preferable examples.

Compounds of the present invention expressed by the general formula (1) and constituted by the groups selected from the Ra, Rb, $A_1$ to $A_4$, and $Z_1$ to $Z_3$ described above have preferable properties. Among them, the compounds which do not have two or more rings containing a hetero atom, and are expressed by one of the formulas (1Xa) to (1Xq) are more preferable.

As more specific examples of these compounds, the ones expressed by one of the following formulas (1-1) to (1-47) can be mentioned:

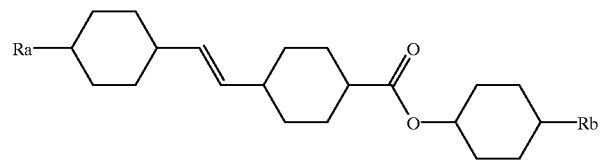

(1-1)

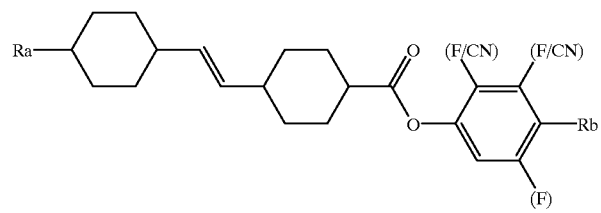

(1-2)

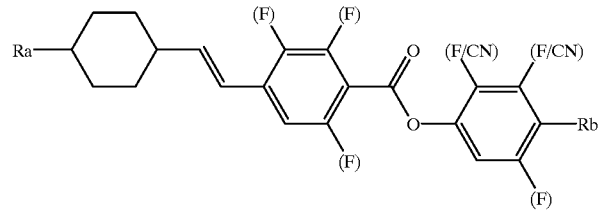

(1-3)

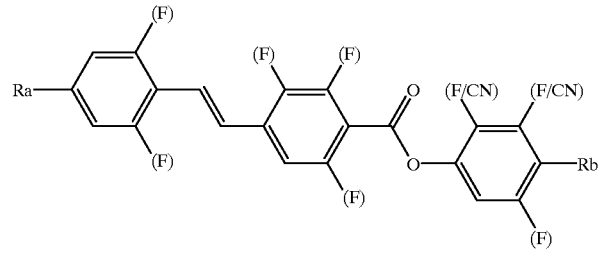

(1-4)

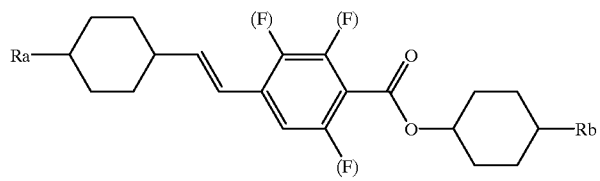
(1-5)
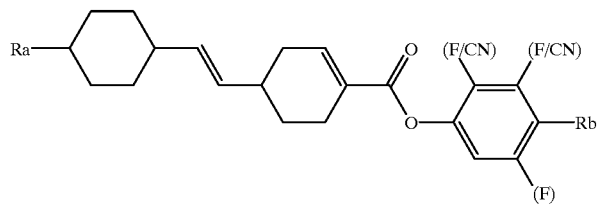
(1-6)
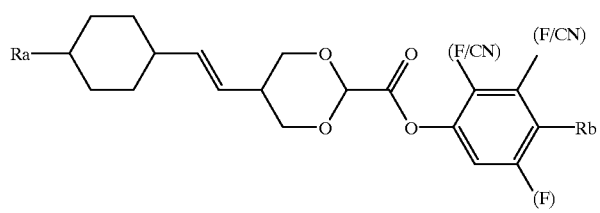
(1-7)
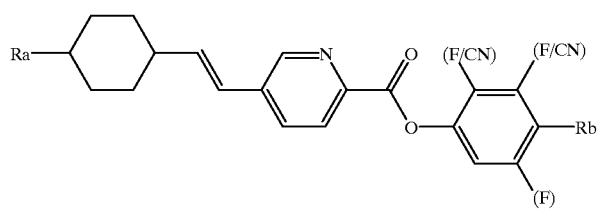
(1-8)
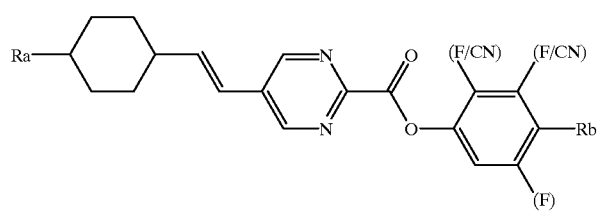
(1-9)
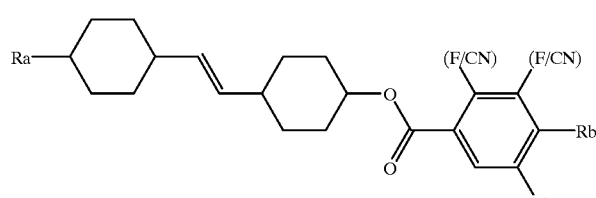
(1-10)
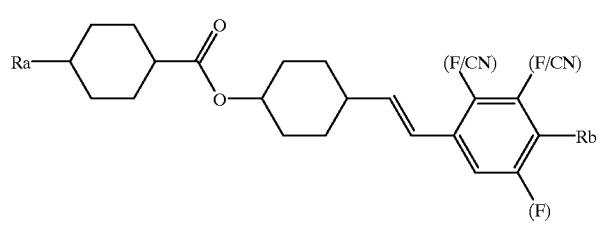
(1-11)

(1-12)
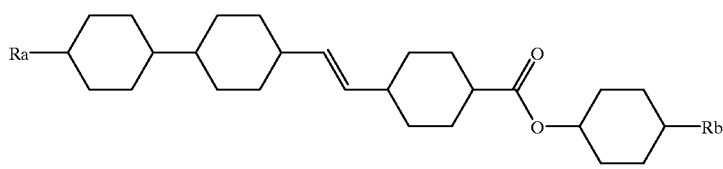
(1-13)
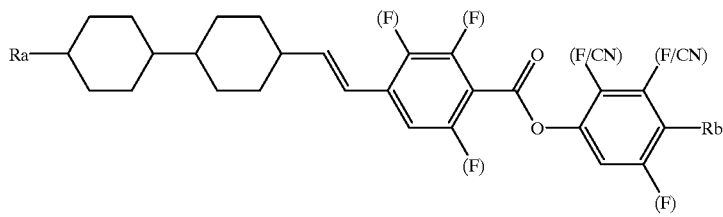
(1-14)
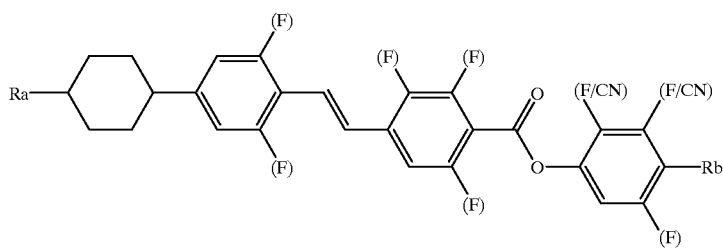
(1-15)
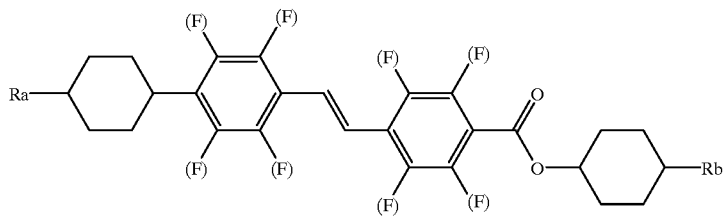
(1-16)
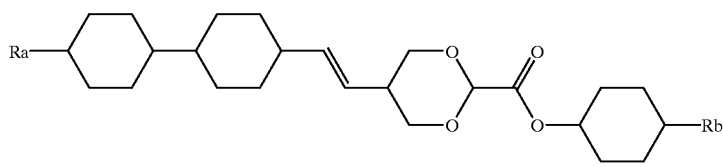
(1-17)
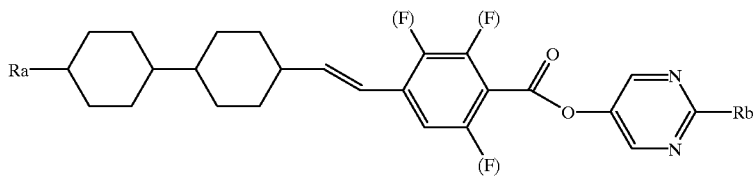
(1-18)
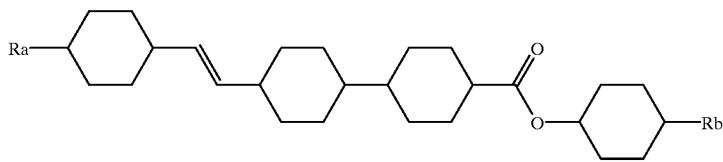

-continued
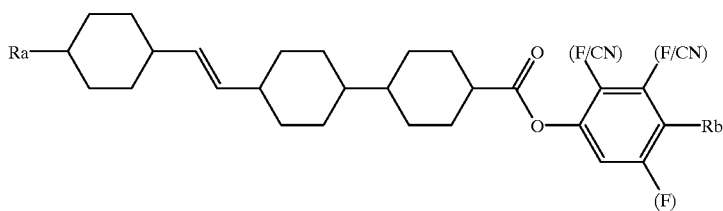
(1-19)
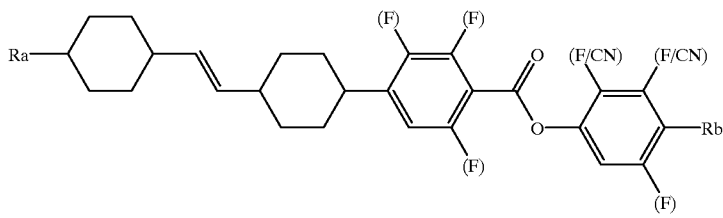
(1-20)
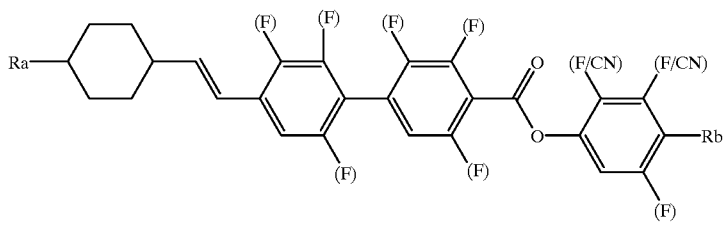
(1-21)
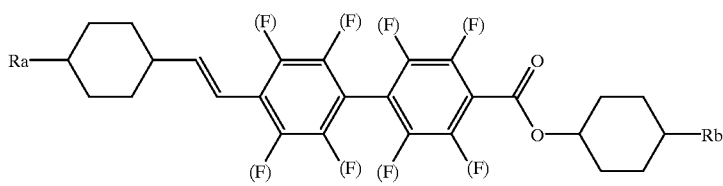
(1-22)
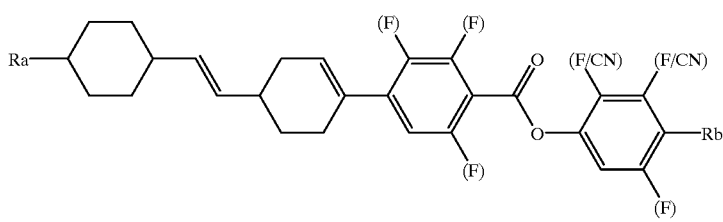
(1-23)
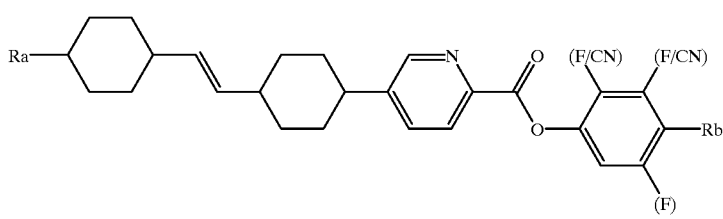
(1-24)
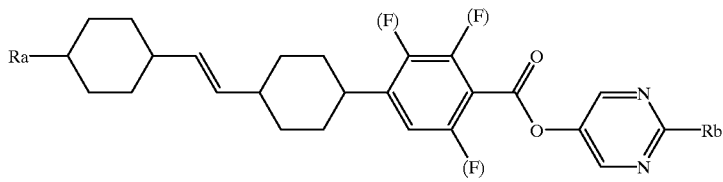
(1-25)

(1-26)
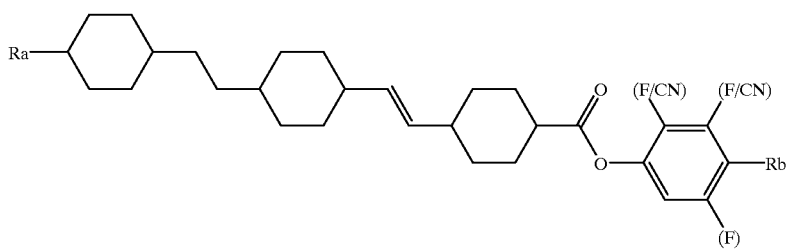
(1-27)
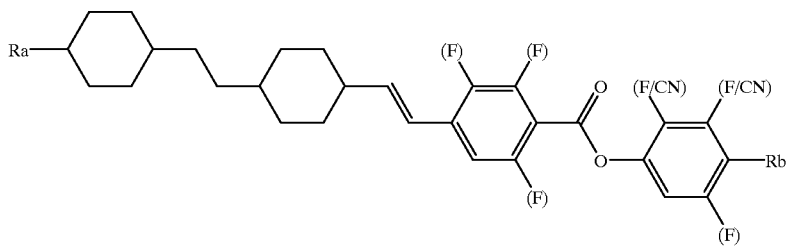
(1-28)
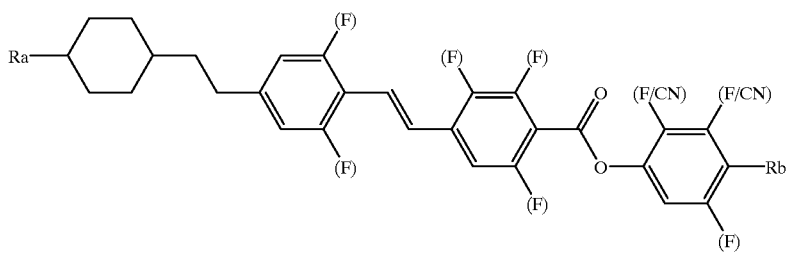
(1-29)
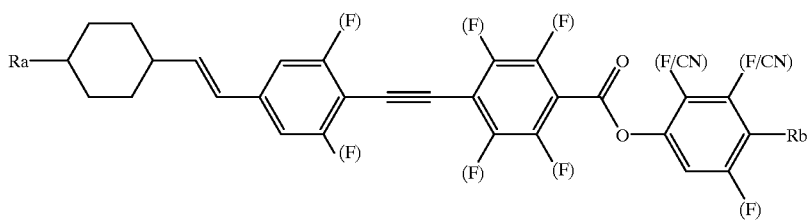
(1-30)
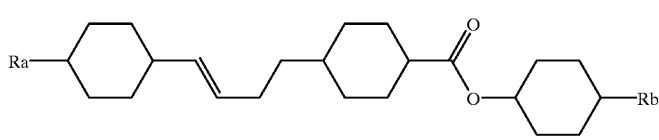
(1-31)
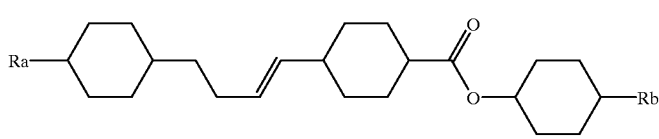
(1-32)
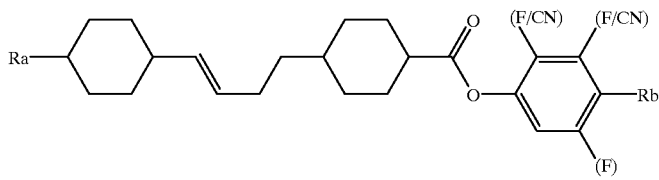

-continued
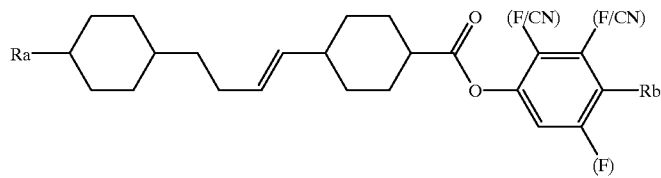
(1-33)
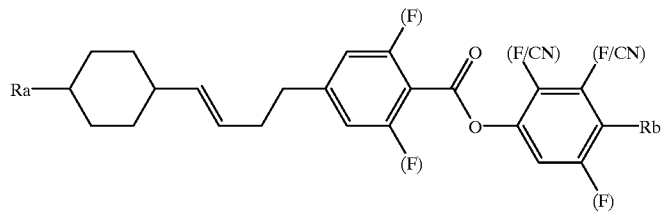
(1-34)
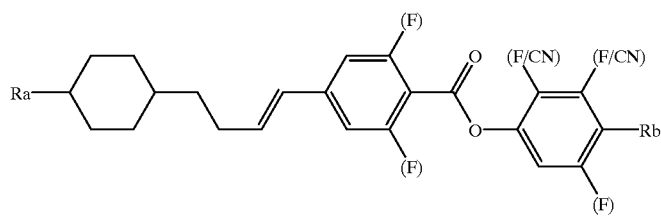
(1-35)
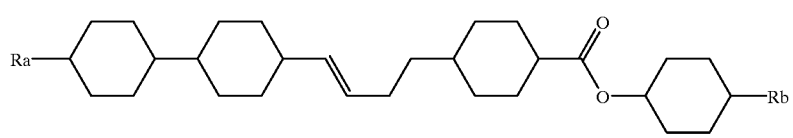
(1-36)
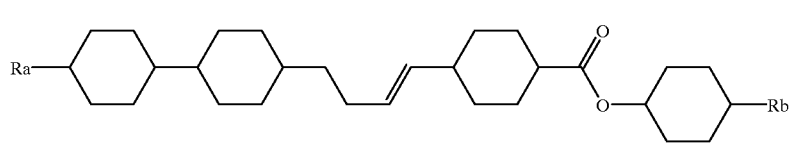
(1-37)
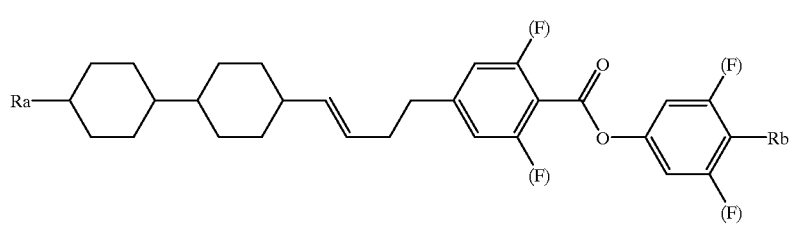
(1-38)
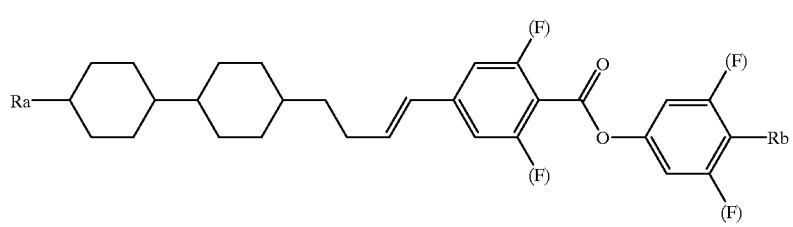
(1-39)
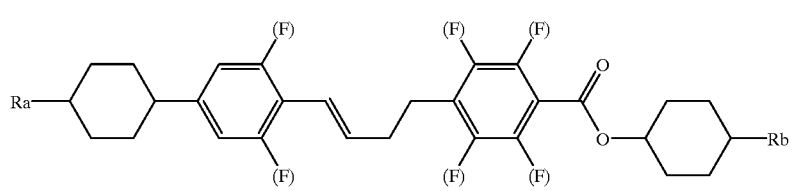
(1-40)

(1-41)
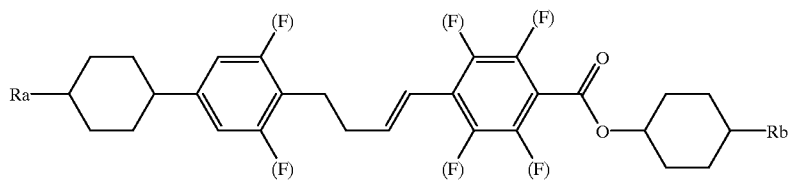
(1-42)
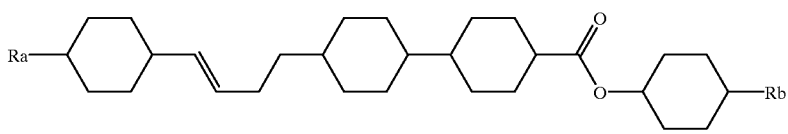
(1-43)
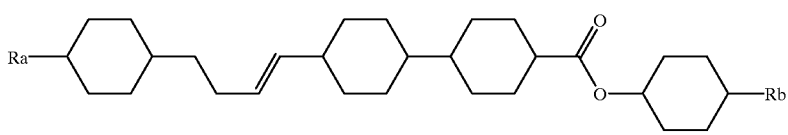
(1-44)
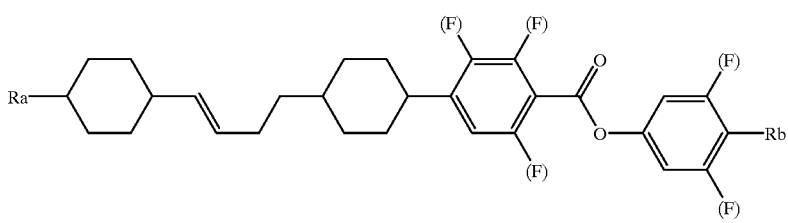
(1-45)
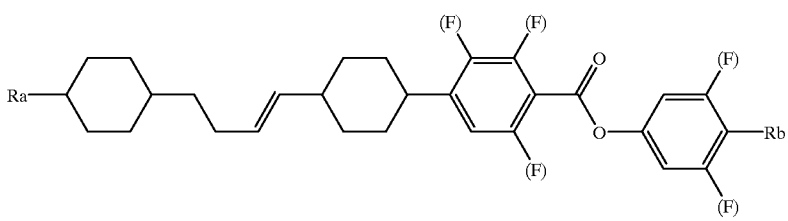
(1-46)
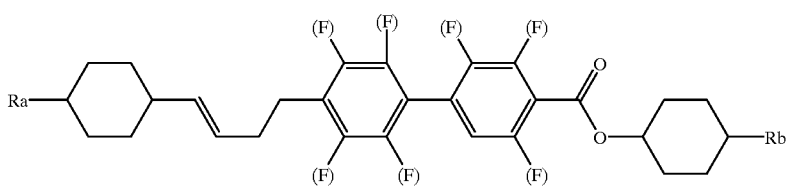
(1-47)
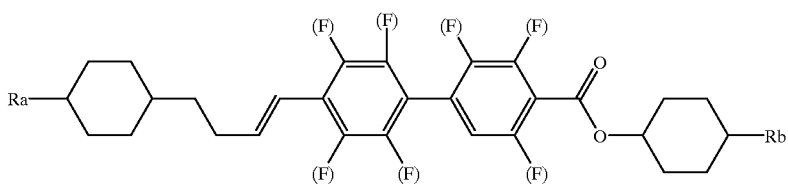

wherein Ra and Rb have the same meaning as described above, and hydrogen atom on the ring may independently be replaced by the atom or group shown in the parenthesis.

Compounds of the present invention expressed by the general formula (1) can easily be produced by known general methods of organic synthesis, for instance, by the following methods:

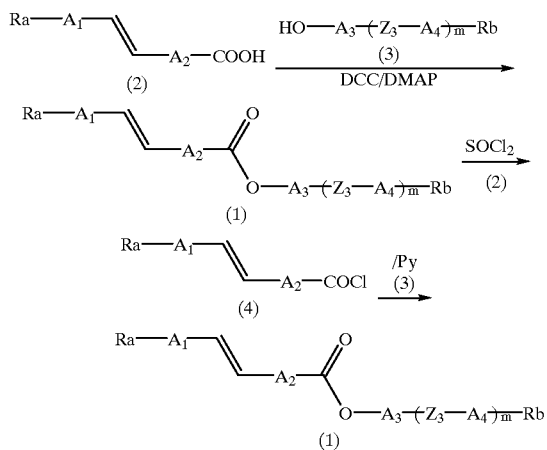

wherein Ra, Rb, $A_1$ to $A_4$, $Z_3$, and m have the same meaning as described above.

For instance, a compound (1) which is an example of the compounds of the present invention can be produced by reacting a carboxylic acid derivative (2) with an alcohol (including phenol) derivative (3) in a solvent such as dichloromethane and chloroform in the presence of a dehydrating agent such as dicyclohexylcarbodiimide (DCC) and 4-dimethylaminopyridine (DMAP) (B. Neises et al., Organic Synthesis, 63, 183 (1985)).

The compound (1) can also be produced by the method of E. J. Corey et al. (The Journal of Organic Chemistry, 38, 3223 (1973)), that is, by converting the carboxylic acid derivative (2) described above into a compound (4) with a halogenating agent such as thionyl chloride in the presence or absence of a solvent such as toluene and benzene, and then reacting the compound (4) with the alcohol derivative (3) described above. This reaction is carried out at a temperature from room temperature to the boiling point of the solvent and under an inert gas atmosphere, more preferably, for accelerating the reaction, in the presence of a base such as pyridine, triethylamine (B. Iselin et al., Helvetica Chimica Acta, 40, 373 (1957)), dimethylaniline (C. Raha, Organic Synthesis, IV, 263 (1963)), or tetramethylurea (M. S. Newman et al., Tetrahedron Letters, 3267 (1967)).

Introduction of carbonyloxy group to the carboxylic acid derivative (2) used as a starting material in the reaction described above can be performed by known general procedures of organic synthesis or their combination. For instance, it can readily be carried out by such methods as the hydrolysis of a nitrile derivative (R. C. Fuson et al., Organic Synthesis, III, 557 (1955); and P. C. Baraldi et al., The Journal of Organic Chemistry, 50, 23 (1985)), the reaction of a Grignard reagent or lithium compound with carbon dioxide (H. Gilman et al., Organic Synthesis, I, 361 (1941); and Y. Fukuyama et al., Synthesis, 443 (1974)), the hydrolysis of an acid halide (N. O. V. Sonntag, Chemical Review, 52, 237 (1953)), or the oxidation of an alkyl, alcohol, or aldehyde derivative (L. Friedman, Organic Synthesis, V, 810 (1973); E. Turos et al., Journal of the American Chemical Society, 111, 8231 (1989); R. L. Shriner et al., Organic Synthesis, II, 538 (1943); D. Vakentine, Jr. et al., The Journal of Organic Chemistry, 45, 3698 (1980); E. Dalcanale et al., The Journal of Organic Chemistry, 51, 567 (1986); and E. J. Corey et al., Tetrahedron Letters, 399 (1979).

Introduction of —CH═CH— can readily be carried out, for instance, by the Wittig reaction (Organic Reactions, Vol. 14, Chapter 3), the Wittig-Schlosser reaction (M. Schlosser et al., Angew. Chem., International Edition in English, 5, 126 (1966), or the Wittig-Horner reaction (J. I. G. Cadogan, Organophosphorus Reagents in Organic Synthesis, Academic (1979)).

That is, compounds in which —CH═CH— is introduced can be produced by reacting an aldehyde with a phosphonium salt in a solvent such as tetrahydrofuran and diethyl ether in the presence of a base such as potassium-tert-butoxide (t-BuOK) and n-butyl lithium. This reaction is preferably carried out at a temperature from room temperature to −50° C. under an inert gas atmosphere. It is possible to isomerize the compounds thus obtained by reacting them with benzenesulfinic acid or p-toluenesulfinic acid.

Further, —CH═CH— can be introduced by a method in which a vinyl Grignard reagent and a halide are subjected to a coupling reaction in the presence of a catalyst such as $Pd(PPh_3)_4$, $PdCl_2(PPh_3)_2$, or $NiCl_2(dppp)$ (T. V. Lee et al., Tetrahedron Letters, 46, 921 (1990)), or a method in which an aldehyde and a Grignard reagent are reacted, and the product thus formed is heated to dehydrate in a solvent such as toluene and xylene in the presence of an acidic catalyst such as p-toluenesulfonic acid.

Introduction of —C≡C— can be carried out, for instance, by the method of W. Tao et al. (The Journal of Organic Chemistry, 55, 63 (1990), that is, by reacting an acetylene derivative with a halide in an alkylamine solvent such as diethylamine and triethylamine in the presence of a copper iodide and a Pd catalyst such as $Pd(PPh_3)_4$ and $PdCl_2(PPh_3)_2$. This reaction is preferably performed at a temperature from room temperature to the boiling point of the solvent and under an inert gas atmosphere. It can be introduced also by the Castro reaction (M. D. Raush et al., The Journal of Organic Chemistry, 34, 468 (1969).

Introduction of —O— can be carried out, for instance, by reacting a halide with an alcohol or phenol derivative in a solvent such as dimethyl sulfoxide, dimethyl formamide, 1,2-dimethoxyethane, tetrahydrofuran, hexamethylphosphoric acid triamide, and toluene in the presence of a base such as sodium amide (J. B. Wright et al., Journal of the American Chemical Society, 70, 3098 (1948)), potassium carbonate (W. T. Olson et al., Journal of the American Chemical Society, 69, 2451 (1947)), triethylamine (R. L. Merker et al., The Journal of Organic Chemistry, 26, 5180 (1961), sodium hydroxide (C. Wilkins, Synthesis, 1973, 156), potassium hydroxide (J. Rebek et al., The Journal of Organic Chemistry, 44, 1485 (1979), barium hydroxide (Kawabe et al., The Journal of Organic Chemistry, 37, 4210 (1972)), or sodium hydride (C. J. Stark, Tetrahedron Letters, 22, 2089 (1981); and K. Takai et al., Tetrahedron Letters, 21, 1657 (1980)).

While general methods for producing the compounds of the present invention are described above, more specific examples for producing starting materials, carboxylic acid derivatives and alcohol derivatives are described below.

Production of carboxylic acid derivatives:

As shown in scheme 1, compound (5) which is prepared by a method described, for example, in Japanese Patent Publication No. Hei 7-2653 is converted into compound (6) by reacting with an alcohol such as methanol and ethanol in the presence of pyridinium dichromate (PDC).

Subsequently, this compound is reacted with methoxymethylphosphonium chloride (MOTP) in the presence of a base such as potassium-tert-butoxide (t-BuOK) and then deprotected with a diluted hydrochloric acid to form compound (7).

An example of carboxylic acid derivatives (10) can be produced by reacting the compound (7) obtained by the procedures described above with a compound (8) in the presence of t-BuOK to convert the compound (7) into a compound (9), isomerizing the compound (9) with benzenesulfinic acid, and then hydrolyzing it in the presence of an alkali such as KOH and NaOH. The compound (8) mentioned above can readily be obtained by passing through the Wittig reaction of a corresponding cyclohexanone derivative with MOTP, catalytic hydrogenation in the presence of a catalyst such as Pd-C or Raney-Ni, demethylation reaction with $(CH_3)_3SiI$ or $AlCl_3$, halogenation with hydrobromic acid, hydriodic acid, or the like, and reaction with triphenylphosphine in turn.

As shown in scheme 2, an example of carboxylic acid derivatives (12) can be produced by subjecting compound (11) and the compound (8) to the Wittig reaction, isomerizing the product, and then hydrolyzing the isomerized product with an alkali.

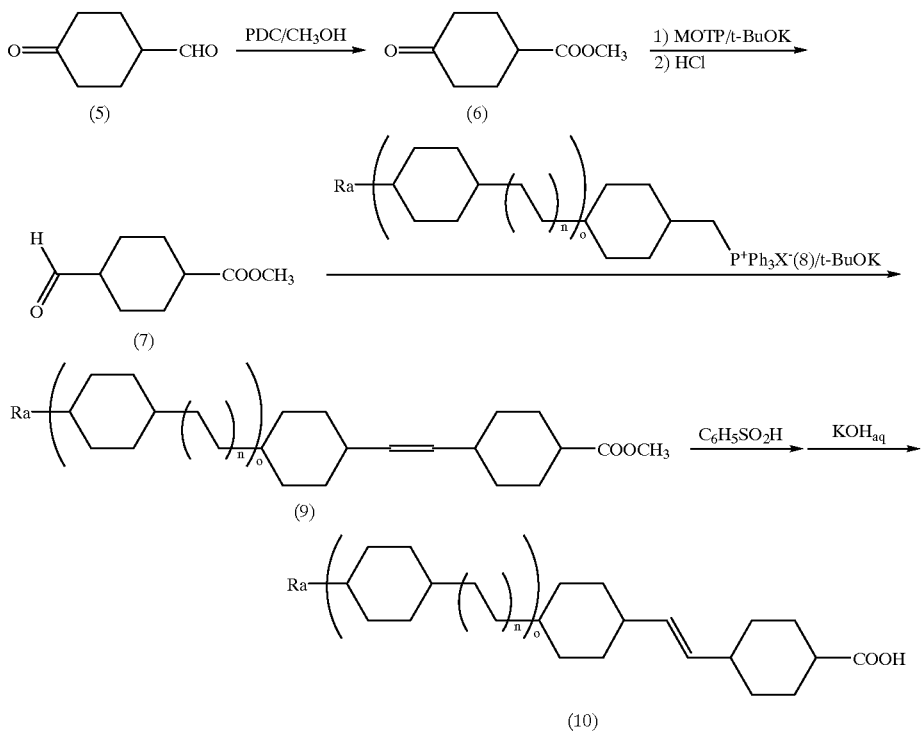

(scheme 1)

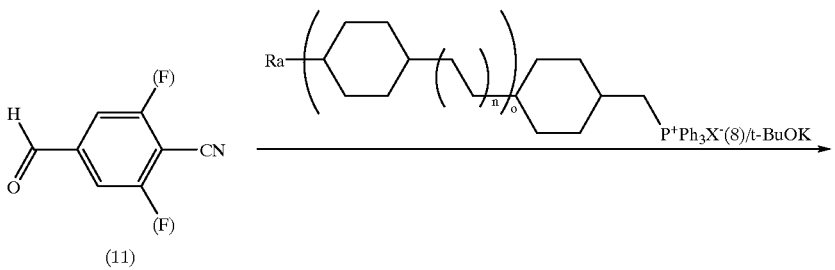

(scheme 2)

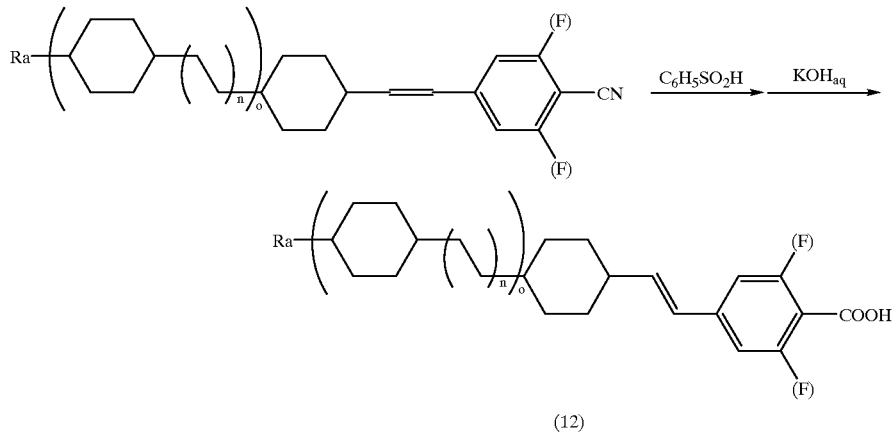

(12)

wherein Ra has the same meaning as described above, X represents a halogen atom, n is an integer of 0 to 2, and o is 0 or 1.

As shown in scheme 3, an example of carboxylic acid derivatives (14) can also be produced from compound (7) in the same manner as in scheme 1 with the exception that a compound (8) is replaced by a compound (13). Compound (13) can readily be obtained by preparing a Grignard reagent from a corresponding halide, and then passing through formylation with N-formylpiperidine or the like, reduction with sodium boron hydride or the like, halogenation, and reaction with triphenylphosphine in turn.

As shown in scheme 4, an example of carboxylic acid derivatives (15) can also be produced from compound (11) in the same manner as in scheme 2 with the exception that a compound (8) is replaced by a compound (13).

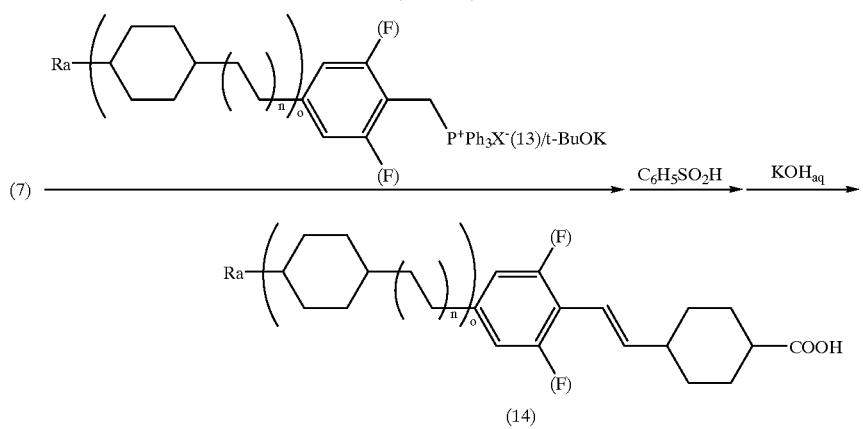

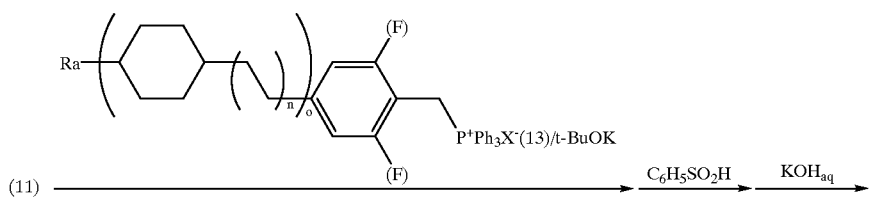

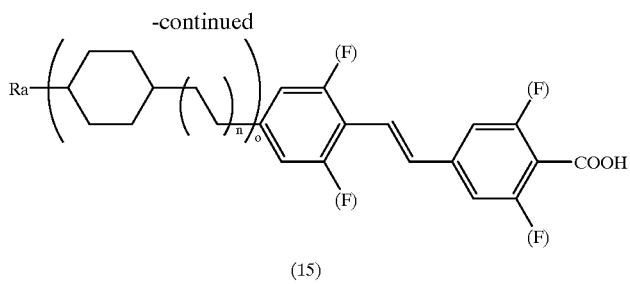

(15)

wherein Ra has the same meaning as described above, X represents a halogen atom, n is an integer of 0 to 2, and o is 0 or 1.

Production of alcohol derivatives:

As shown in scheme 5, compound (16) is converted into compound (17) by introducing a protective group such as tetrahydropyranyl group and then reacted with an organic lithium reagent such as n-butyl lithium, and iodine to convert into compound (18). Phenol derivative (19) which is an example of the alcohol derivatives can be obtained by cyanogenating the compound (18) and then deprotecting the cyanogenated compound.

As shown in scheme 6, phenol derivative (21) which is an example of the alcohol derivatives can also be obtained by reacting the compound (18) mentioned above with sodium trifluoroacetate/copper iodide (I) (G. E. Carr et al., Journal of the Chemical Society, Perkin Trans Reactions I, 921, (1988)) or methyl fluorosulfonyldifluoroacetate/copper iodide (I) (Q, Y. Chen et al., Journal of the Chemical Society, Chemical communications, 705 (1989)) to convert into compound (20), and then deprotecting this compound.

As shown in scheme 7, the compound (17) mentioned above is reacted with an organic lithium reagent such as n-butyl lithium and phenyl lithium, and formylating agent such as N-formylpiperadine (G. A. Olah et al., Angew. Chem., International Edition in English, 20, 878 (1981)), N-formylmorpholine (G. A. Olah et al., The Journal of Organic Chemistry, 49, 385 (1984)), and DMF (G. Boss et al., Chemische Berichte, 1199 (1989)) to convert into compound (22), and the compound (22) is reacted with a fluorinating agent such as diethylaminosulfurtrifluoride (DAST) (W. J. Middleton et al., The Journal of Organic Chemistry, 40, 574 (1975); S. Rozen et al., Tetrahedron Letters, 41, 111 (1985); M. Hudlicky, Organic Reactions, 35, 513 (1988); P. A. Messina et al., Journal of Fluorine Chemistry, 42, 137 (1989)) to convert into compound (23). Phenol derivative (24) which is an example of the alcohol derivatives can also be obtained by deprotecting the compound (23).

As shown in scheme 8, the compound (22) mentioned above is reduced by a reducing agent such as sodium boron hydride (SBH), lithium aluminum hydride (LAH), diisobutyl aluminum hydride (DIBAL), and sodium bis(2-methoxyethoxy)aluminum hydride (SBMEA) to convert into compound (25), and the compound (25) is reacted with a fluorinating agent such as DAST to convert into compound (26). Phenol derivative (27) which is an example of the alcohol derivatives can also be obtained by deprotecting the compound (26).

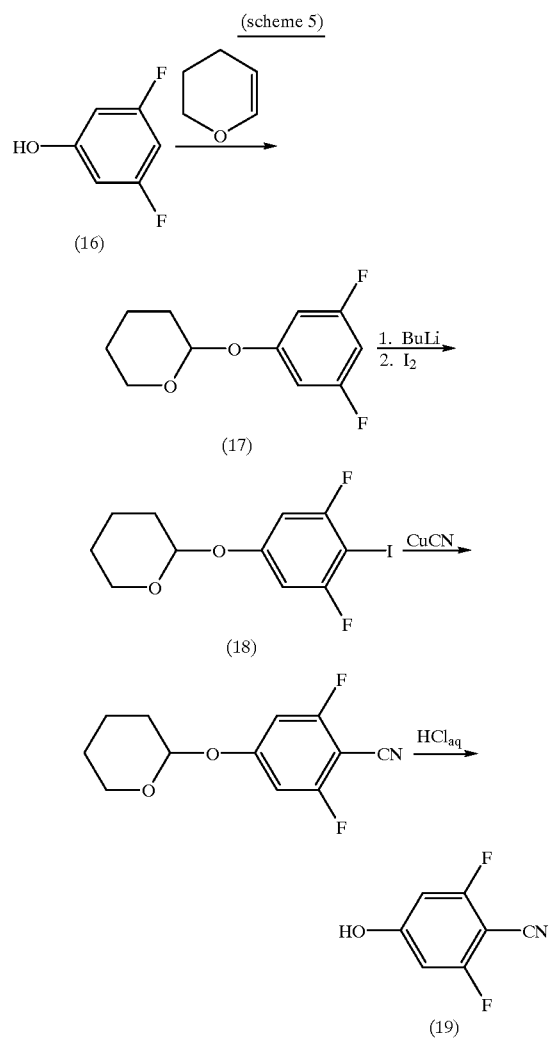

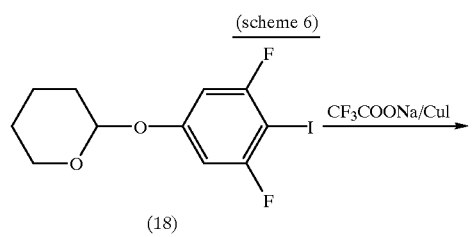

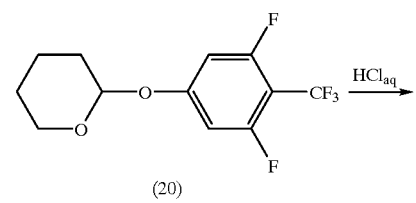

(20)

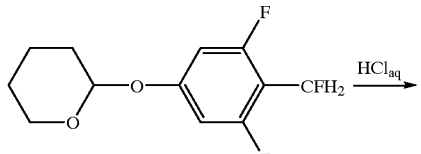

(26)

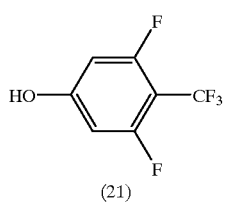

(21)

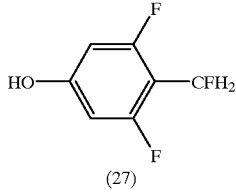

(27)

(scheme 7)

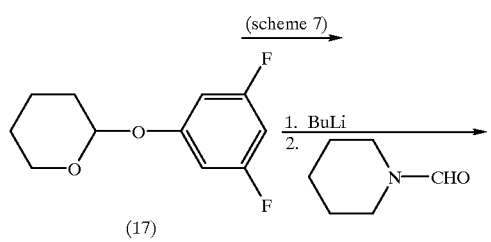

(17)

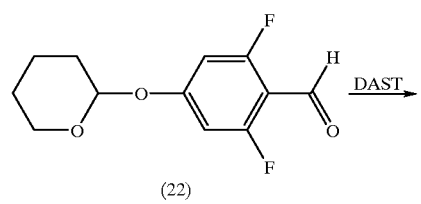

(22)

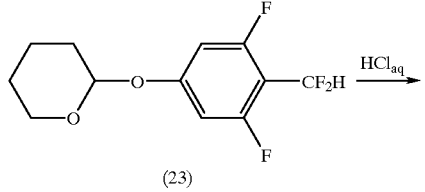

(23)

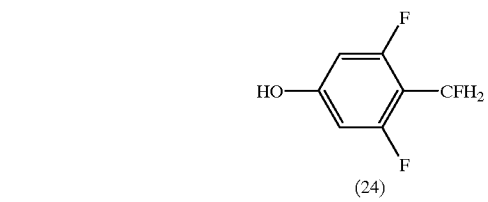

(24)

(scheme 8)

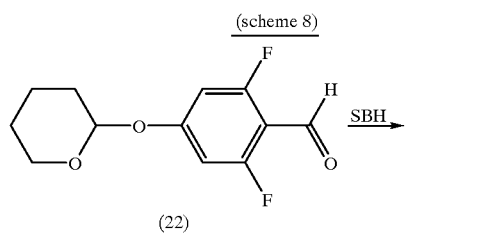

(22)

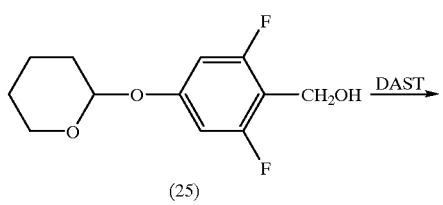

(25)

As shown in scheme 9, compound (28) is treated in the presence of nitric acid and sulfuric acid to convert into compound (29) and then converted into xanthate by the method of Albert et al. (Synthetic Communications 19, 547 (1989)). Phenol derivative (31) which is an example of the alcohol derivatives can also be obtained by fluorinating the xanthate by the method of Kurohoshi et al., (Tetrahedron Letters, 33, 29, 4173 (1992)), subjecting to a catalytic hydrogen reduction in the presence of a platinum catalyst to convert into compound (30), reacting with hydrochloric acid and sodium nitrite, and then hydrolyzing the resulting diazonium salt.

Further, as shown in scheme 10, the compound (29) mentioned above is fluorinated in a system of chlorodifluoromethane/sodium hydroxide (cf. WO Japanese Patent Publication (Tokuhyo) No. Hei 3-500413) and then subjecting the product thus obtained to a catalytic hydrogen reduction in the presence of a platinum catalyst to convert into compound (32). Phenol derivative (33) which is an example of the alcohol derivatives can also be obtained by reacting the compound (32) obtained by the procedure described above with hydrochloric acid and sodium nitrite, and then hydrolyzing the resulting diazonium salt.

(scheme 9)

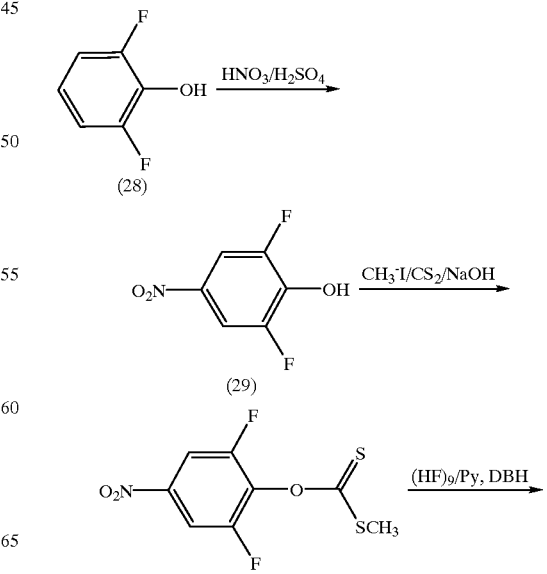

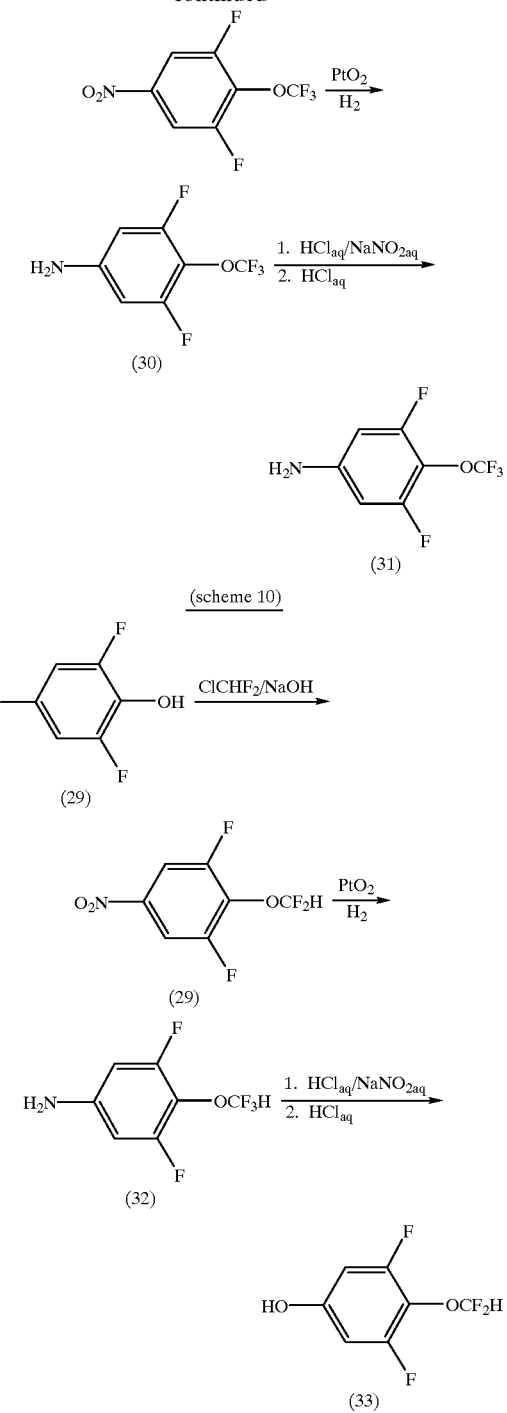

While examples of production methods are described with typical compounds of the present invention, it goes without saying that other compounds of the present invention can readily be produced, for instance, by using other known reactions in combination in addition to the reactions used in the production methods described above.

Introduction of double bond or ester bond is sufficiently performed not only at the final stage of the reactions but also at a selected suitable time.

Liquid crystalline compounds of the present invention thus obtained have a wide temperature range of liquid crystal phase, low viscosity, low threshold voltage ($V_{10}$), and excellent stability, and are readily mixed with various liquid crystal materials and good in solubility at low temperatures. Also, the compounds of the present invention are sufficiently stable chemically and physically under conditions in which liquid crystal display devices are ordinarily used and thus are remarkably excellent as component of nematic liquid crystal compositions.

Compounds of the present invention can preferably be used as component in liquid crystal compositions for TN mode, STN mode, or TFT mode.

Compounds of the present invention having three rings exhibit a wide temperature range of liquid crystal phase and a comparatively low viscosity, and the compounds having four rings exhibit a wider temperature range of liquid crystal phase and a particularly high phase transition temperature to isotropic phase.

The compounds of the present invention having two or more cyclohexane rings in the molecule exhibit a low $\Delta n$ and a low viscosity, and the compounds having two or more aromatic rings exhibit an especially wide temperature range of liquid crystal phase, a particularly high phase transition temperature to isotropic phase, and a high $\Delta n$.

Compounds of the present invention having pyridine ring, pyrimidine ring, or dioxane ring exhibit a comparatively high $\Delta \epsilon$.

Since the compounds of the present invention have a large elastic constant ratio, it is possible to make the change in transmission of liquid crystal compositions steep and thus liquid crystal display devices having a high contrast can be provided by using the compounds as component of liquid crystal compositions for STN.

Besides, the compounds can be modified toward more preferable ones as component for STN by introducing double bond in Ra and/or Rb in the formula described above.

Compounds particularly important as chiral dopant can be provided when the Ra and/or Rb is an optically active group.

When the Rb is a halogen atom, halogen substituted alkyl group, or halogen substituted alkoxy group, compounds having a high $\Delta \epsilon$; and when the Rb is cyano group, compounds exhibiting an especially high $\Delta \epsilon$ can be provided, respectively.

By substituting fluorine atom for the hydrogen atom in the ring structure, the compounds can be converted into ones having a higher $\Delta \epsilon$ and an improved mutual solubility.

When triple bond is introduced in $Z_1$, $Z_2$, or $Z_3$ in the formula described above, compounds exhibiting a high $\Delta n$ can be obtained.

As described above, new liquid crystalline compounds having desired physical properties can be obtained by selecting proper rings, substituents and/or bonding groups in the compounds of the present invention expressed by the general formula (1). At that time, each element in the compounds may be selected from their isotope.

While the liquid crystal compositions provided by the present invention may be comprised of only a first component comprising at least one liquid crystalline compound expressed by the general formula (1), the compositions preferably comprise, as a second component, at least one compound (hereinafter referred to as second component A) selected from the group consisting of the compounds expressed by any one of the general formulas (2), (3), and (4) described above and/or at least one compound (hereinafter referred to as second component B) selected from the group consisting of the compounds expressed by any one of the general formulas (5), (6), (7), (8), and (9) in addition to the first component, and further, the compositions may comprise, as a third component, a known compound for the purpose of adjusting $V_{10}$, temperature range of liquid crystal phase, $\Delta n$, $\Delta\epsilon$, or viscosity.

Among the second component A, compounds of the formulas (2-1) to (2-15) can be mentioned as preferable examples of the compounds included in the general formula (2); compounds of the formulas (3-1) to (3-48) can be mentioned as preferable examples of the compounds included in the general formula (3); and compounds of the formulas (4-1) to (4-55) can be mentioned as preferable examples of the compounds included in the general formula (4), respectively.

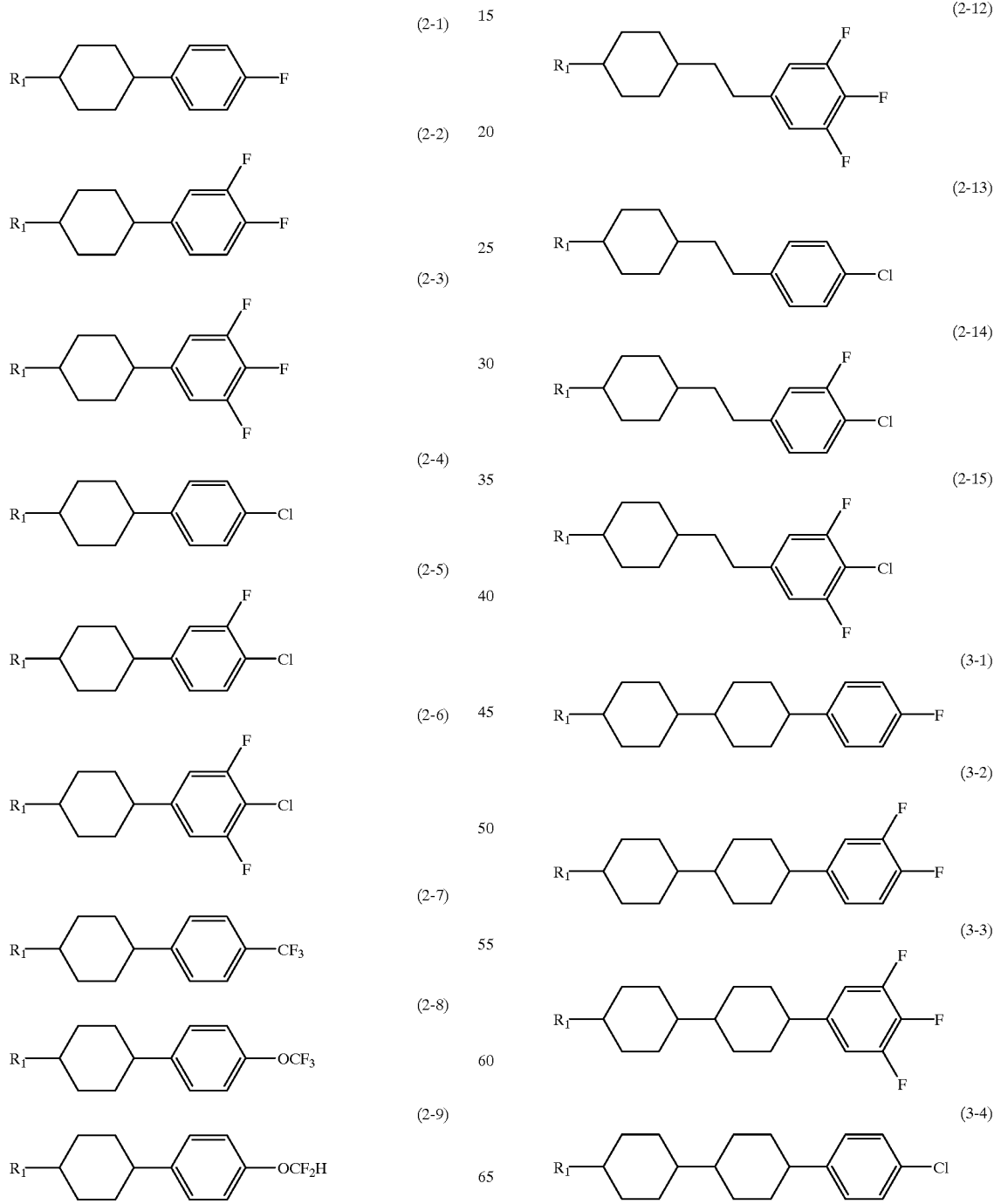

-continued
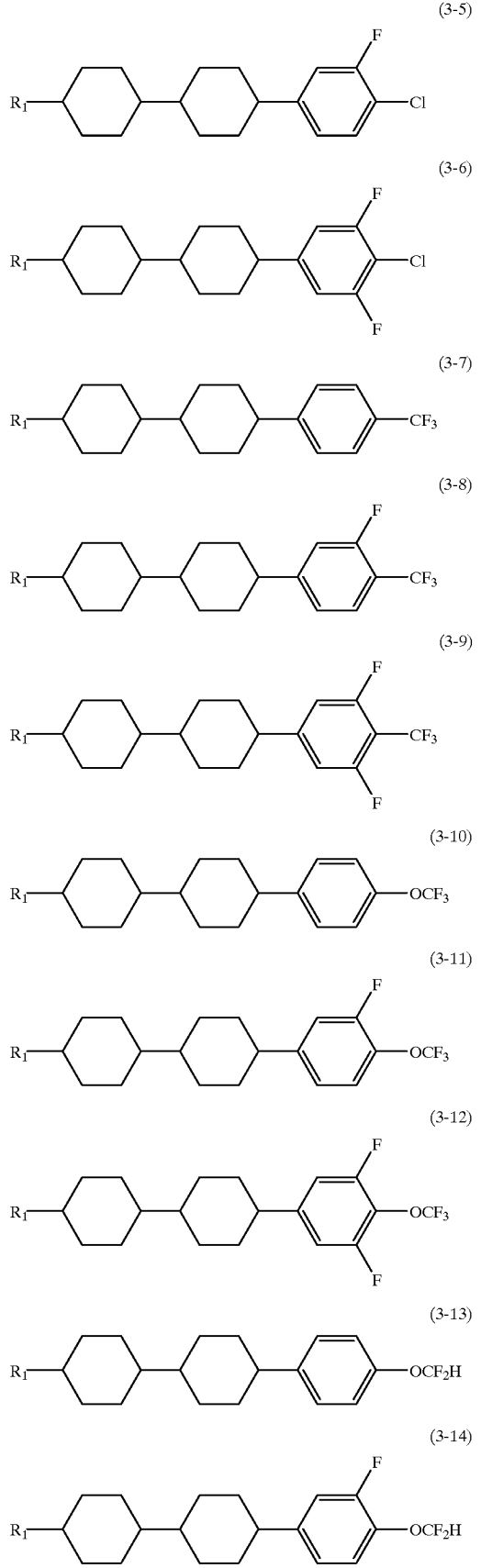
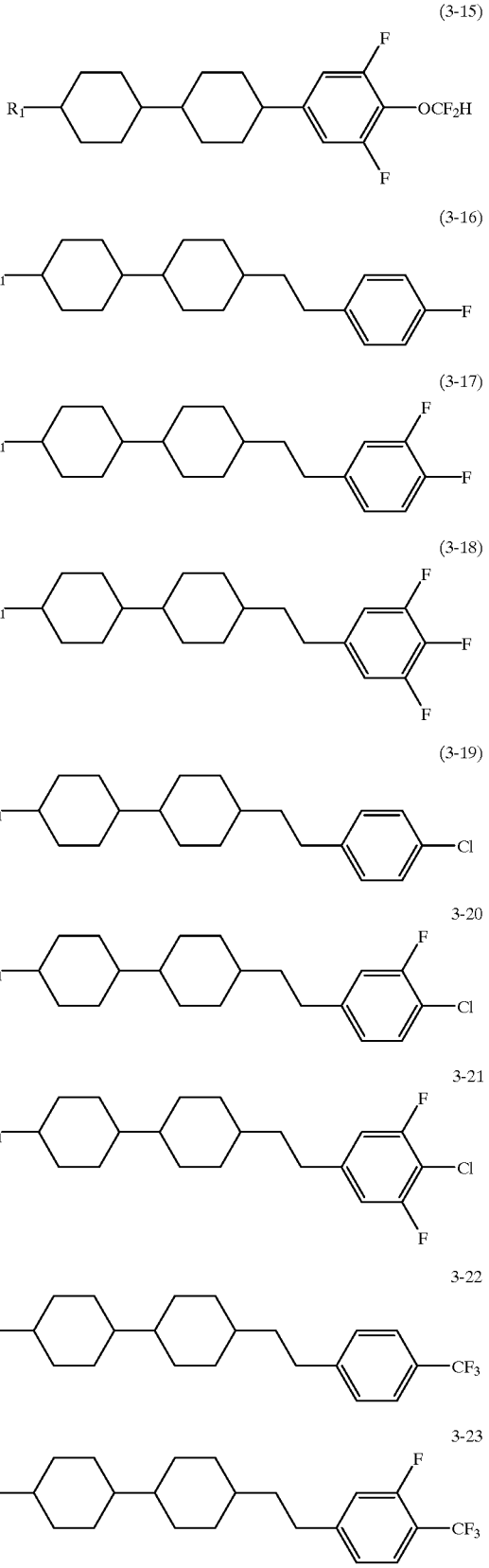

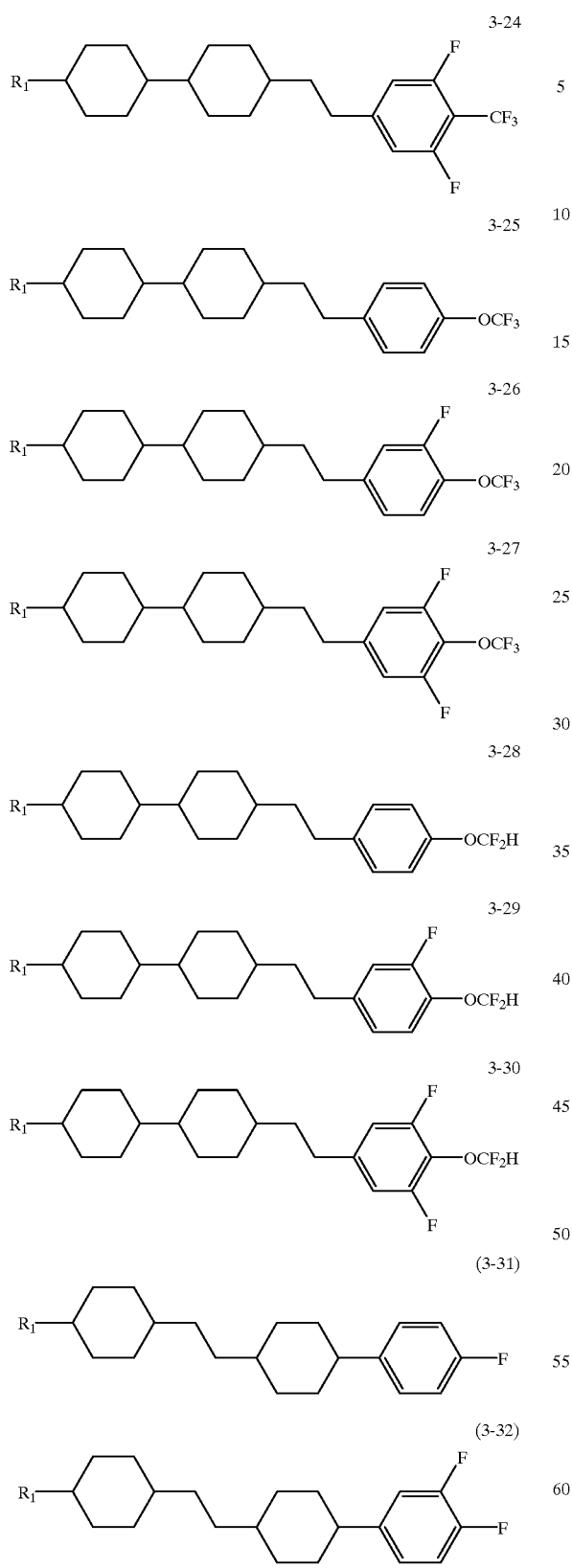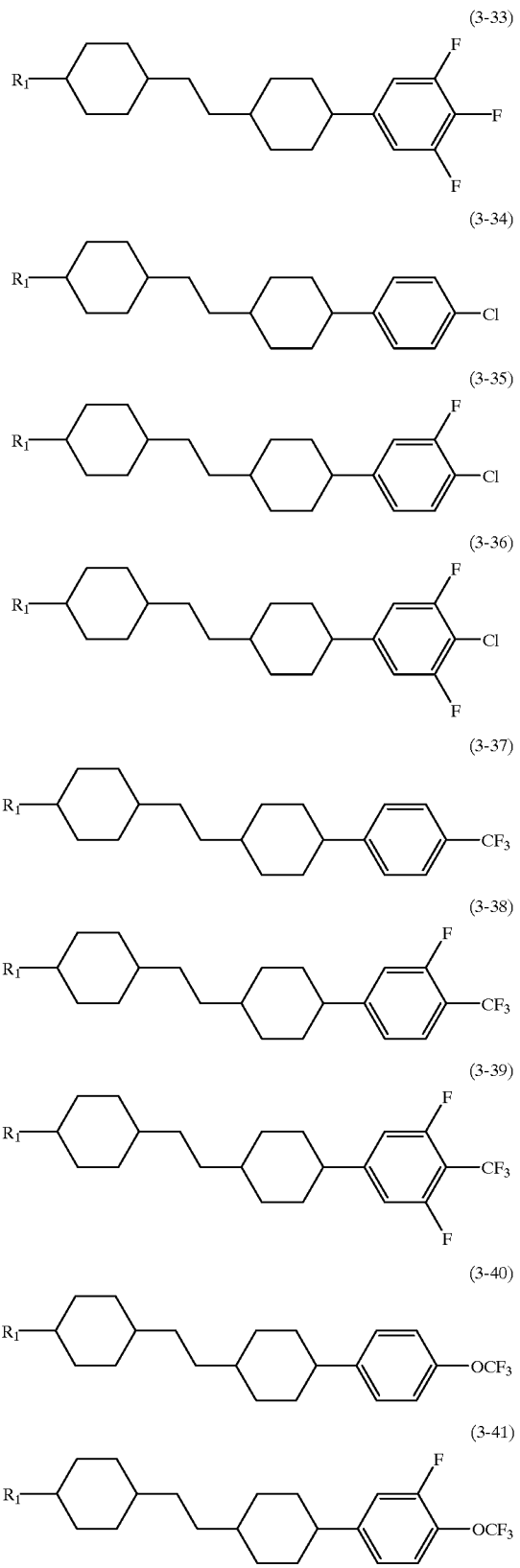

(3-42) 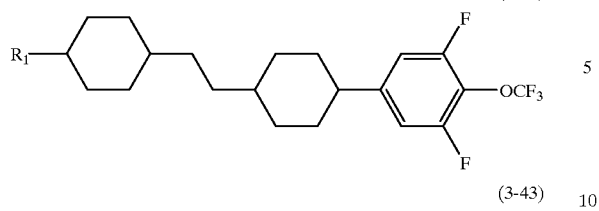
(3-43) 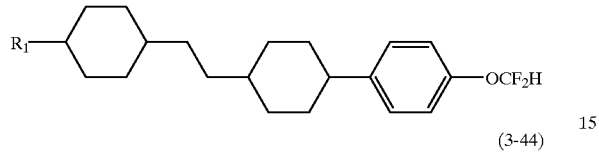
(3-44) 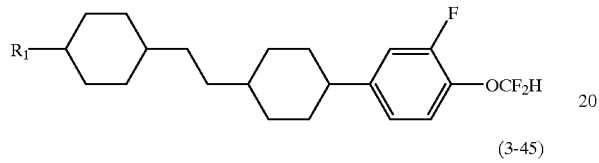
(3-45) 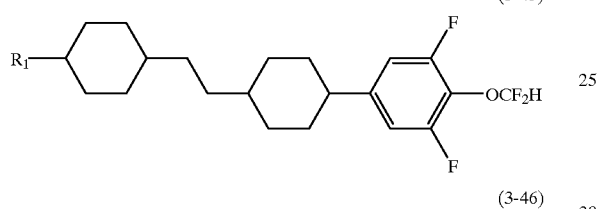
(3-46) 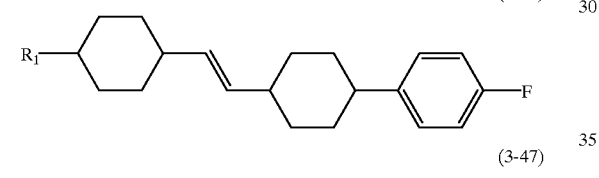
(3-47) 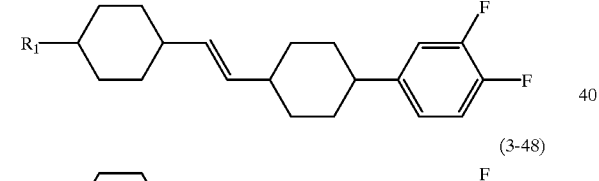
(3-48) 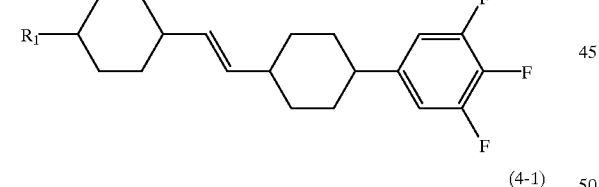
(4-1) 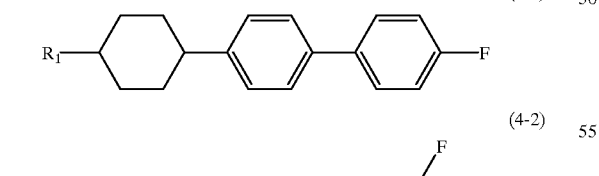
(4-2) 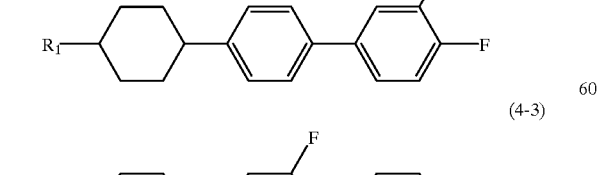
(4-3) 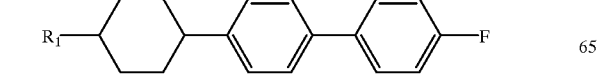
(4-4) 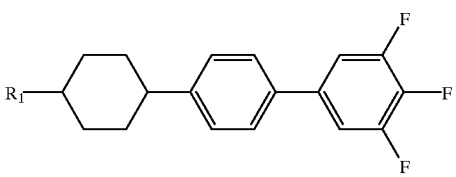
(4-5) 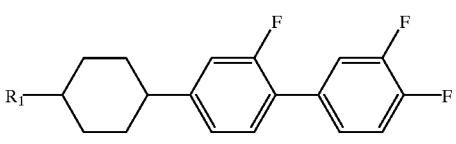
(4-6) 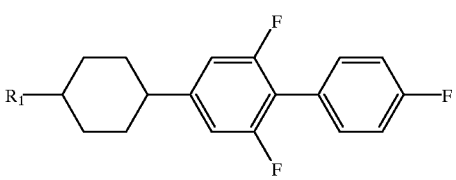
(4-7) 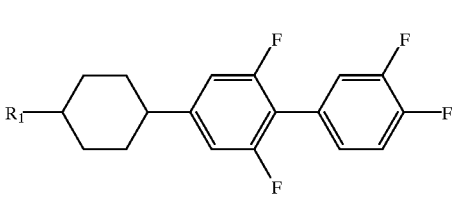
(4-8) 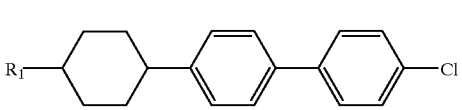
(4-9) 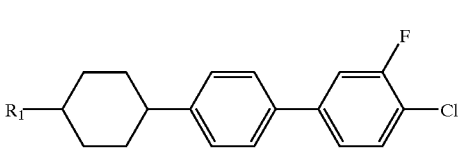
(4-10) 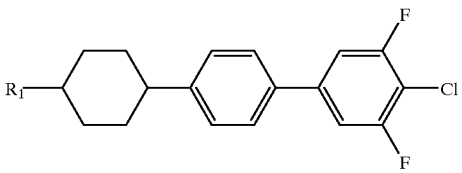
(4-11) 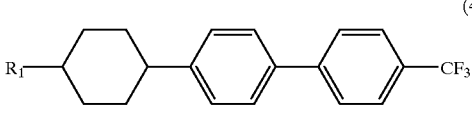
(4-12) 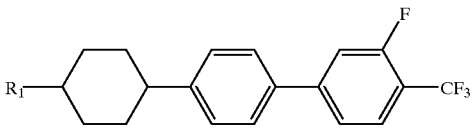

(4-13) 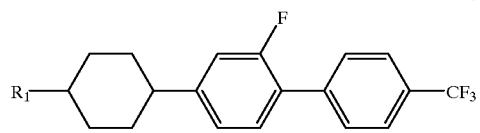
(4-14) 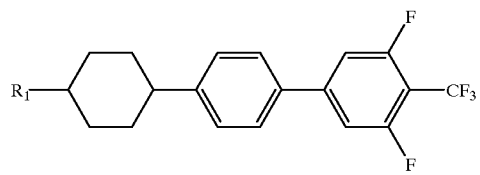
(4-15) 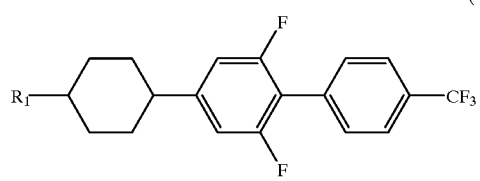
(4-16) 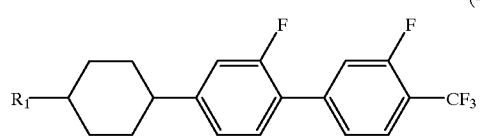
(4-17) 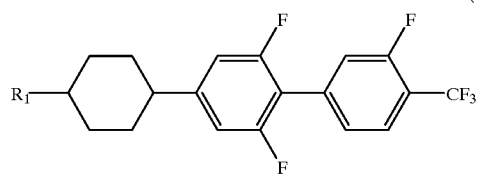
(4-18) 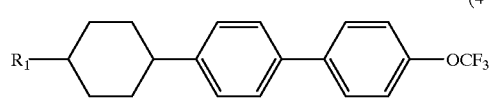
(4-19) 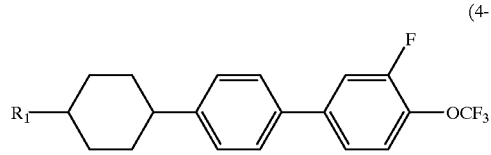
(4-20) 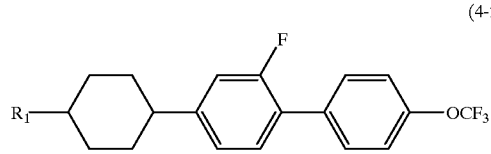
(4-21) 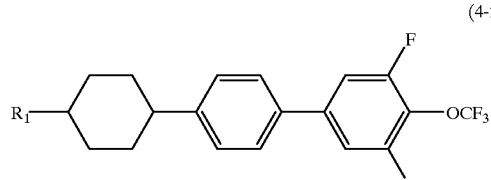
(4-22) 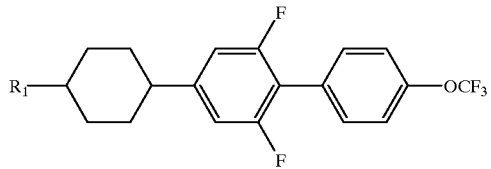
(4-23) 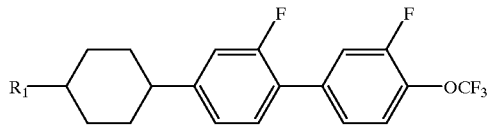
(4-24) 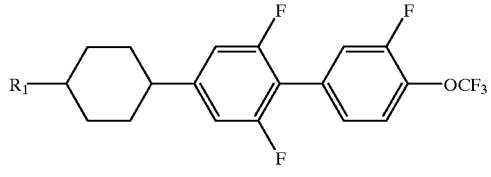
(4-25) 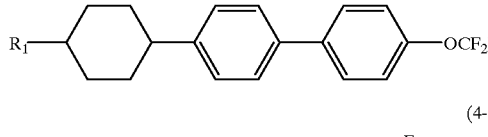
(4-26) 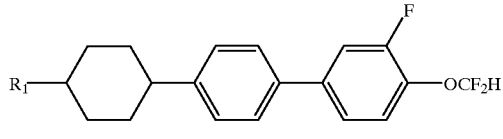
(4-27) 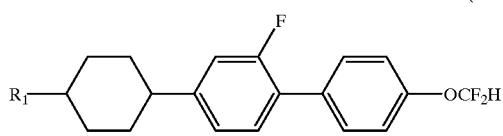
(4-28) 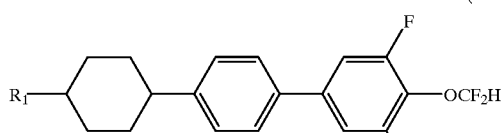
(4-29) 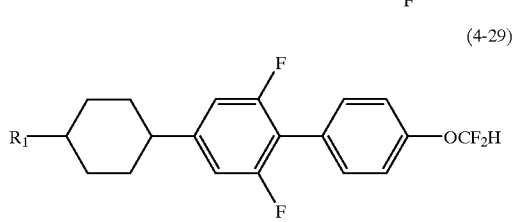
(4-30) 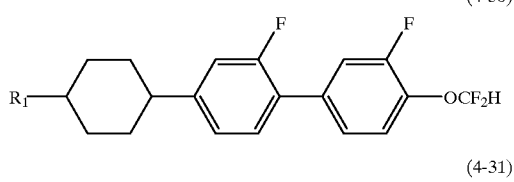
(4-31)

-continued
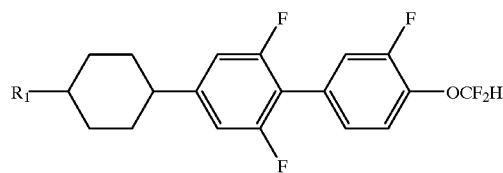
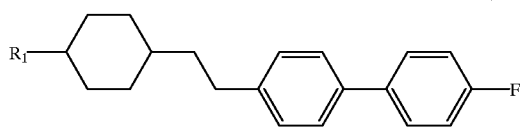
(4-32)
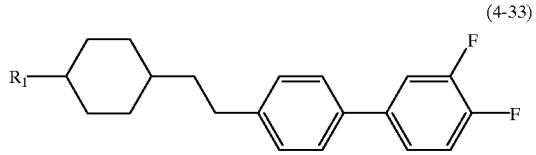
(4-33)
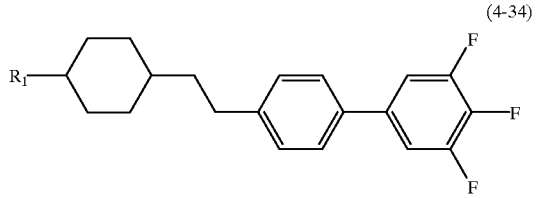
(4-34)
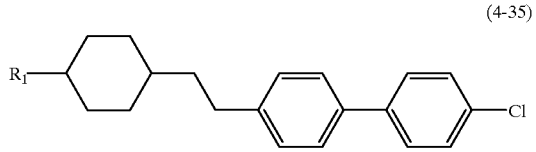
(4-35)
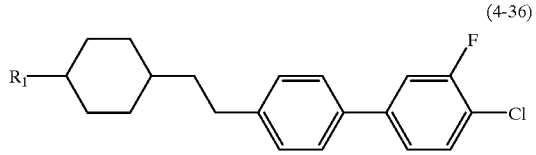
(4-36)
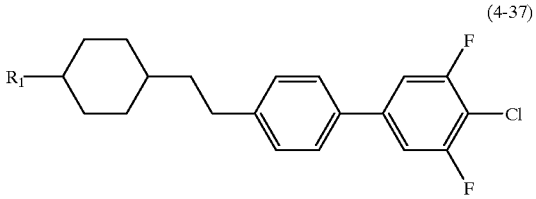
(4-37)
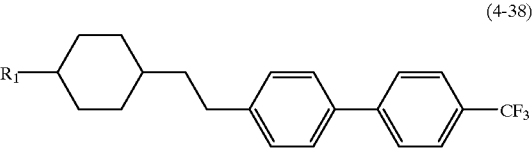
(4-38)
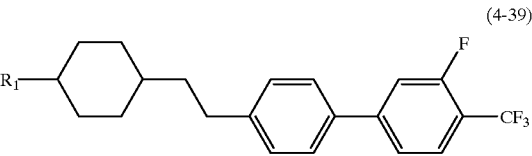
(4-39)
-continued
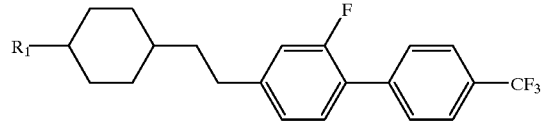
(4-40)
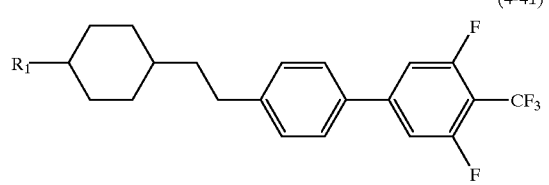
(4-41)
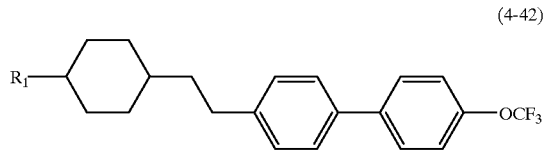
(4-42)
(4-43)
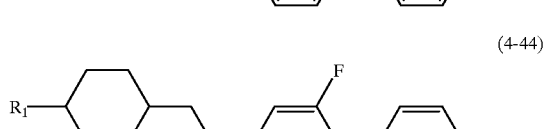
(4-44)
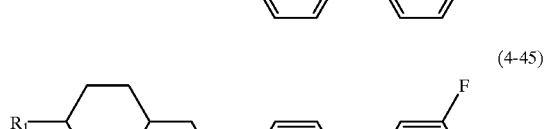
(4-45)
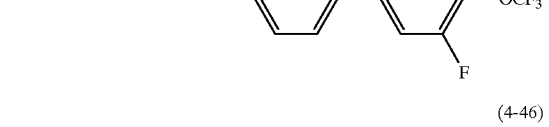
(4-46)
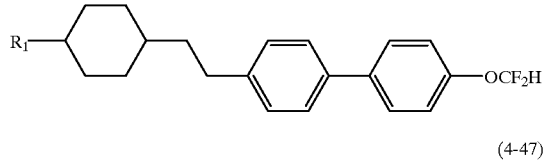
(4-47)
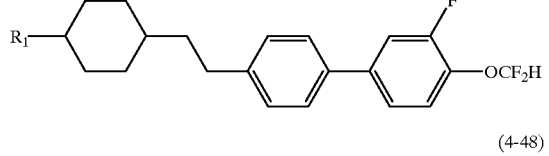
(4-48)
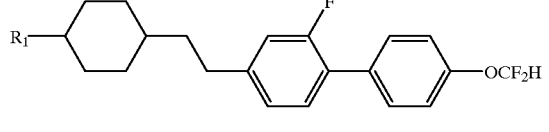

-continued

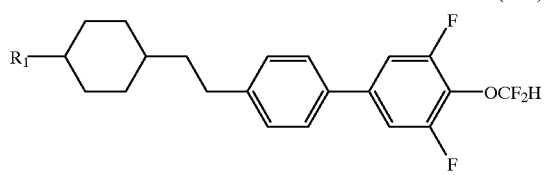
(4-49)

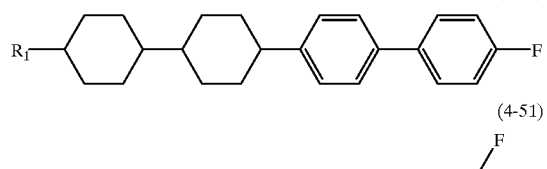
(4-50)

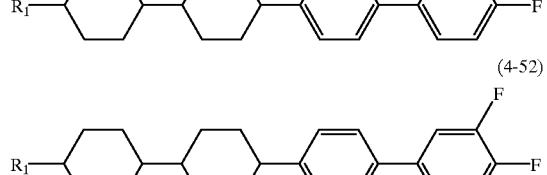
(4-51)

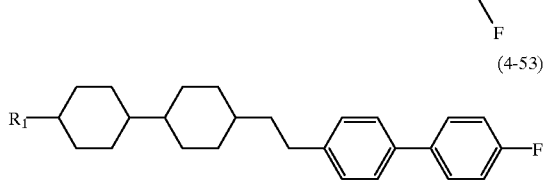
(4-52)

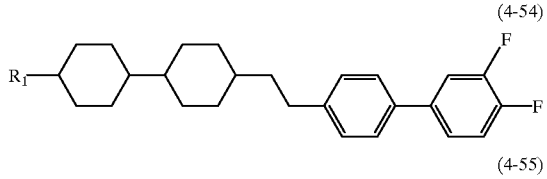
(4-53)

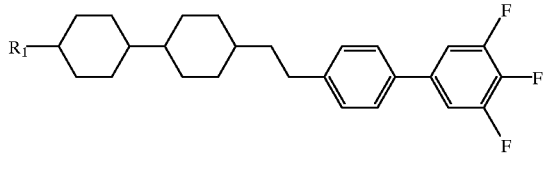
(4-54)

(4-55)

Compounds expressed by one of the general formulas (2) to (4) exhibit a positive Δε and are excellent in heat stability and chemical stability.

Amount of the compounds to be used is suitably in the range of 1 to 99% by weight, preferably 10 to 97% by weight, and more desirably 40 to 95% by weight based on the total amount of liquid crystal composition.

Among the second component B, compounds of the formulas (5-1) to (5-24), (6-1) to (6-3), and (7-1) to (7-28) can be mentioned as preferable examples of the compounds included in the general formula (5), (6), and (7), respectively.

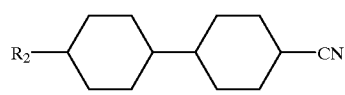
(5-1)

-continued

(5-2)

(5-3)

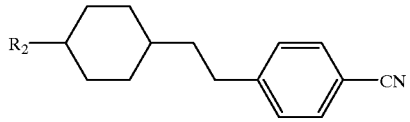
(5-4)

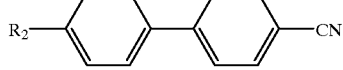
(5-5)

(5-6)

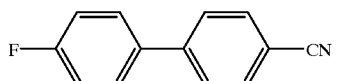
(5-7)

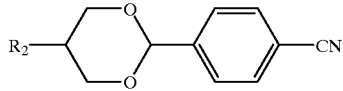
(5-8)

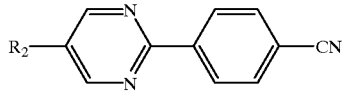
(5-9)

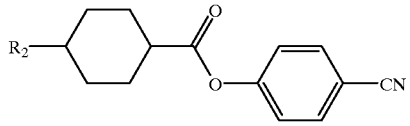
(5-10)

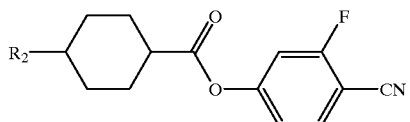
(5-11)

(5-12)

(5-13)
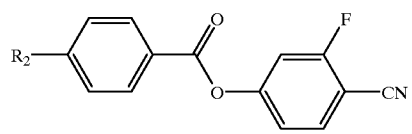
(5-14)
(5-15)
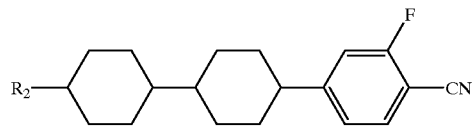
(5-16)
(5-17)
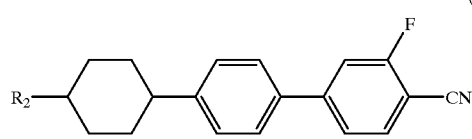
(5-18)
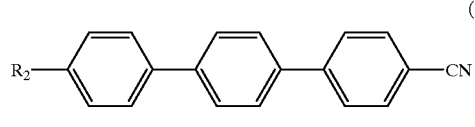
(5-19)
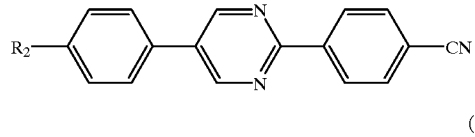
(5-20)
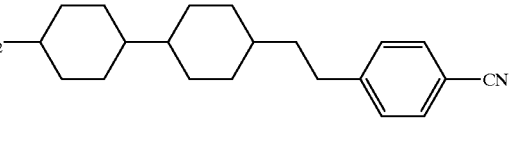
(5-21)
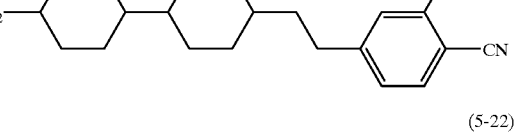
(5-22)
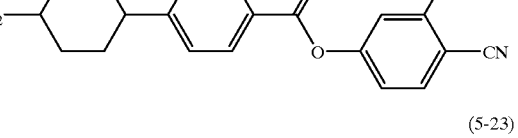
(5-23)
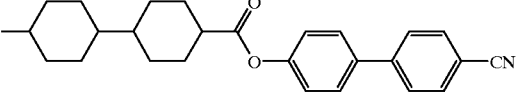
(5-24)
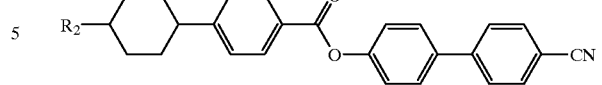
(6-1)
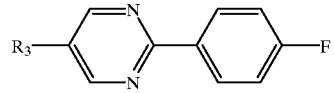
(6-2)
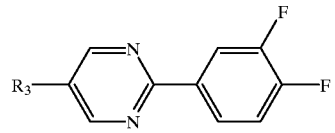
(6-3)
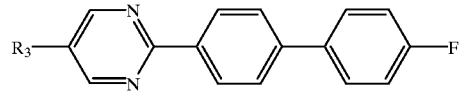
(7-1)
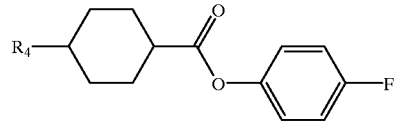
(7-2)
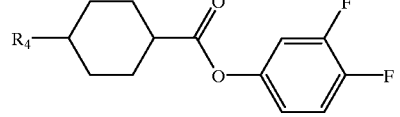
(7-3)
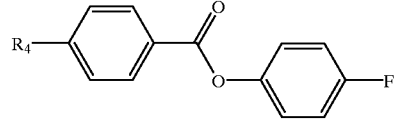
(7-4)
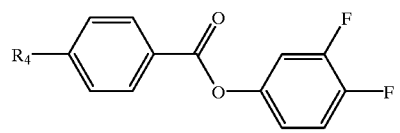
(7-5)
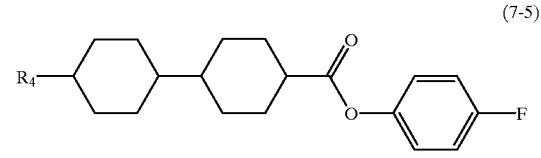
(7-6)
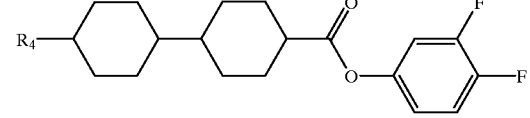

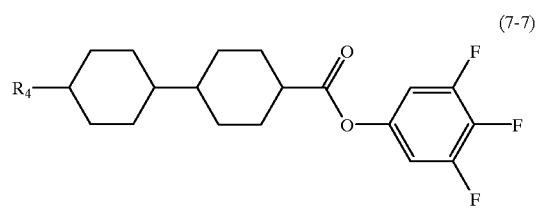
(7-7)
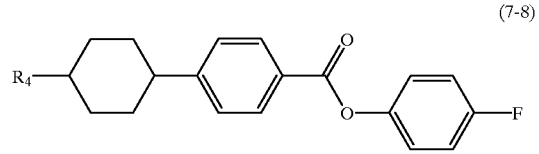
(7-8)
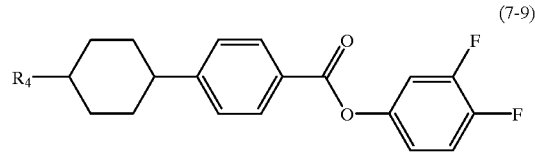
(7-9)
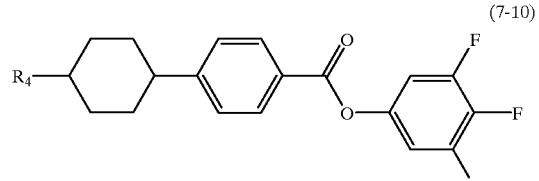
(7-10)
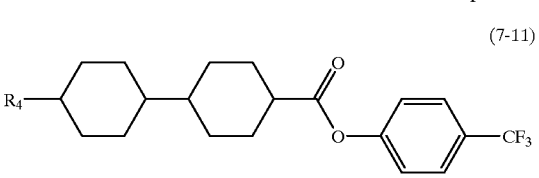
(7-11)
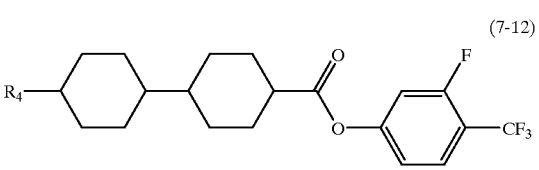
(7-12)
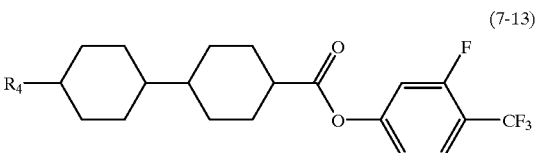
(7-13)
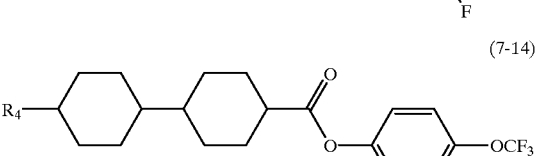
(7-14)
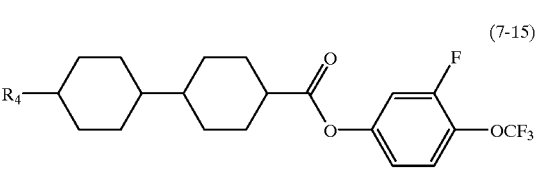
(7-15)
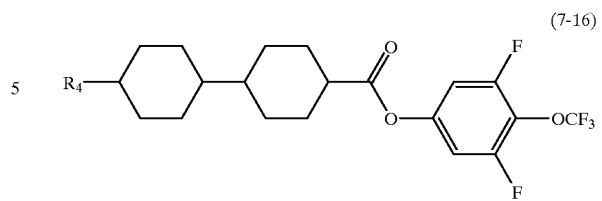
(7-16)
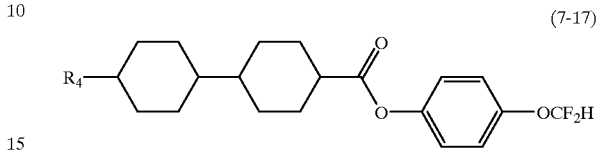
(7-17)
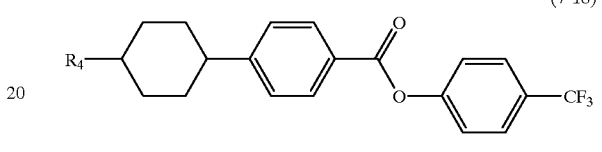
(7-18)
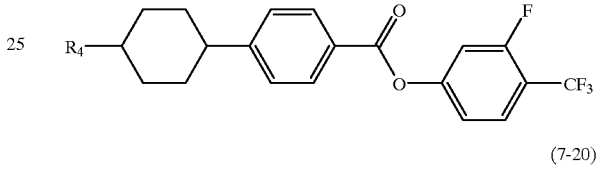
(7-19)
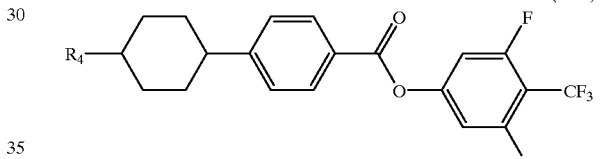
(7-20)
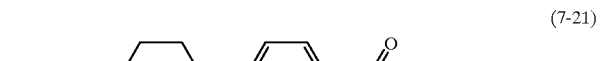
(7-21)
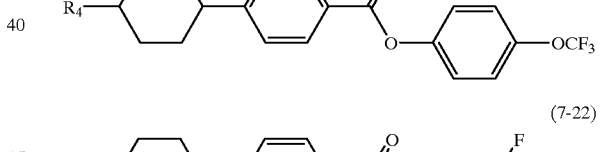
(7-22)
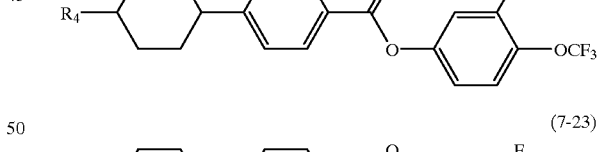
(7-23)
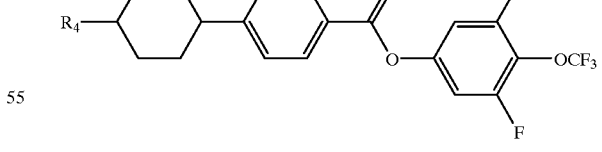
(7-24)
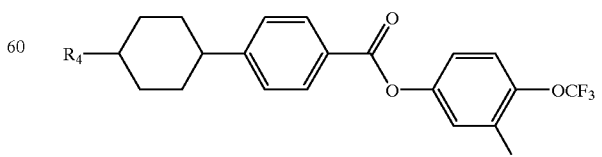

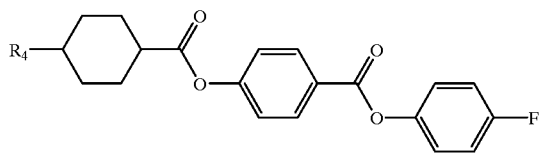
(7-25)

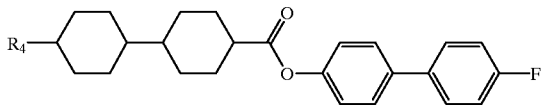
(7-26)

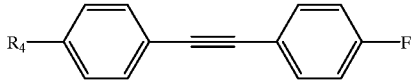
(7-27)

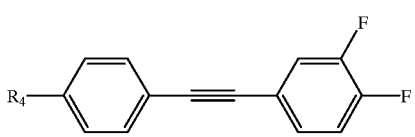
(7-28)

Compounds expressed by one of the general formulas (5) to (7) have a large positive $\Delta\epsilon$ and are used as a component of liquid crystal compositions particularly for the purpose of lowering $V_{10}$. The compounds are also used for the purpose of adjusting viscosity, adjusting $\Delta n$, or widening temperature range of liquid crystal phase, and further for the purpose of improving th steepness.

Among the second component B, the compounds of the formula (8-1) to (8-8), and (9-1) to (9-13) can be mentioned as preferable examples of the compounds included in the general formula (8) or (9).

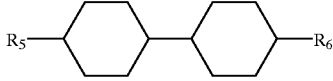
(8-1)

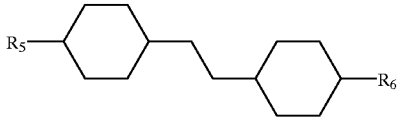
(8-2)

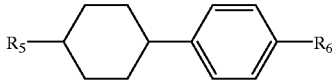
(8-3)

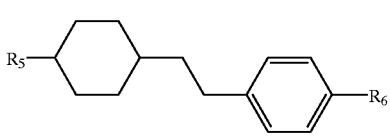
(8-4)

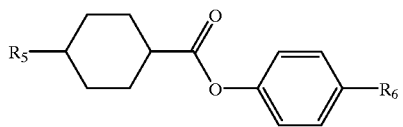
(8-5)

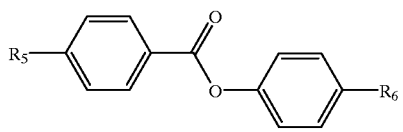
(8-6)

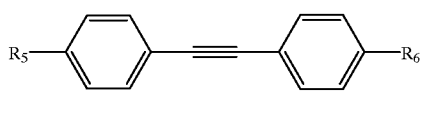
(8-7)

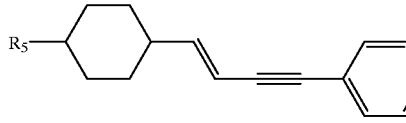
(8-8)

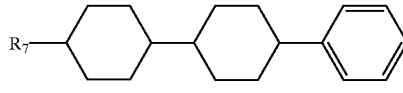
(9-1)

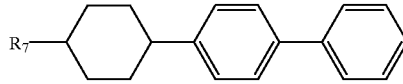
(9-2)

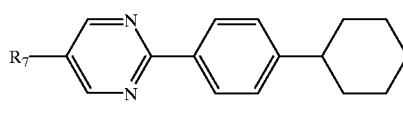
(9-3)

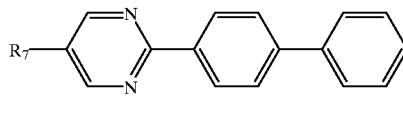
(9-4)

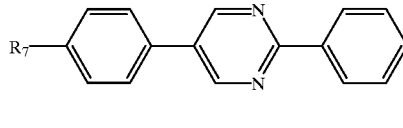
(9-5)

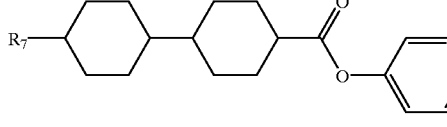
(9-6)

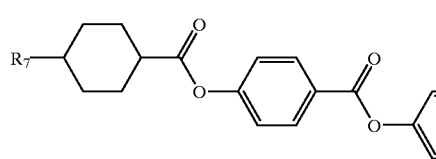
(9-7)

-continued

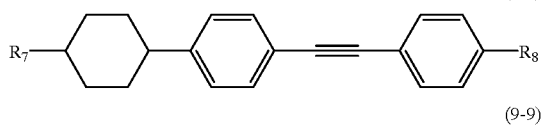 (9-8)

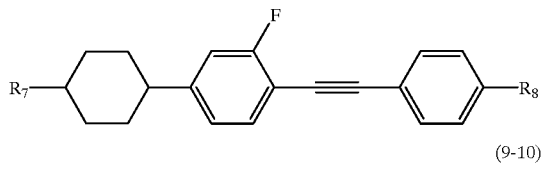 (9-9)

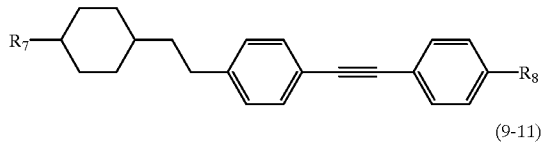 (9-10)

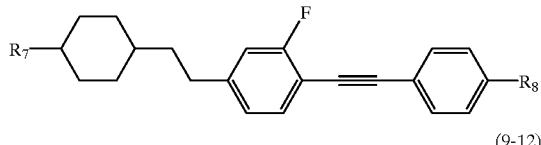 (9-11)

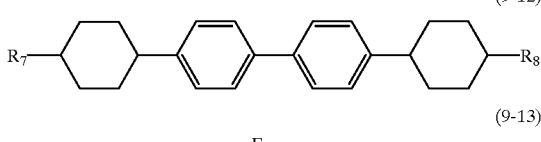 (9-12)

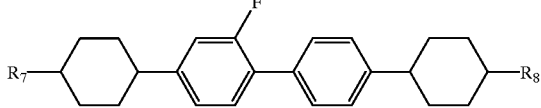 (9-13)

Compounds expressed by the general formula (8) or (9) have a negative or a small positive Δε value. Among them, the compounds expressed by the general formula (8) are used as a component of liquid crystal compositions principally for the purpose of reducing viscosity and adjusting Δn, and the compounds expressed by the general formula (9) are used for the purpose of widening temperature range of liquid crystal phase and/or for the purpose of adjusting Δn.

Compounds expressed by one of the general formulas (5) to (9) are indispensable particularly when liquid crystal compositions for STN display mode or ordinary TN display mode are produced. Amount of the compounds to be used is suitably in the range of 1 to 99% by weight, preferably 10 to 97% by weight, and 40 to 95% by weight based on the total amount of liquid crystal composition when liquid crystal compositions for ordinary STN display mode or TN display mode are produced.

Liquid crystal compositions provided according to the present invention preferably comprise at least one liquid crystalline compound expressed by the general formula (1) in the ratio of 0.1 to 99% by weight to develop excellent properties.

The liquid crystal compositions are usually produced by methods which are known by themselves, for instance, by a method in which various components are dissolved each other at a high temperature. Moreover, the liquid crystal compositions are improved and optimized depending on intended uses by adding a suitable additive, when necessary. Such an additive is well known in the art and described in detail in the literature. Usually, a chiral dopant or the like is added to induce a helical structure of liquid crystals thereby adjust a required twisting angle and avoid a reverse-twist. As its examples, optically active compounds expressed by one of the following formulas (Op-1) to (Op-8) can be mentioned.

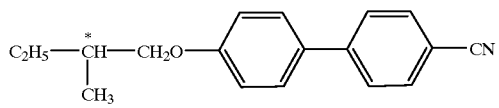 (Op-1)

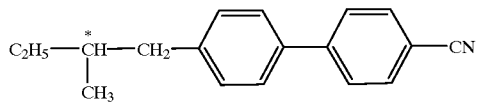 (Op-2)

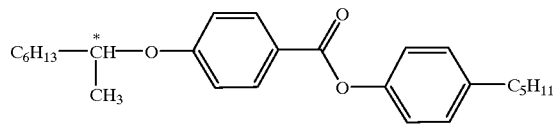 (Op-3)

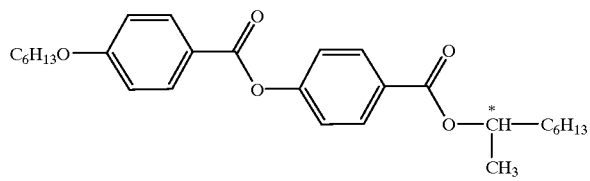 (Op-4)

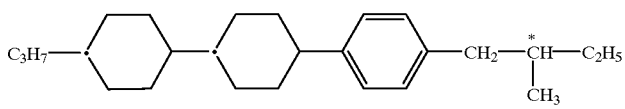
(Op-5)

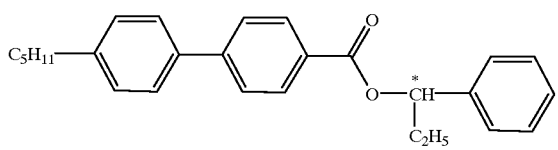
(Op-6)

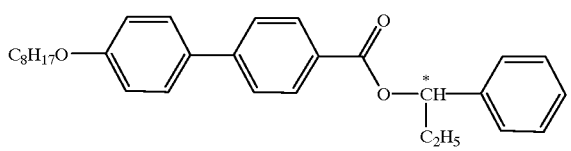
(Op-7)

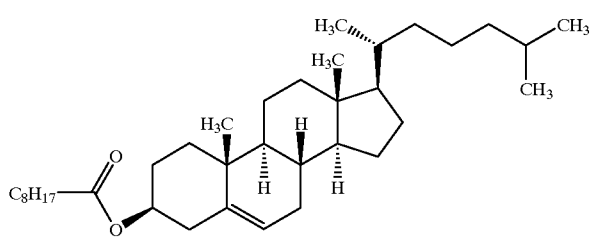
(Op-8)

Liquid crystal compositions of the present invention can be used as ones for GH (guest-host) mode by adding a dichroic dye such as merocyanine type, styryl type, azo type, azomethine type, azoxy type, quinophthalone type, anthraquinone type, or tetrazine type dye. Liquid crystal compositions of the present invention can also be used as liquid crystal compositions for NCAP which is prepared by the microencapsulation of a nematic liquid crystal, or for polymer dispersed liquid crystal display devices (PDLCD) which are prepared by forming in the liquid crystal a three-dimesnsional network structure of a polymer, for example, polymer network liquid crystal display devices (PNLCD) as well as for electrically controlled birefringence (ECB) mode or dynamic scattering (DS) mode.

Liquid crystal compositions of the present invention are produced by the methods as described above, and the following Composition Examples 1 through 33 can be shown as examples of the compositions.

In the composition examples, compounds are designated by the abbreviation according to the definitions shown in the following Table 1. Specifically, left hand side terminal group is indicated by n-, nO-, Vn-, nVm-, or nVmVk- (n, m, and k are an integer of 1 or more); bonding group is indicated by 2, E, T, V, or CF2O; ring structure is indicated by B, B(F), B(F,F), H, Py, D, or Ch; right hand side terminal group is indicated by —F, —CL, —C, —CF3, —OCF3, —OCF2H, -n, -On, or -Eme (n is an integer of 1 or more). Number of compound affixed to the compounds of the present invention is the same as that shown in Examples below.

TABLE 1

| Left side terminal group | Symbol | Bonding group | Symbol |
|---|---|---|---|
| $C_nH_{2n+1}$— | n— | —$CH_2CH_2$— | 2 |
| $C_nH_{2n+1}$O— | nO— | —COO— | E |
| $C_nH_{2n+1}C_mH_{2m}$— | nOm— | —C≡C— | T |
| $CH_2$=$CHC_nH_{2n}$— | Vn— | —CH=CH— | V |
| $C_nH_{2n+1}CH_2$=$CHC_mH_{2m}$— | nVm— | —$CF_2$O— | CF2O |
| $C_nH_{2n+1}CH_2$=$CHC_mH_{2m}CH$=$CHC_kH_{2k}$— | nVmVk— | | |

| Ring structure | Symbol | Right side terminal group | Symbol |
|---|---|---|---|
| 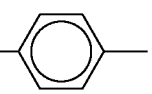 | B | —F—<br>—Cl— | —F<br>—CL |
| 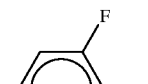 | B(F) | —CN<br>—$CF_3$ | —C<br>—CF3 |
| 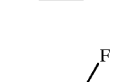 | B(F, F) | —$OCF_3$<br>—$OCF_2H$ | —OCF3<br>—OCF2H |

| | H | —$C_nH_{2n+1}$<br>—$OC_nH_{2n+1}$ | —n<br>—On |
|---|---|---|---|
|  | Py | —$COOCH_3$ | —EMe |
| 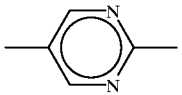 | D | | |
| 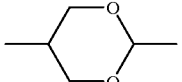 | Ch | | |

Composition Example 1

| | | |
|---|---|---|
| 3-HVBEB(F, F)—C | (No. 1) | 10.0% by weight |
| 5-HVHEB(F, F)—C | (No. 60) | 10.0% by weight |
| 3-HVB(F, F)EB(F, F)—C | (No. 23) | 10.0% by weight |
| 5-HVHEB-5 | (No. 74) | 15.0% by weight |
| V-HVHEH-3 | (No. 97) | 15.0% by weight |
| 5-HVHEB(F)—OCF3 | (No. 51) | 10.0% by weight |
| 3-HVB(F, F)EB(F, F)—CF3 | (No. 25) | 10.0% by weight |
| 3-HVB(F, F)EB(F)—OCF3 | (No. 20) | 10.0% by weight |
| 3-HVBEB(F, F)—CF3 | (No. 13) | 10.0% by weight |

Composition Example 2

| | | |
|---|---|---|
| 5-HVHEB-5 | (No. 74) | 10.0% by weight |
| 5-HVHEB(F)—OCF3 | (No. 51) | 15.0% by weight |
| 3-HVB(F, F)EB(F, F)—CF3 | (No. 25) | 10.0% by weight |
| 3-HVB(F, F)EB(F)—OCF3 | (No. 20) | 10.0% by weight |
| 3-HVBEB(F, F)—CF3 | (No. 13) | 15.0% by weight |
| 3-HVBEB(F)—CF3 | (No. 6) | 10.0% by weight |
| 3-HVBEB(F, F)—OCF3 | (No. 14) | 10.0% by weight |
| 3-HVBEB(F, F)—OCF2H | (No. 15) | 10.0% by weight |
| 5-HVHEB(F)—CF2H | (No. 58) | 10.0% by weight |

Composition Example 3

| | | |
|---|---|---|
| 5-HVHEB-5 | (No. 74) | 5.0% by weight |
| V2-HB—C | | 10.0% by weight |
| 1V2-HB—C | | 10.0% by weight |
| 3-HB—C | | 26.0% by weight |
| 5-HB—C | | 12.0 % by weight |
| 3-HB(F)—C | | 8.0% by weight |
| 2-BEB—C | | 3.0% by weight |
| V2-HHB-1 | | 3.0% by weight |
| 3-HHB—O1 | | 4.0% by weight |
| 3-HHB-3 | | 10.0% by weight |
| 3-H2BTB-2 | | 3.0% by weight |
| 3-H2BTB-3 | | 3.0% by weight |
| 3-H2BTB-4 | | 3.0% by weight |

Composition Example 4

| | | |
|---|---|---|
| 3-HVBEB(F, F)—C | (No. 1) | 10.0% by weight |
| 3-HVHEB(F, F)—C | (No. 60) | 5.0% by weight |
| 3-HVB(F, F)EB(F, F)—C | (No. 23) | 5.0% by weight |
| 1V2-BEB(F, F)—C | | 11.0% by weight |
| 2O1-BEB(F)—C | | 5.0% by weight |
| 3O1-BEB(F)—C | | 9.0% by weight |
| 3-HB(F)—C | | 15.0% by weight |
| 3-HH-4 | | 5.0% by weight |
| 1O1-HH-3 | | 3.0% by weight |
| 4-BTB—O2 | | 5.0% by weight |
| 2-HHB(F)—C | | 3.0% by weight |
| 3-HHB(F)—C | | 4.0% by weight |
| 3-H2BTB-2 | | 4.0% by weight |
| 3-H2BTB-3 | | 4.0% by weight |
| 3-H2BTB-4 | | 4.0% by weight |
| 2-BTB-1 | | 1.0% by weight |
| 1-BTB-6 | | 2.0% by weight |
| 4-BTB-4 | | 1.0% by weight |
| 3-HH-2V | | 2.0% by weight |
| 4-HH—V | | 2.0% by weight |

Composition Example 5

| | | |
|---|---|---|
| V-HVHEH-3 | (No. 97) | 3.0% by weight |
| 5-HVHEB-5 | (No. 74) | 5.0% by weight |
| 2-BB—C | | 6.0% by weight |
| 2O2O—BB—C | | 3.0% by weight |
| 1O1-HB—C | | 10.0% by weight |
| 2O1-HB—C | | 7.0% by weight |
| 2-BEB—C | | 12.0% by weight |
| 5-PyB—F | | 8.0% by weight |
| 2-PyB-2 | | 2.0% by weight |
| 3-PyB-2 | | 2.0% by weight |
| 4-PyB-2 | | 2.0% by weight |
| V—HHB-1 | | 5.0% by weight |
| 3-HHB-1 | | 7.0% by weight |
| 3-HHB-3 | | 10.0% by weight |
| 2-PyBH-3 | | 5.0% by weight |
| 3-PyBH-3 | | 3.0% by weight |
| 4-PyBH-3 | | 3.0% by weight |
| 3-PyBB—F | | 2.0% by weight |
| 4-PyBB—F | | 2.0% by weight |
| 6-PyBB-2 | | 3.0% by weight |

Composition Example 6

| | | |
|---|---|---|
| 3-HVBEB(F, F)—C | (No. 1) | 3.0% by weight |
| 5-HVHEB-5 | (No. 74) | 3.0% by weight |
| 3-PyB(F)—F | | 6.0% by weight |
| 2-BEB—C | | 12.0% by weight |
| 3-BEB—C | | 4.0% by weight |
| 3-DB—C | | 10.0% by weight |
| 4-DB—C | | 10.0% by weight |
| 3-HEB—O4 | | 8.0% by weight |
| 4-HEB—O2 | | 6.0% by weight |
| 5-HEB—O1 | | 6.0% by weight |
| 3-HEB—O2 | | 5.0% by weight |
| 5-HEB—O2 | | 4.0% by weight |
| 3-HHB-1 | | 3.0% by weight |
| 3-HHEBB—C | | 3.0% by weight |
| 5-HBEBB—C | | 3.0% by weight |
| 1O—BEB-2 | | 4.0% by weight |
| 4-HEB-3 | | 4.0% by weight |
| 5-HEB-1 | | 4.0% by weight |
| 6-PyB—O2 | | 2.0% by weight |

Composition Example 7

| | | |
|---|---|---|
| 5-HVHEB(F, F)—C | (No. 60) | 3.0% by weight |
| 3-HB—C | | 20.0% by weight |
| 3-HHB-1 | | 7.0% by weight |
| 3-HHB-3 | | 8.0% by weight |
| 5-HEB—F | | 2.5% by weight |
| 7-HEB—F | | 2.5% by weight |
| 3-HHEB—F | | 1.0% by weight |
| 5-HHEB—F | | 1.0% by weight |
| 3-HEB—O4 | | 4.0% by weight |
| 4-HEB—O2 | | 3.0% by weight |
| 5-HEB—O1 | | 3.0% by weight |
| 3-HEB—O2 | | 2.5% by weight |
| 5-HEB—O2 | | 2.0% by weight |
| 3-HB(F)TB-2 | | 6.0% by weight |
| 3-HB(F)TB-3 | | 5.0% by weight |
| 3-HB(F)—VB-4 | | 5.0% by weight |
| 3-H2BTB-2 | | 4.0% by weight |
| 3-H2BTB-3 | | 4.0% by weight |
| 3-H2BTB-4 | | 4.0% by weight |
| 3-HHEBB—C | | 3.0% by weight |
| 3-HBEBB—C | | 3.0% by weight |
| 5-HBEBB—C | | 3.0% by weight |
| 3-HH—COOMe | | 1.5% by weight |
| 1O1-HBBH-3 | | 2.0% by weight |

Composition Example 8

| | | |
|---|---|---|
| 5-HVHEB(F, F)—C | (No. 60) | 5.0% by weight |
| 5-PyB(F)—F | | 13.0% by weight |
| 2-HB(F)—C | | 10.0% by weight |
| 3-HB(F)—C | | 12.0% by weight |
| 3O—BB—C | | 8.0% by weight |

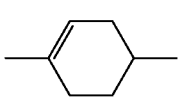

TABLE 1-continued

| | | |
|---|---|---|
| 2-HHB—C | | 6.0% by weight |
| 3-HHB—C | | 6.0% by weight |
| 4-HHB—C | | 6.0.% by weight |
| 5-HHB—C | | 6.0% by weight |
| 2-HHB(F)—C | | 5.0% by weight |
| 3-HHB(F)—C | | 5.0% by weight |
| 3-PyBB—F | | 7.0% by weight |
| 4-PyBB—F | | 6.0% by weight |
| 5-HBB—C | | 2.0% by weight |
| 3-HB(F)EB(F)—C | | 3.0% by weight |
| Composition Example 9 | | |
| 5-HVHEB(F)—OCF3 | (No. 51) | 12.0% by weight |
| 3-HVB(F, F)EB(F)—OCF3 | (No. 20) | 8.0% by weight |
| 3-HVBEB(F)—CF3 | (No. 6) | 8.0% by weight |
| 5-HVHEB(F)—CF2H | (No. 58) | 8.0% by weight |
| 5-H2B(F)—F | | 4.0% by weight |
| 7-HB(F)—F | | 10.0% by weight |
| 2-HHB(F)—F | | 5.0% by weight |
| 3-HHB(F)—F | | 5.0% by weight |
| 5-HHB(F)—F | | 5.0% by weight |
| 2-H2HB(F)—F | | 8.0% by weight |
| 3-H2HB(F)—F | | 4.0% by weight |
| 5-H2HB(F)—F | | 8.0% by weight |
| 2-HBB(F)—F | | 2.5% by weight |
| 3-HBB(F)—F | | 2.5% by weight |
| 5-HBB(F)—F | | 5.0% by weight |
| 3-HHB—F | | 5.0% by weight |
| Composition Example 10 | | |
| 3-HVB(F, F)EB(F, F)—CF3 | (No. 25) | 5.0% by weight |
| 3-HVBEB(F, F)—OCF3 | (No. 14) | 5.0% by weight |
| 3-HVBEB(F, F)—OCF2H | (No. 15) | 5.0% by weight |
| 7-HB(F, F)—F | | 5.0% by weight |
| 3-HBB(F, F)—F | | 4.0% by weight |
| 5-HBB(F, F)—F | | 4.0% by weight |
| 3-HHB(F, F)—F | | 7.0% by weight |
| 5-HHB(F, F)—F | | 5.0% by weight |
| 3-HH2B(F, F)—F | | 5.0% by weight |
| 5-HH2B(F, F)—F | | 5.0% by weight |
| 3-H2HB(F, F)—F | | 9.0% by weight |
| 4-H2HB(F, F)—F | | 9.0% by weight |
| 5-H2HB(F, F)—F | | 9.0% by weight |
| 3-HHEB(F, F)—F | | 9.0% by weight |
| 4-HHEB(F, F)—F | | 3.0% by weight |
| 5-HHEB(F, F)—F | | 3.0% by weight |
| 3-HBEB(F, F)—F | | 2.0% by weight |
| 5-HBEB(F, F)—F | | 2.0% by weight |
| 3-HHHB(F, F)—F | | 2.0% byweight |
| 5-HH2BB(F, F)—F | | 2.0% by weight |
| Composition Example 11 | | |
| 5-HVHEB(F)—OCF3 | (No. 51) | 6.0% by weight |
| 3-HVBEB(F, F)—CF3 | (No. 13) | 5.0% by weight |
| 7-HB(F, F)—F | | 5.0% by weight |
| 2-HHB(F) F | | 10.0% by weight |
| 3-HHB(F)—F | | 10.0% by weight |
| 5-HHB(F)—F | | 10.0% by weight |
| 3-HHB-OCF3 | | 3.0% by weight |
| 5-HHB-OCF3 | | 3.0% by weight |
| 2-H2HB(F)—F | | 4.0% by weight |
| 3-H2HB(F)—F | | 2.0% by weight |
| 5-H2HB(F)—F | | 4.0% by weight |
| 3-HHB(F, F)—F | | 8.0% by weight |
| 4-HHB(F, F)—F | | 4.0% by weight |
| 3-H2HB(F, F)—F | | 5.0% by weight |
| 4-H2HB(F, F)—F | | 4.0% by weight |
| 5-H2HB(F, F)—F | | 4.0% by weight |
| 3-HH2B(F, F)—F | | 5.0% by weight |
| 5-HH2B(F, F)—F | | 5.0% by weight |
| 3-HH2B-OCF3 | | 3.0% by weight |
| Composition Example 12 | | |
| 5-HVHEB(F)—OCF3 | (No. 51) | 10.0% by weight |
| 5-HVHEB-5 | (No. 74) | 6.0% by weight |
| 3-HVB(F, F)EB(F)—OCF3 | (No. 20) | 5.0% by weight |
| 5-HB—F | | 5.0% by weight |
| 7-HB(F)—F | | 5.0% by weight |
| 2-HHB(F)—F | | 10.0% byweight |
| 3-HHB(F)—F | | 10.0% by weight |
| 5-HHB(F)—F | | 10.0% by weight |
| 3-HB—O2 | | 10.0% by weight |
| 3-HHB—F | | 4.0% by weight |
| 3-HHB-1 | | 3.0% by weight |
| 3-HHB-3 | | 3.0% by weight |
| 2-HBB—F | | 6.0% by weight |
| 3-HBB—F | | 5.0% by weight |
| 3-HHEB—F | | 2.0% by weight |
| 5-HHEB—F | | 2.0% by weight |
| 3-HBEB—F | | 2.0% by weight |
| 3-HHEBB—F | | 2.0% by weight |
| Composition Example 13 | | |
| 5-HVHEB(F)—OCF3 | (No. 51) | 5.0% by weight |
| 3-HVB(F, F)EB(F, F)—CF3 | (No. 25) | 3.0% by weight |
| 3-HVBEB(F, F)—CF3 | (No. 13) | 2.0% by weight |
| 7-HB(F, F)—F | | 7.0% by weight |
| 3-HB—CL | | 4.0% by weight |
| 5-HB—CL | | 3.0% by weight |
| 7-HB—CL | | 3.0% by weight |
| 2-BTB—O1 | | 12.0% by weight |
| 2-HBB(F)—F | | 2.5% by weight |
| 3-HBB(F)—F | | 2.5% by weight |
| 5-HBB(F)—F | | 5.0% by weight |
| 5-HBB(F, F)—F | | 5.0% by weight |
| 2-HBB—CL | | 5.0% by weight |
| 3-HBB—CL | | 5.0% by weight |
| 3-HB(F)TB-2 | | 6.0% by weight |
| 3-HB(F)TB-3 | | 6.0% by weight |
| 3-HB(F)TB-4 | | 6.0% by weight |
| 3-H2BTB-2 | | 4.0% by weight |
| 3-H2BTB-3 | | 4.0% by weight |
| 3-H2HB(F)—CL | | 3.0% by weight |
| 5-H2HB(F)—CL | | 2.0% by weight |
| 3-H2BB(F, F)—F | | 5.0% by weight |
| Composition Example 14 | | |
| 4-HVHEB(F)—OCF3 | (No. 51) | 10.0% by weight |
| 5-HVHEB(F)—CF2H | (No. 58) | 10.0% by weight |
| 5-HVHEB-5 | (No. 74) | 5.0% by weight |
| 5-HB—F | | 10.0% by weight |
| 6-HB—F | | 5.0% by weight |
| 7-HB—F | | 5.0% by weight |
| 2-HHB—OCF3 | | 5.0% by weight |
| 3-HHB—OCF3 | | 5.0% by weight |
| 5-HHB—OCF3 | | 5.0% by weight |
| 3-HH2B—OCF3 | | 6.0% by weight |
| 5-HH2B—OCF3 | | 6.0% by weight |
| 3-HB(F)B-3 | | 4.0% by weight |
| 5-HB(F)B-3 | | 4.0% by weight |
| 2-HBB(F)—F | | 5.0% by weight |
| 3-HBB(F)—F | | 5.0% by weight |
| 5-HBB(F)—F | | 10.0% by weight |
| Composition Example 15 | | |
| 3-HVB(F, F)EB(F, F)—CF3 | (No. 25) | 6.0% by weight |
| 3-HVBEB(F, F)—OCF2H | (No. 15) | 6.0% by weight |
| 5-HB—F | | 3.0% by weight |
| 6-HB—F | | 3.0% by weight |
| 7-HB—F | | 3.0% by weight |
| 3-HHB—OCHF2 | | 4.0% by weight |
| 5-HHB—OCHF2 | | 4.0% by weight |
| 3-HHB(F, F)—OCF2H | | 9.0% by weight |
| 5-HHB(F, F)—OCF2H | | 9.0% by weight |
| 2-HHB—OCF3 | | 6.0% by weight |
| 3-HHB—OCF3 | | 6.0% by weight |
| 4-HHB—OCF3 | | 6.0% by weight |
| 5-HHB—OCF3 | | 6.0% by weight |
| 3-HH2B(F)—F | | 10.0% by weight |
| 5-HH2B(F)—F | | 10.0% by weight |
| 3-HHEB(F)—F | | 4.0% by weight |
| 5-HHEB(F)—F | | 5.0% by weight |
| Composition Example 16 | | |
| 3-HVBEB(F, F)—C | (No. 1) | 4.0% by weight |
| 5-HVHEB(F, F)—C | (No. 60) | 4.0% by weight |
| 5-HVHEB-5 | (No. 74) | 5.0% by weight |
| 4-HHEB(F)—F | | 5.0% by weight |

TABLE 1-continued

| | | |
|---|---|---|
| 5-HHEB(F)—F | | 5.0% by weight |
| 2-BEB(F)—C | | 5.0% by weight |
| 3-BEB(F)—C | | 7.0% by weight |
| 4-BEB(F)—C | | 5.0% by weight |
| 5-BEB(F)—C | | 7.0% by weight |
| 1O3-HB(F)—C | | 11.0% by weight |
| 3-HHEB(F)—F | | 5.0% by weight |
| 5-HHEB(F)—F | | 5.0% by weight |
| 2-HBEB(F)—C | | 3.0% by weight |
| 3-HBEB(F)—C | | 3.0% by weight |
| 4-HBEB(F)—C | | 3.0% by weight |
| 5-HBEB(F)—C | | 3.0% by weight |
| 3-HBTB-2 | | 5.0% by weight |
| V2-HH-3 | | 10.0% by weight |
| V2-HHB-1 | | 5.0% by weight |
| Composition Example 17 | | |
| 3-HVBEB(F, F)—C | (No. 1) | 5.0% by weight |
| 3-HVB(F, F)EB(F, F)—C | (No. 23) | 5.0% by weight |
| 1V2-BEB(F, F)—C | | 5.0% by weight |
| 3-HB—C | | 15.0% by weight |
| 1-BTB-3 | | 5.0% by weight |
| 2-BTB-1 | | 10.0% by weight |
| 3-HH-4 | | 11.0% by weight |
| 3-HHB-1 | | 11.0% by weight |
| 3-HHB-3 | | 9.0% by weight |
| 3-H2BTB-2 | | 4.0% by weight |
| 3-H2BTB-3 | | 4.0% by weight |
| 3-H2BTB-4 | | 4.0% by weight |
| 3-HB(F)TB-2 | | 6.0% by weight |
| 3-HB(F)TB-3 | | 6.0% by weight |
| Composition Example 18 | | |
| 5-HVHEB(F, F)—C | (No. 60) | 5.0% by weight |
| 3O1-BEB(F)—C | | 15.0% by weight |
| 4O1-BEB(F)—C | | 13.0% by weight |
| 5O1-BEB(F)—C | | 13.0% by weight |
| 2-HHB(F)—C | | 15.0% by weight |
| 3-HHB(F)—C | | 15.0% by weight |
| 3-HB(F)TB-2 | | 4.0% by weight |
| 3-HB(F)TB-3 | | 4.0% by weight |
| 3-HB(F)TB-4 | | 4.0% by weight |
| 3-HHB-1 | | 8.0% by weight |
| 3-HHB—O1 | | 4.0% by weight |
| Composition Example 19 | | |
| 5-HVHEB-5 | (No. 74) | 6.0% by weight |
| 5-PyB—F | | 4.0% by weight |
| 3-PyB(F)—F | | 4.0% by weight |
| 2-BB—C | | 5.0% by weight |
| 4-BB—C | | 4.0% by weight |
| 5-BB—C | | 5.0% by weight |
| 2-PyB-2 | | 2.0% by weight |
| 3-PyB-2 | | 2.0% by weight |
| 4-PyB-2 | | 2.0% by weight |
| 6-PyB—O5 | | 3.0% by weight |
| 6-PyB—O6 | | 3.0% by weight |
| 6-PyB—O7 | | 3.0% by weight |
| 6-PyB—O8 | | 3.0% by weight |
| 3-PyBB—F | | 6.0% by weight |
| 4-PYBB—F | | 6.0% by weight |
| 5-PyBB—F | | 6.0% by weight |
| 3-HHB-3 | | 8.0% by weight |
| 2-H2BTB-2 | | 4.0% by weight |
| 2-H2BTB-3 | | 4.0% by weight |
| 2-H2BTB-4 | | 5.0% by weight |
| 3-H2BTB-2 | | 5.0% by weight |
| 3-H2BTB-3 | | 5.0% by weight |
| 3-H2BTB-4 | | 5.0% by weight |
| Composition Example 20 | | |
| 3-HVBEB(F, F)—C | (No. 1) | 3.0% by weight |
| 5-HVHEB-5 | (No. 74) | 3.0% by weight |
| 3-DB—C | | 10.0% by weight |
| 4-DB—C | | 10.0% by weight |
| 2-BEB—C | | 12.0% by weight |
| 3-BEB—C | | 4.0% by weight |
| 3-PyB(F)—F | | 6.0% by weight |
| 3-HEB—O4 | | 8.0% by weight |
| 4-HEB—O2 | | 6.0% by weight |
| 5-HEB—O1 | | 6.0% by weight |
| 3-HEB—O2 | | 5.0% by weight |
| 5-HEB—O2 | | 4.0% by weight |
| 5-HEB-5 | | 5.0% by weight |
| 4-HEB-5 | | 5.0% by weight |
| 1O—BEB-2 | | 4.0% by weight |
| 3-HHB-1 | | 3.0% by weight |
| 3-HHEBB—C | | 3.0% by weight |
| 3-HBEBB—C | | 3.0% by weight |
| Composition Example 21 | | |
| 3-HVB(F, F)EB(F, F)—C | (No. 23) | 3.0% by weight |
| 3-HB—C | | 15.0% by weight |
| 7-HB—C | | 3.0% by weight |
| 1O1-HB—C | | 10.0% by weight |
| 3-HB(F)—C | | 10.0% by weight |
| 2-PyB-2 | | 2.0% by weight |
| 3-PyB-2 | | 2.0% by weight |
| 4-PyB-2 | | 2.0% by weight |
| 1O1-HH-3 | | 7.0% by weight |
| 2-BTB—O1 | | 7.0% by weight |
| 3-HHB-1 | | 7.0% by weight |
| 3-HHB—F | | 4.0% by weight |
| 3-HHB—O1 | | 4.0% by weight |
| 3-HHB-3 | | 8.0% by weight |
| 3-H2BTB-2 | | 3.0% by weight |
| 3-H2BTB-3 | | 3.0% by weight |
| 2-PyBH-3 | | 4.0% by weight |
| 3-PyBH-3 | | 3.0% by weight |
| 3-PyBB-2 | | 3.0% by weight |
| Composition Example 22 | | |
| 3-HVB(F, F)EB(F, F)—C | (No. 23) | 5.0% by weight |
| 3-HVBEB(F, F)—C | (No. 1) | 12.0% by weight |
| 5-HVHEB-5 | (No. 74) | 3.0% by weight |
| 5O1-BEB(F)—C | | 4.0% by weight |
| 1V2-BEB(F, F)—C | | 10.0% by weight |
| 3-HH—EMe | | 10.0% by weight |
| 3-HB—O2 | | 18.0% by weight |
| 7-HEB—F | | 2.0% by weight |
| 3-HHEB—F | | 2.0% by weight |
| 5-HHEB—F | | 2.0% by weight |
| 3-HBEB—F | | 4.0% by weight |
| 2O1-HBEB(F)—C | | 2.0% by weight |
| 3-HB(F)EB(F)—C | | 2.0% by weight |
| 3-HBEB(F, F)—C | | 2.0% by weight |
| 3-HHB—F | | 4.0% by weight |
| 3-HHB—O1 | | 4.0% by weight |
| 3-HHB-3 | | 10.0% by weight |
| 3-HEBEB—F | | 2.0% by weight |
| 3-HEBEB-1 | | 2.0% by weight |
| Composition Example 23 | | |
| 5-HVHEB(F, F)—C | (No. 60) | 2.0% by weight |
| 2O1-BEB(F)—C | | 3.0% by weight |
| 3O1-BEB(F)—C | | 12.0% by weight |
| 5O1-BEB(F)—C | | 4.0% by weight |
| 1V2-BEB(F, F)—C | | 16.0% by weight |
| 3-HB—O2 | | 10.0% by weight |
| 3-HH-4 | | 3.0% by weight |
| 3-HHB—F | | 3.0% by weight |
| 3-HHB-1 | | 8.0% by weight |
| 3-HHB—O1 | | 4.0% by weight |
| 3-HBEB—F | | 4.0% by weight |
| 3-HHEB—F | | 7.0% by weight |
| 5-HHEB—F | | 7.0% by weight |
| 3-H2BTB-2 | | 4.0% by weight |
| 3-H2BTB-3 | | 4.0% by weight |
| 3-H2BTB-4 | | 4.0% by weight |
| 3-HB(F)TB-2 | | 5.0% by weight |
| Composition Example 24 | | |
| 3-HVB(F, F)EB(F, F)—C | (No. 23) | 10.0% by weight |
| 2-BEB—C | | 12.0% by weight |
| 3-BEB—C | | 4.0% by weight |
| 4-BEB—C | | 6.0% by weight |
| 3-HB—C | | 18.0% by weight |
| 3-HEB—O4 | | 12.0% by weight |

TABLE 1-continued

| | | |
|---|---|---|
| 4-HEB—O2 | | 8.0% by weight |
| 5-HEB—O1 | | 8.0% by weight |
| 3-HEB—O2 | | 6.0% by weight |
| 5-HEB—O2 | | 5.0% by weight |
| 3-HHB-1 | | 7.0% by weight |
| 3-HHB—O1 | | 4.0% by weight |
| Composition Example 25 | | |
| 5-HVHEB(F)—OCF3 | (No. 51) | 2.0% by weight |
| 5-HVHEB-5 | (No. 74) | 2.0% by weight |
| 2-BEB—C | | 10.0% by weight |
| 5-BB—C | | 10.0% by weight |
| 7-BB—C | | 7.0% by weight |
| 1-BTB-3 | | 7.0% by weight |
| 2-BTB-1 | | 10.0% by weight |
| 1O—BEB-2 | | 10.0% by weight |
| 1O—BEB-5 | | 12.0% by weight |
| 2-HHB-1 | | 4.0% by weight |
| 3-HHB—F | | 4.0% by weight |
| 3-HHB-1 | | 5.0% by weight |
| 3-HHB—O1 | | 4.0% by weight |
| 3-HHB-3 | | 13.0% by weight |
| Composition Example 26 | | |
| 5-HVHEB(F, F)—C | (No. 60) | 2.0% by weight |
| 5-HVHEB-5 | (No. 74) | 2.0% by weight |
| 2-HB—C | | 5.0% by weight |
| 3-HB—C | | 10.0% by weight |
| 3-HB—O2 | | 15.0% by weight |
| 2-BTB-1 | | 3.0% by weight |
| 3-HHB-1 | | 8.0% by weight |
| 3-HHB—F | | 4.0% by weight |
| 3-HHB—O1 | | 5.0% by weight |
| 3-HHB-3 | | 12.0% by weight |
| 3-HHEB—F | | 4.0% by weight |
| 5-HHEB—F | | 4.0% by weight |
| 2-HHB(F)—F | | 7.0% by weight |
| 3-HHB(F)—F | | 7.0% by weight |
| 5-HHB(F)—F | | 7.0% by weight |
| 3-HHB(F, F)—F | | 5.0% by weight |
| Composition Example 27 | | |
| 3-HVBEB(F, F)—C | (No. 1) | 10.0% by weight |
| 5-HVHEB(F, F)—C | (No. 60) | 3.0% by weight |
| 2-HHB(F)—F | | 17.0% by weight |
| 3-HHB(F)—F | | 17.0% by weight |
| 5-HHB(F)—F | | 16.0% by weight |
| 2-H2HB(F)—F | | 10.0% by weight |
| 3-H2HB(F)—F | | 5.0% by weight |
| 5-H2HB(F)—F | | 10.0% by weight |
| 2-HBB(F)—F | | 6.0% by weight |
| 3-HBB(F)—F | | 6.0% by weight |
| Composition Example 28 | | |
| 3-HVBEB(F, F)—C | (No. 1) | 8.0% by weight |
| 3-HVB(F, F)EB(F, F)—C | (No. 23) | 8.0% by weight |
| 7-HB(F, F)—F | | 3.0% by weight |
| 3-HB—O2 | | 7.0% by weight |
| 2-HHB(F)—F | | 10.0% by weight |
| 3-HHB(F)—F | | 10.0% by weight |
| 5-HHB(F)—F | | 10.0% by weight |
| 2-HBB(F)—F | | 9.0% by weight |
| 3-HBB(F)—F | | 9.0% by weight |
| 2-HBB—F | | 4.0% by weight |
| 3-HBB—F | | 4.0% by weight |
| 5-HBB—F | | 3.0% by weight |
| 3-HBB(F, F)—F | | 5.0% by weight |
| 5-HBB(F, F)—F | | 10.0% by weight |
| Composition Example 29 | | |
| 3-HVBEB(F, F)—C | (No. 1) | 6.0% by weight |
| 3-HB—CL | | 10.0% by weight |
| 5-HB—CL | | 4.0% by weight |
| 7-HB—CL | | 4.0% by weight |
| 1O1-HH-5 | | 5.0% by weight |
| 2-HBB(F)—F | | 8.0% by weight |
| 3-HBB(F)—F | | 8.0% by weight |
| 5-HBB(F)—F | | 8.0% by weight |
| 4-HHB—CL | | 8.0% by weight |

TABLE 1-continued

| | | |
|---|---|---|
| 5-HHB—CL | | 8.0% by weight |
| 3-H2HB(F)—CL | | 4.0% by weight |
| 3-HBB(F, F)—F | | 10.0% by weight |
| 5-H2BB(F, F)—F | | 9.0% by weight |
| 3-HB(F)VB-2 | | 4.0% by weight |
| 3-HB(F)VB-3 | | 4.0% by weight |
| Composition Example 30 | | |
| 5-HVHEB(F, F)—C | (No. 60) | 3.0% by weight |
| 3-HHB(F, F)—F | | 6.0% by weight |
| 3-H2HB(F, F)—F | | 8.0% by weight |
| 4-H2HB(F, F)—F | | 8.0% by weight |
| 5-H2HB(F, F)—F | | 8.0% by weight |
| 3-HBB(F, F)—F | | 21.0% by weight |
| 5-HBB(F, F)—F | | 20.0% by weight |
| 3-H2BB(F, F)—F | | 10.0% by weight |
| 5-HHBB(F, F)—F | | 3.0% by weight |
| 5-HHEBB—F | | 2.0% by weight |
| 3-HH2BB(F, F)—F | | 3.0% by weight |
| 1O1-HBBH-4 | | 4.0% by weight |
| 1O1-HBBH-5 | | 4.0% by weight |
| Composition Example 31 | | |
| 3-HVB(F, F)EB(F, F)—C | (No. 23) | 10.0% by weight |
| 5-HB—F | | 12.0% by weight |
| 6-HB—F | | 9.0% by weight |
| 7-HB—F | | 7.0% by weight |
| 2-HHB—OCF3 | | 7.0% by weight |
| 3-HHB—OCF3 | | 7.0% by weight |
| 4-HHB—OCF3 | | 7.0% by weight |
| 5-HHB—OCF3 | | 5.0% by weight |
| 3-HH2B—OCF3 | | 4.0% by weight |
| 5-HH2B—OCF3 | | 4.0% by weight |
| 3-HHB(F, F)—OCF3 | | 5.0% by weight |
| 3-HBB(F)—F | | 10.0% by weight |
| 3-HH2B(F)—F | | 3.0% by weight |
| 3-HB(F)BH-3 | | 3.0% by weight |
| 5-HBBH-3 | | 3.0% by weight |
| 3-HHB(F, F)—OCF2H | | 4.0% by weight |
| Composition Example 32 | | |
| 5-HVHEB(F, F)—C | (No. 60) | 3.0% by weight |
| 3-BEB(F)—C | | 8.0% by weight |
| 3-HB—C | | 5.0% by weight |
| V—HB—C | | 8.0% by weight |
| 1V—HB—C | | 8.0% by weight |
| 3-HH-2 | | 3.0% by weight |
| 3-HH-2V | | 14.0% by weight |
| 3-HH-2V1 | | 7.0% by weight |
| V2-HHB-1 | | 15.0% by weight |
| 3-HHB-1 | | 5.0% by weight |
| 3-HHEB—F | | 7.0% by weight |
| 3-H2BTB-2 | | 6.0% by weight |
| 3-H2BTB-3 | | 6.0% by weight |
| 3-H2BTB-4 | | 5.0% by weight |
| Composition Example 33 | | |
| 5-HVHEB-5 | (No. 74) | 5.0% by weight |
| 3-H2HB(F, F)—F | | 7.0% by weight |
| 5-H2HB(F, F)—F | | 8.0% by weight |
| 3-HHB(F, F)—F | | 10.0% by weight |
| 3-HH2B(F, F)—F | | 9.0% by weight |
| 5-HH2B(F, F)—F | | 9.0% by weight |
| 3-HBB(F, F)—F | | 15.0% by weight |
| 5-HBB(F, F)—F | | 15.0% by weight |
| 3-HBEB(F, F)—F | | 2.0% by weight |
| 4-HBEB(F, F)—F | | 2.0% by weight |
| 5-HBEB(F, F)—F | | 2.0% by weight |
| 3-HHEB(F, F)—F | | 10.0% by weight |
| 4-HHEB(F, F)—F | | 3.0% by weight |
| 5-HHEB(F, F)—F | | 3.0% by weight |

BEST MODE FOR CARRYING OUT THE INVENTION

Now, the present invention will be described in more detail with reference to Examples. In each of the Examples, Cr indicates crystal; $S_A$, smectic phase A; $S_B$, smectic phase B; $S_x$, smectic phase structure of which has not yet be analyzed; N, nematic phase; and Iso, isotropic phase, and the unit of all phase transition temperatures is ° C.

EXAMPLE 1

Preparation of (E)-3,5-difluoro-4-cyanophenyl 4-(2-(trans-4-propylcyclohexyl)vinyl)benzoate (Compound expressed by the general formula (1) wherein Ra is $C_3H_7$, Rb is cyano group, m is 0, $A_1$ is trans-1,4-cyclohexylene group, $A_2$ is 1,4-phenylene group, $A_3$ is 3,5-difluoro-1,4-phenylene group, $Z_1$ is —CH=CH—, and $Z_2$ is —COO—; Compound No. 1)

First Step

Preparation of (E)-4-(2-(trans-4-propylcyclohexyl)vinyl) benzoic acid

To a mixture of 25.0 g (0.11 mol) of trans-4-propylcyclohexylmethyltriphenylphosphonium bromide and 100 ml of tetrahydrofuran (THF) was added 12.2 g (0.10 mol) of t-BuOK while maintaining a temperature of lower than −20° C., and stirred for 1 hour. Subsequently, 70 ml of solution of 12.9 g (0.10 mol) of 4-cyanobenzaldehyde in THF was added dropwise to the solution while maintaining a temperature of lower than −20° C., and stirred at the same temperature for 2 hours to react. After finishing of the reaction, 50 ml of water was added to the reaction product and then extracted with 100 ml of toluene. The organic layer thus obtained was washed with water thrice and then dried over anhydrous magnesium sulfate. The solvent was distilled off under a reduced pressure, and the residue was subjected to silica gel column chromatography (eluent: toluene) to obtain 12.1 g of a crude 4-(2-(trans-4-propylcyclohexyl)vinyl)benzonitrile.

This nitrile in an amount of 11.7 g (0.05 ml) was added to a mixture of 13.9 g (0.07 ml) of dihydrated sodium benzenesufinate, 12 ml of 6N-HCl, and 70 ml of ethanol, and reacted under reflux for 4 hours. After finishing of the reaction, 50 ml of water was added to the reaction product and then extracted with 150 ml of toluene. The organic layer thus obtained was washed with saturated aqueous sodium carbonate solution thrice and with water thrice, and then dried over anhydrous magnesium sulfate. The solvent was distilled off under a reduced pressure, and the residue was subjected to silica gel column chromatography (eluent: toluene) to obtain 12.0 g of a crude (E)-4-(2-(trans-4-propylcyclohexyl)vinyl)benzonitrile.

This crude product in an amount of 10.0 g (0.04 mol) was added to a mixture of 11.1 g (0.20 mol) of potassium hydroxide, 40 ml of water, and 250 ml of ethylene glycol, and reacted while being stirred at 140° C. for 25 hours. After finishing of the reaction, the reaction product was poured into 600 ml of 6N-HCL, and then extracted with 500 ml of diethyl ether twice. The organic layer thus obtained was washed with water five times and then dried over anhydrous magnesium sulfate. The solvent was distilled off under a reduced pressure, and the residue was recrystallized from a mixed solvent of toluene/heptane to obtain 5.7 g of (E)-4-(2-(trans-4-propylcyclohexyl)vinyl)benzoic acid (yield 53.4%).

Second Step

This product in an amount of 1.6 g (5.9 mmol) was mixed with 1.0 g (6.2 mmol) of 3,5-difluoro-4-cyanophenol, 0.2 g (1.8 mmol) of DMAP, and 25 ml of dichloromethane. To this mixture was added dropwise 7 ml of solution of 1.6 g (7.6 mmol) of DCC in dichloromethane while being cooled with ice in 5 min, stirred as it was for 12 hours, and then separated crystals were filtered off.

To the filtrate thus obtained was added 50 ml of toluene. This solution was washed with 2N-NaOH five times and with water thrice, and then dried over anhydrous magnesium sulfate. The solvent was distilled off under a reduced pressure, and the residue thus obtained was subjected to silica gel column chromatography (eluent: toluene) to obtain 2.0 g of a crude (E)-3,5-difluoro-4-cyanophenyl 4-(2-(trans-4-propylcyclohexyl)vinyl)benzoate. This crude product was recrystallized from a mixed solvent of heptane/diethyl ether to obtain 1.3 g of the subjective compound (yield 57.1%).

This compound exhibited liquid crystal phase and its phase transition temperatures were as follows:

C 76.9~78.1 N 210.8~210.9 Iso

Further, mass spectrum data of this compound well supported its structure.

Mass spectrometry: 409 ($M^+$); $H^1$NMR ($CDCl_3$, TMS internal standard); δ (ppm); 0.89–1.89 (m, 17H); 6.47 (m, 2H); 7.05 (brd, 2H); 7.46 (d, 2H); 8.06 (d, 2H).

This compound (Compound No. 1) is similar to Compound (a) described in the Laid-open Japanese Patent Publication No. Hei 4-279560 mentioned above in their structure since Compound No. 1 is the same as Compound (a) with the exception that the covalent bond of bonding group is replaced by alkenylene group. However, they are considerably different in their properties (phase transition temperatures).

That is, whereas the phase transition temperatures of Compound No. 1 were as described above, those of Compound (a) are C 89.8 N 140.9 Iso (cf. Laid-open Japanese Patent Publication No. Hei 4-279560), and it can be understood that the former is wider in temperature range of liquid crystal phase by about 80° C. and higher in NI about 70° C. than the latter.

According the methods of Example 1, the following compounds (Compounds No. 2 to No. 50) are prepared:

| No. |
| --- |
| 2 |

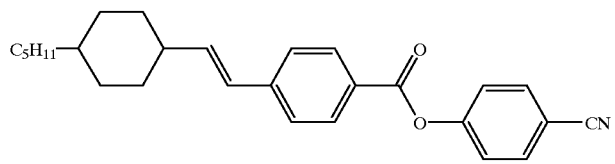

-continued
| No. | |
|---|---|
| 3 | 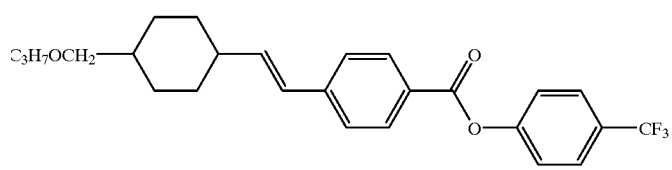 |
| 4 | 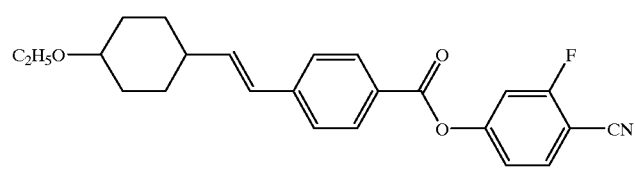 |
| 5 | 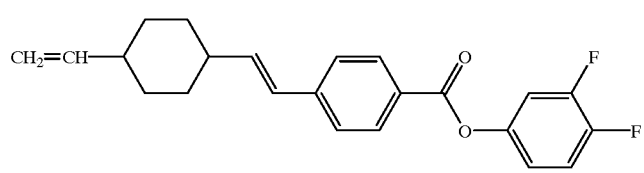 |
| 6 | 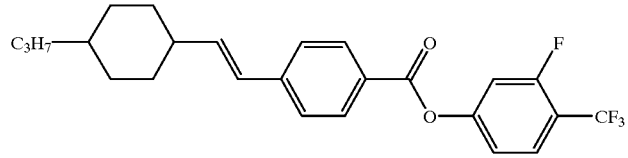 |
| 7 | 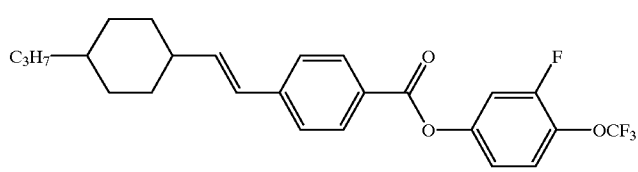 |
| 8 | 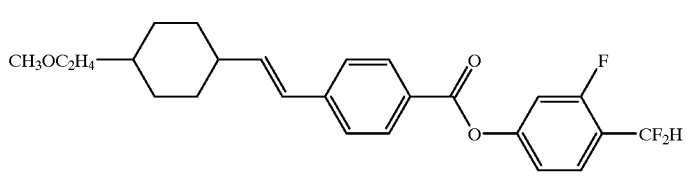 |
| 9 | 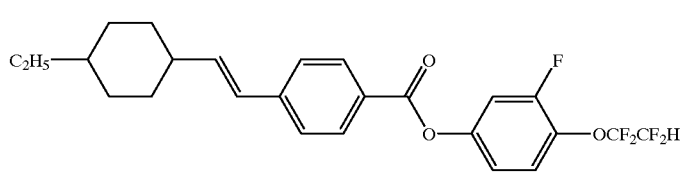 |
| 10 | 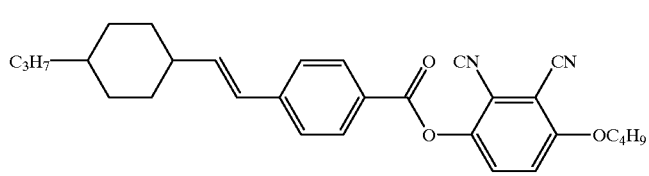 |

-continued
| No. | |
|---|---|
| 11 | 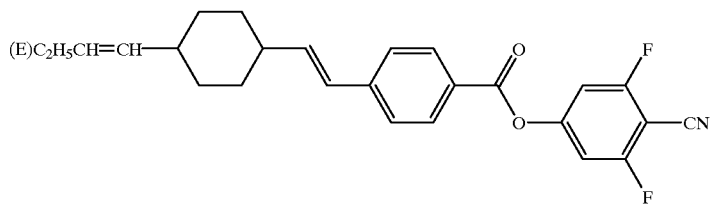 |
| 12 | 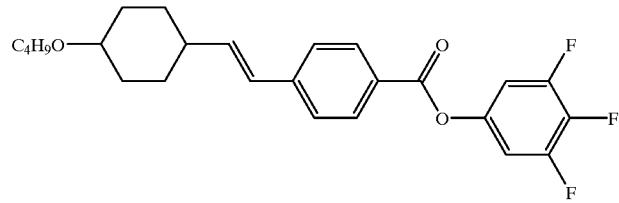 |
| 13 | 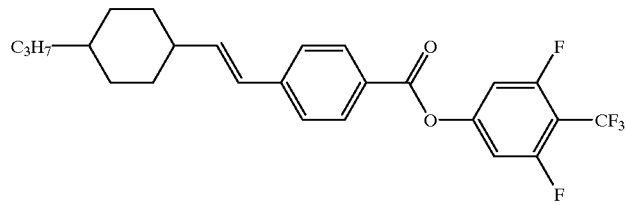 |
| 14 | 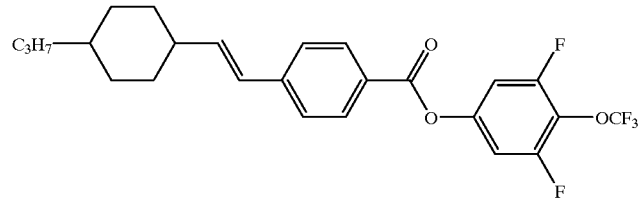 |
| 15 | 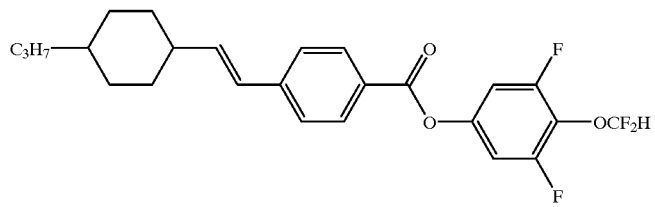 |
| 16 | 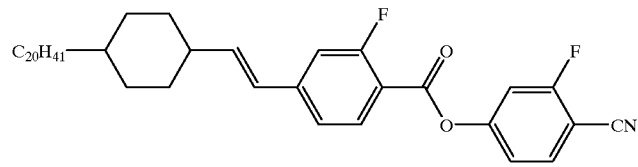 |
| 17 | 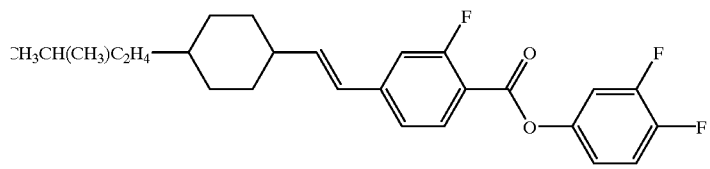 |

| No. | | |
|---|---|---|
| 18 | 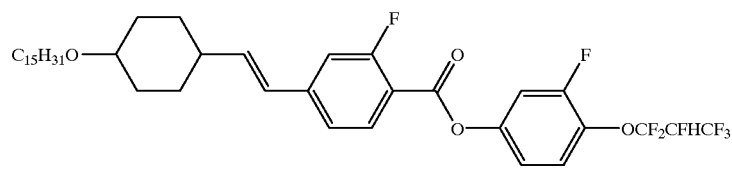 | |
| 19 | 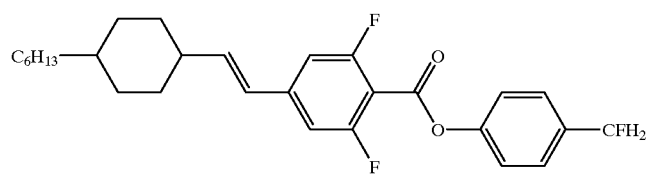 | |
| 20 | 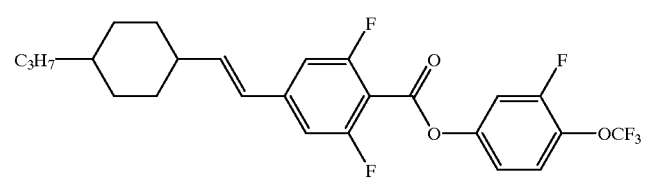 | |
| 21 | 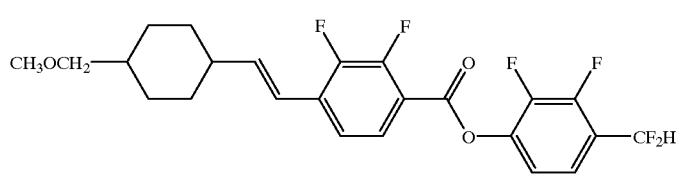 | |
| 22 | 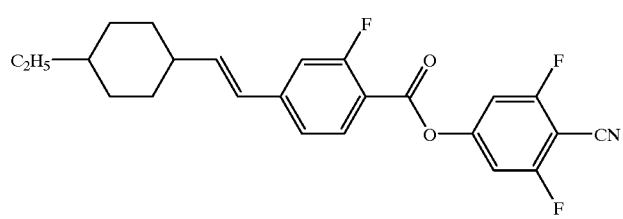 | |
| 23 | 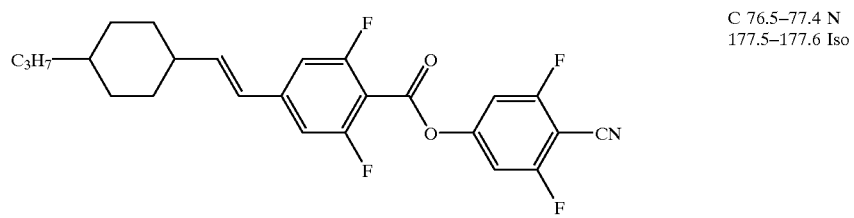 | C 76.5–77.4 N 177.5–177.6 Iso |
| 24 | 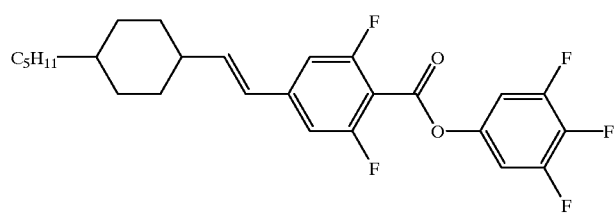 | |

-continued
| No. | |
|---|---|
| 25 | 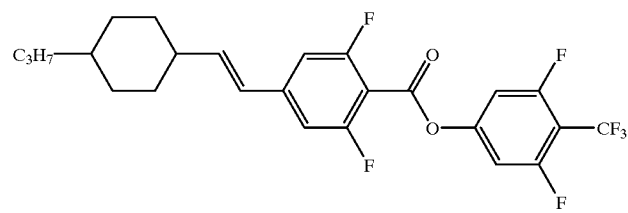 |
| 26 | 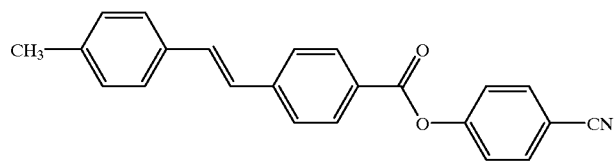 |
| 27 | 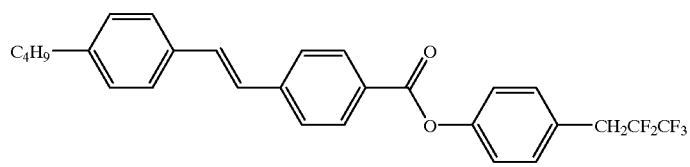 |
| 28 | 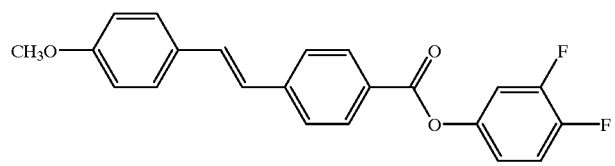 |
| 29 | 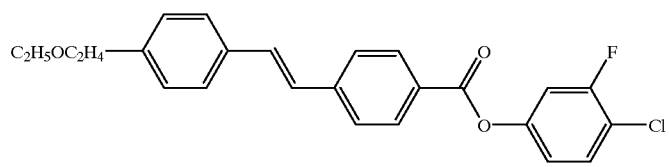 |
| 30 | 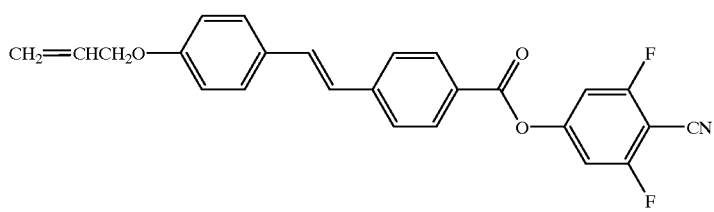 |
| 31 | 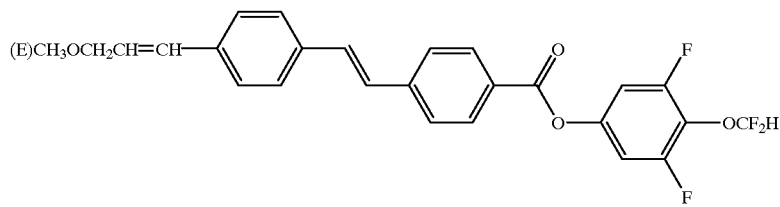 |
| 32 | 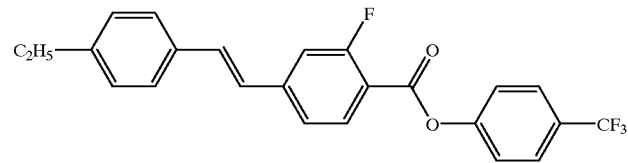 |

| No. | |
|---|---|
| 33 | 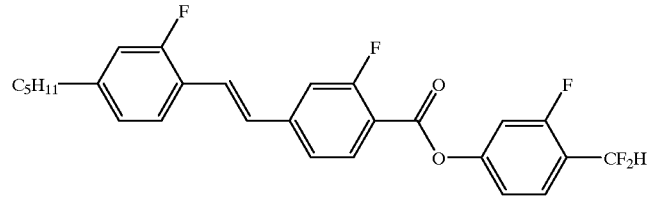 |
| 34 | 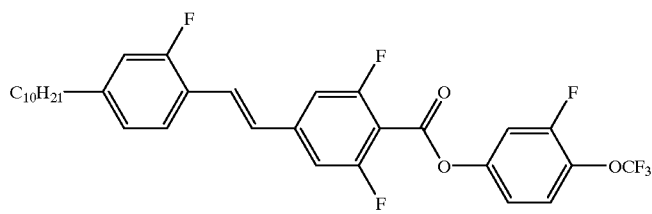 |
| 35 | 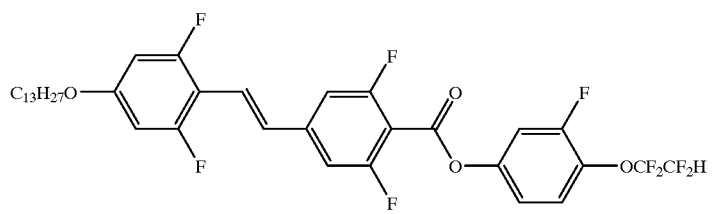 |
| 36 | 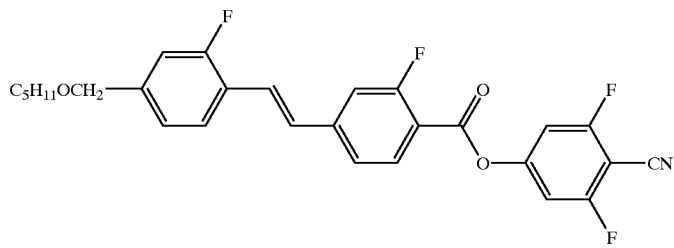 |
| 37 | 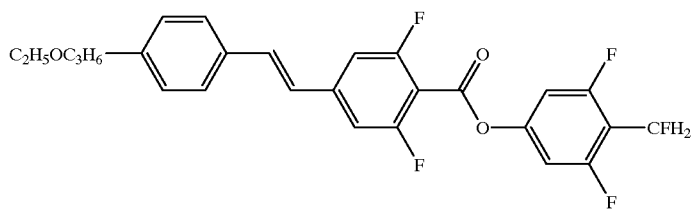 |
| 38 | 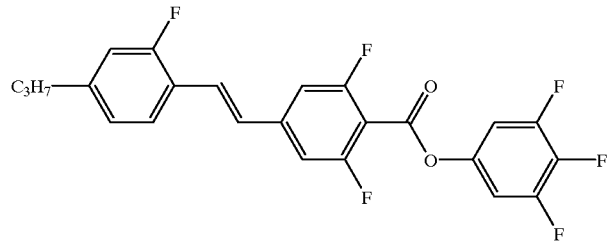 |

-continued
| No. | |
|---|---|
| 39 | 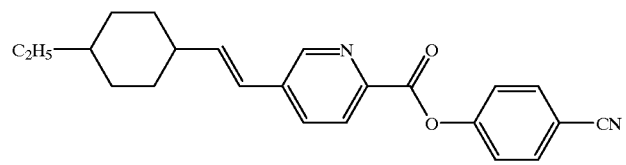 |
| 40 | 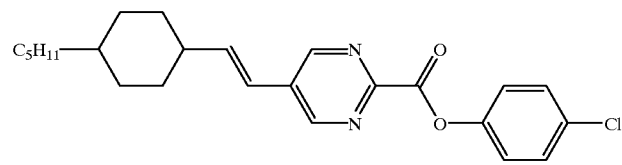 |
| 41 | 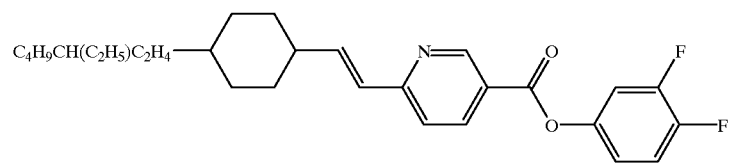 |
| 42 | 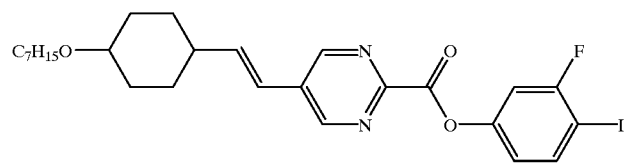 |
| 43 | 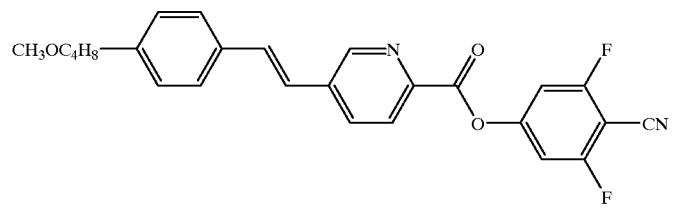 |
| 44 | 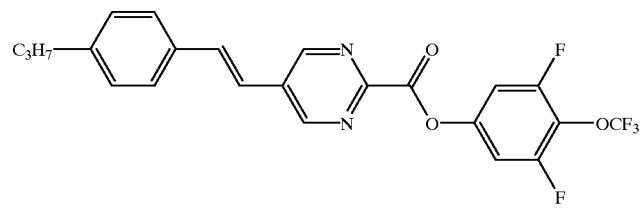 |
| 45 | 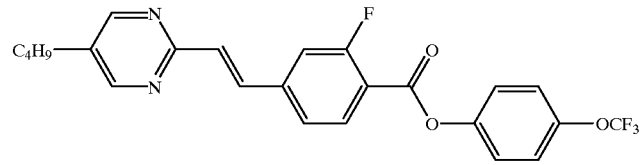 |

-continued

| No. | |
|---|---|
| 46 | 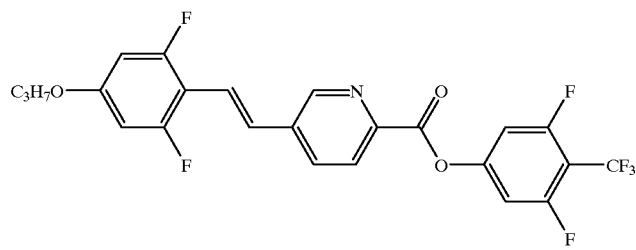 |
| 47 | 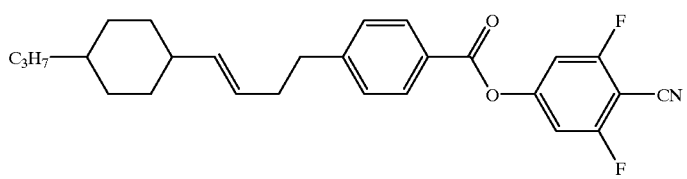 |
| 48 | 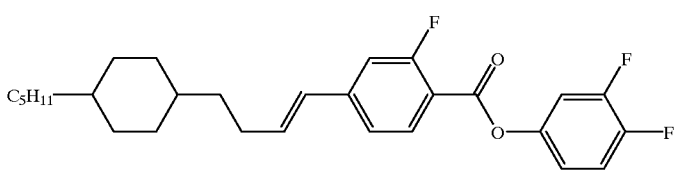 |
| 49 | 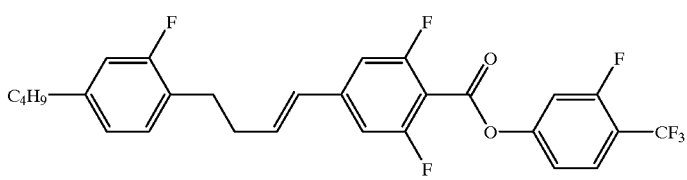 |
| 50 | 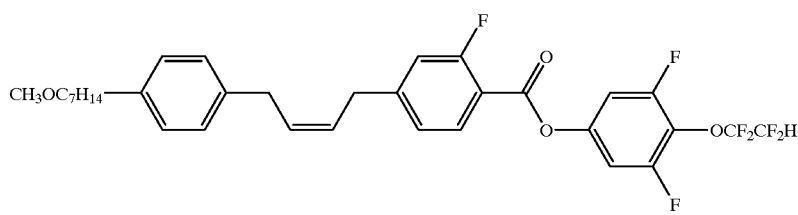 |

EXAMPLE 2

Preparation of (E)-3-fluoro-4-trifluoromethoxyphenyl trans-4-(2-(trans-4-pentylcyclohexyl)vinyl) cyclohexanecarboxylate (Compound expressed by the general formula (1) wherein Ra is $C_5H_{11}$, Rb is $OCF_3$, m is 0, both $A_1$ and $A_2$ are trans-1,4-cyclohexylene group, $A_3$ is 3-fluoro-1,4-phenylene group, $Z_1$ is —CH=CH—, and $Z_2$ is —COO—; Compound No. 51)

The (E)-trans-4-(2-(trans-4-pentylcyclohexyl)vinyl) cyclohexanecarboxylic acid, which was prepared by the same manner as in the first step of Example 1 with the exception that ethyl trans-4-formylcyclohexanecarboxylate was used in place of 4-cyanobenzaldehyde, in an amount of 1.1 g (3.6 mmol) was mixed with 0.8 g (3.9 mmol) of 3-fluoro-4-trifluromethoxyphenol, 0.1 g (1.1 mmol) of DMAP, and 20 ml of dichloromethane. To this mixture was added dropwise 4 ml of solution of 1.0 g (4.7 mmol) of DCC in dichloromethane while being cooled with ice in 5 min, and stirred as it was for 12 hours. Separated crystals were filtered off, 70 ml of toluene was added to the filtrate, and the filtrate was washed with 2N-NaOH five times and with water thrice, and then dried over anhydrous magnesium sulfate. The solvent was distilled off under a reduced pressure. The residue thus obtained was subjected to silica gel column chromatography (eluent:toluene) to obtain 1.7 g of a crude (E)-3-fluoro-4-trifluoromethoxyphenyl trans-4-(2-(trans-4-pentylcyclohexyl)vinyl)cyclohexanecarboxylate. This crude product was recrystallized from a mixed solvent of heptane/diethyl ether to obtain 0.7 g of the subjective compound (yield 38.7%).

This compound exhibited liquid crystal phase and its phase transition temperatures were as follows:

C 78.3~78.9 N 161.8~161.9 Iso

Further, mass spectrum data of this compound well supported its structure.

Mass spectrometry: 484 ($M^+$); $H^1$NMR ($CDCl_3$, TMS internal standard); δ (ppm); 0.88–2.47 (m, 31H); 5.33 (m, 2H); 6.85–7.40 (m, 3H).

According the methods of Example 2, the following compounds (Compounds No. 52 to No. 73) are prepared.
| No. | |
|---|---|
| 52 | 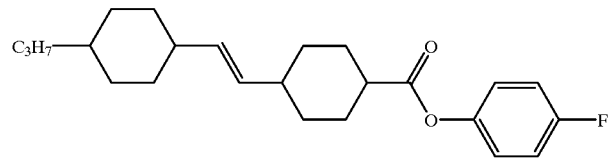 |
| 53 | 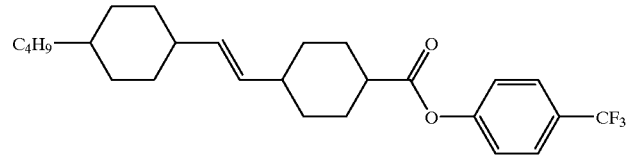 |
| 54 | 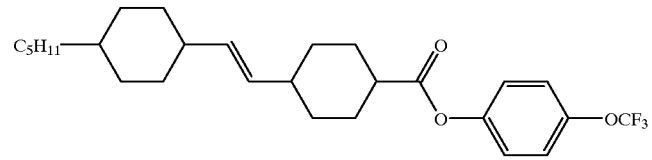 |
| 55 | 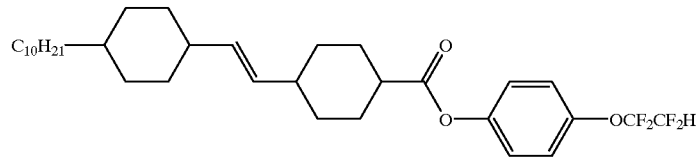 |
| 56 | 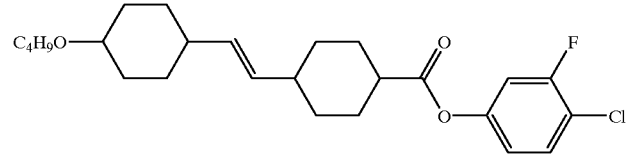 |
| 57 | 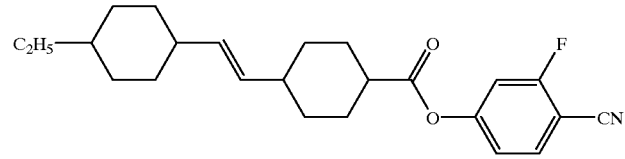 |
| 58 | 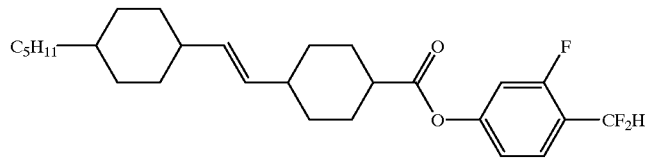 |
| 59 | 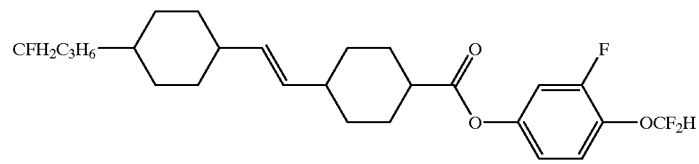 |

| No. | | |
|---|---|---|
| 60 | 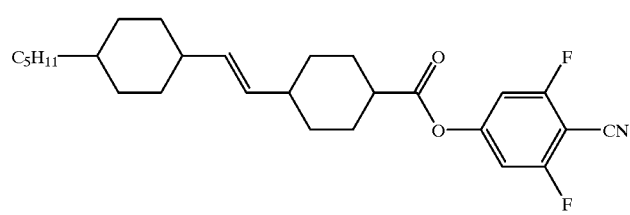 | C 81.6–82.1 N 166.5–166.6 Iso |
| 61 | 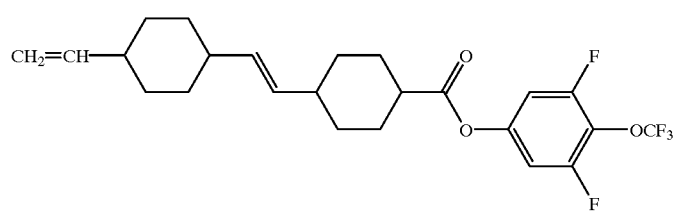 | |
| 62 | 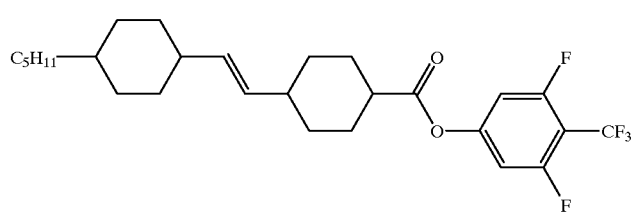 | |
| 63 | 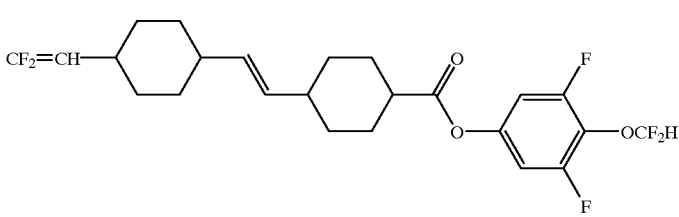 | |
| 64 | 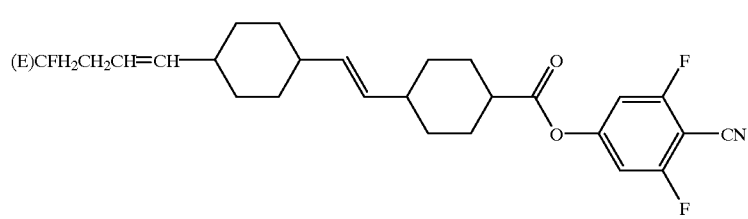 | |
| 65 | 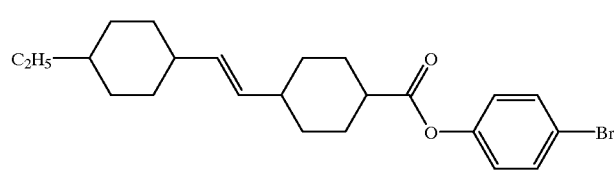 | |
| 66 | 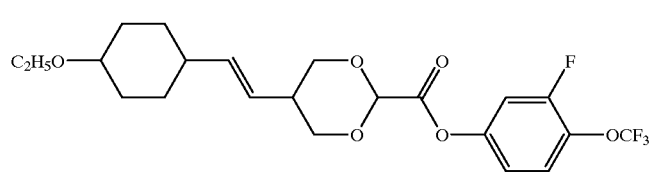 | |

-continued

| No. | |
|---|---|
| 67 | 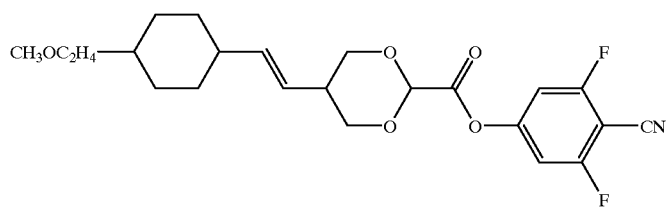 |
| 68 | 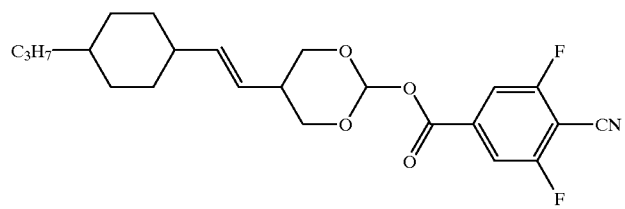 |
| 69 | 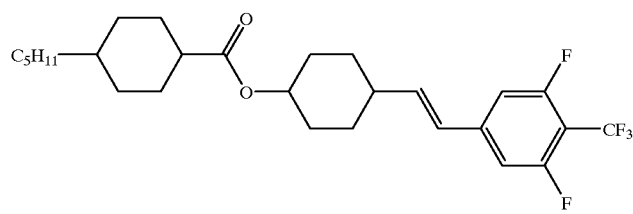 |
| 70 | 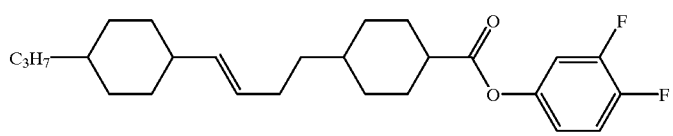 |
| 71 | 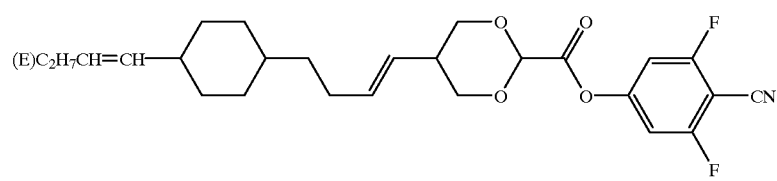 |
| 72 | 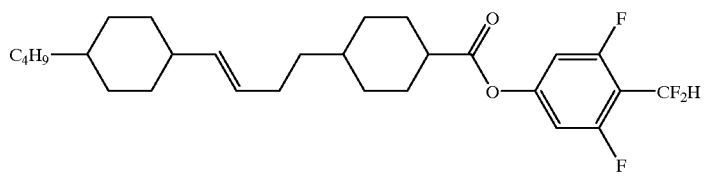 |
| 73 | 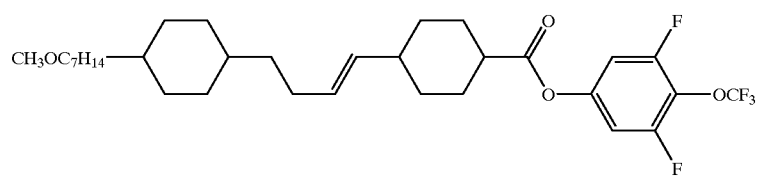 |

EXAMPLE 3

Preparation of (E)-4-pentylphenyl trans 4-(2-(trans-4-pentylcyclohexyl)vinyl)cyclohexanecarboxylate (Compound expressed by the general formula (1) wherein both Ra and Rb are $C_5H_{11}$, m is 0, both $A_1$ and $A_2$ are trans-1,4-cyclohexylene group, $A_3$ is 1,4-phenylene group, $Z_1$ is —CH=CH—, and $Z_2$ is —COO—; Compound No. 74)

(E)-trans-4-(2-(trans-4-pentylcyclohexyl)vinyl) cyclohexane carboxylic acid in an amount of 1.1 g (3.6 mmol), 0.7 g (4.3 mmol) of 4-pentylphenol, 0.1 g (1.1 mmol) of DMAP, and 20 ml of dichloromethane were mixed. To this mixture was added dropwise 4 ml of solution of 1.0 g (4.7 mmol) of DCC in dichloromethane while being cooled with ice in 5 min, and stirred as it was for 12 hours. Separated crystals were filtered off. To the filtrate was added 70 ml of toluene, washed with 2N-NaOH five times and with water thrice, and then dried over anhydrous magnesium sulfate. The solvent was distilled off under a reduced pressure. The residue thus obtained was subjected to silica gel column chromatography (eluent: toluene/heptane=1/1) to obtain 1.5 g of a crude (E)-4-pentylphenyl trans-4-(2-(trans-4-pentylcyclohexyl)vinyl)cyclohexanecarboxylate. This crude product was recrystallized from a mixed solvent of heptane/diethyl ether to obtain 1.2 g of the subjective compound (yield 74.7%).

This compound exhibited liquid crystal phase and its phase transition temperatures were as follows:

C 66.7~67.6 $S_A$ 157.0 N 183.7 Iso

Further, mass spectrum data of this compound well supported its structure.

Mass spectrometry: 452 (M$^+$); H$^1$NMR (CDCl$_3$, TMS internal standard); δ (ppm); 0.81–2.67 (m, 41H); 5.30–5.35 (m,2H); 6.94 (m, 2H); 7.17 (d, 2H).

According the methods of Example 3, the following compounds (Compounds No. 75 to No. 108) are prepared.

| No. |  |
|---|---|
| 75 | 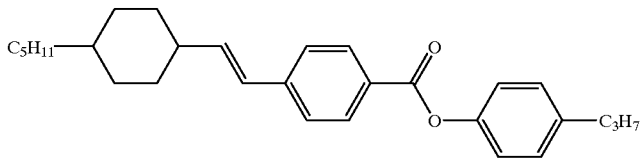 |
| 76 | 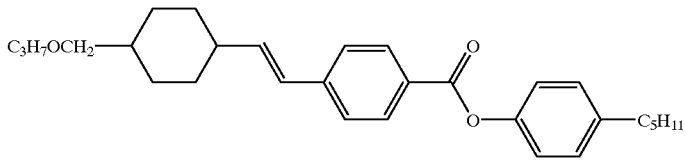 |
| 77 | 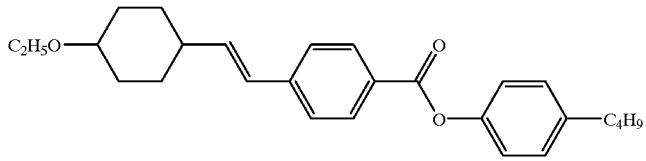 |
| 78 | 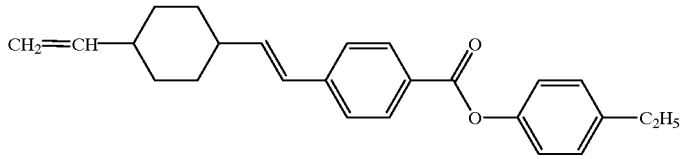 |
| 79 | 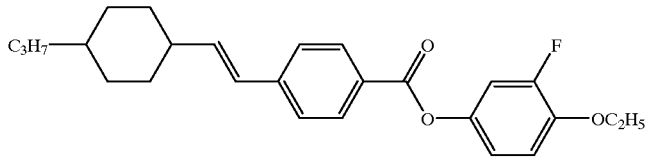 |
| 80 | 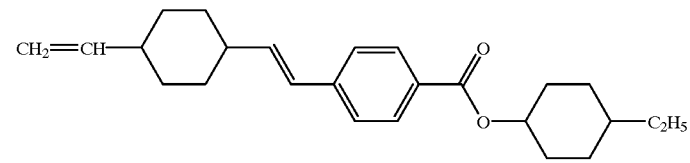 |

-continued
| No. | |
|---|---|
| 81 | 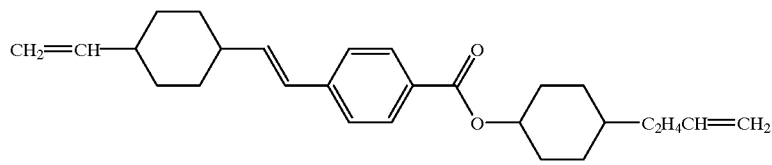 |
| 82 | 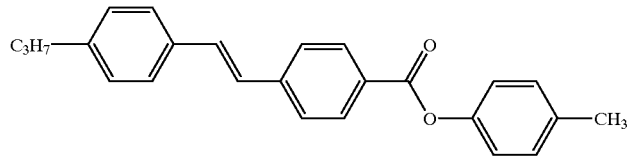 |
| 83 | 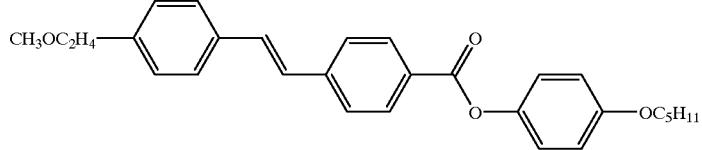 |
| 84 | 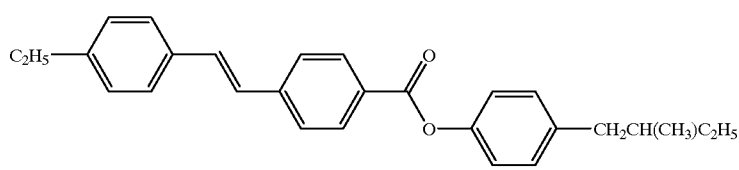 |
| 85 | 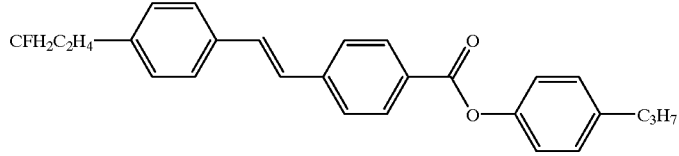 |
| 86 | 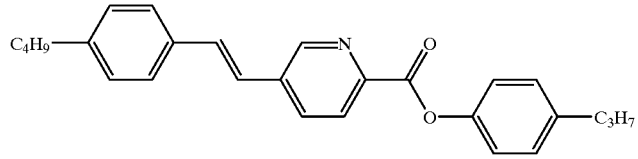 |
| 87 | 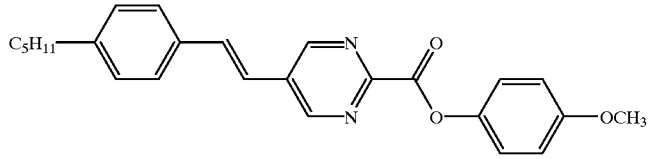 |
| 88 | 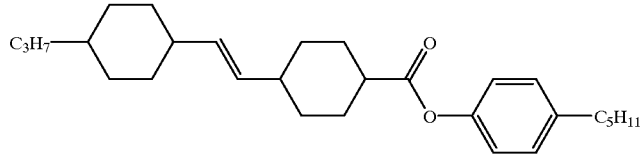 |

-continued
| No. | |
|---|---|
| 89 | 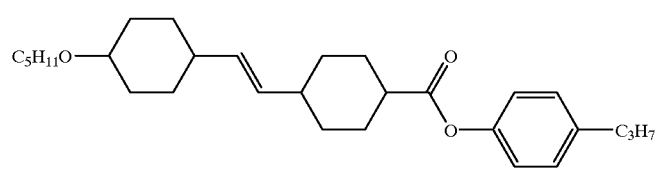 |
| 90 | 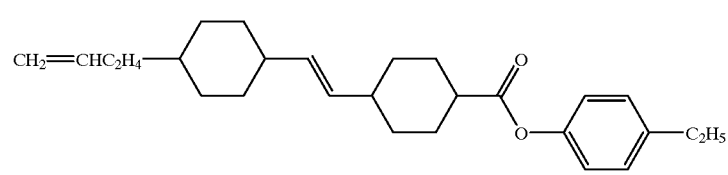 |
| 91 | 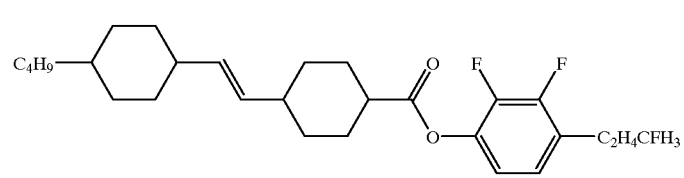 |
| 92 | 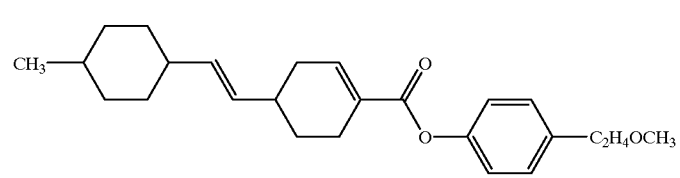 |
| 93 | 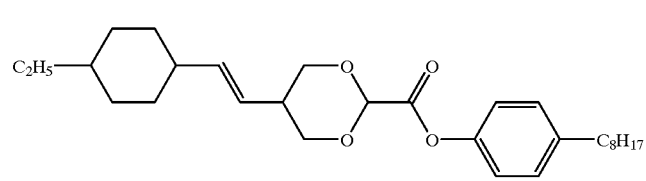 |
| 94 | 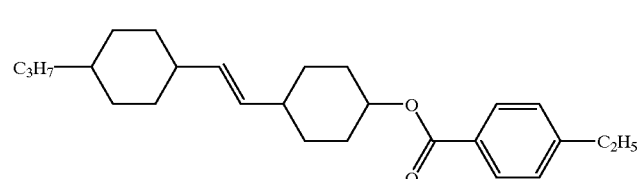 |
| 95 | 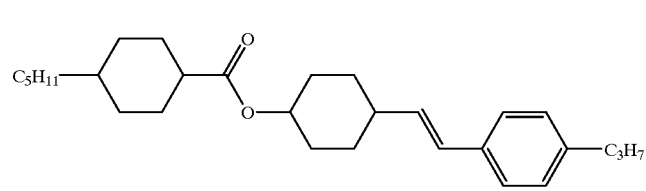 |
| 96 | 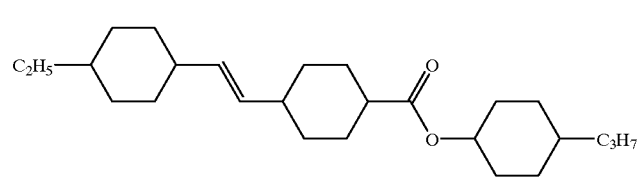 |

-continued
| No. | |
|---|---|
| 97 | 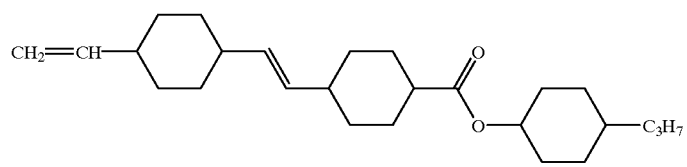 |
| 98 | 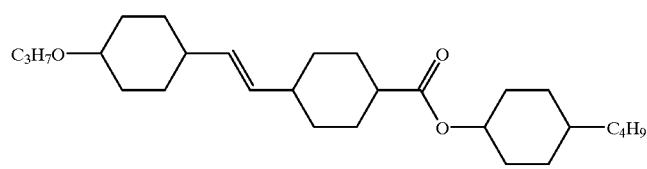 |
| 99 | 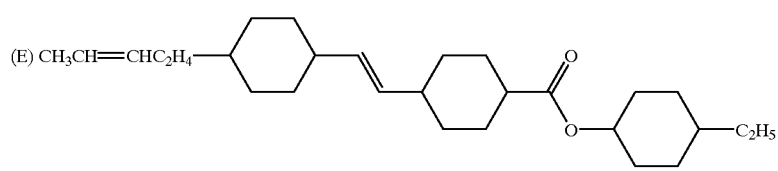 |
| 100 | 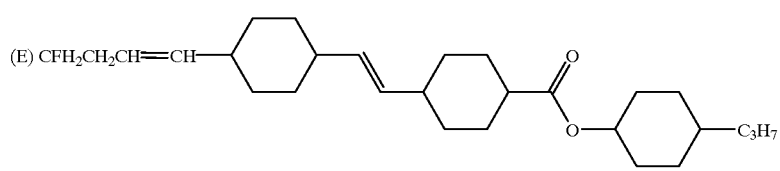 |
| 101 | 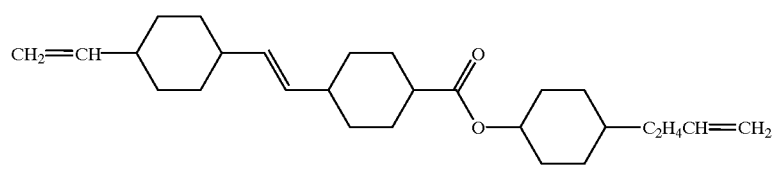 |
| 102 | 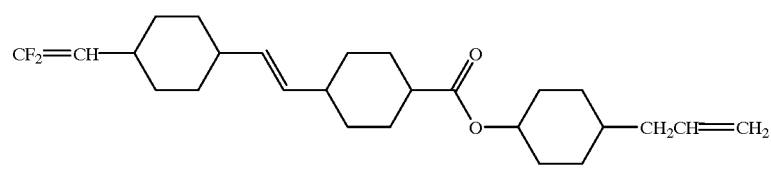 |
| 103 | 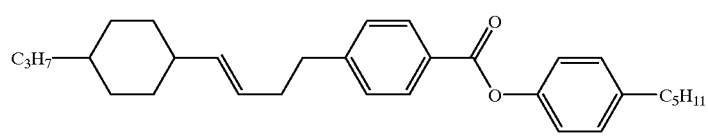 |
| 104 | 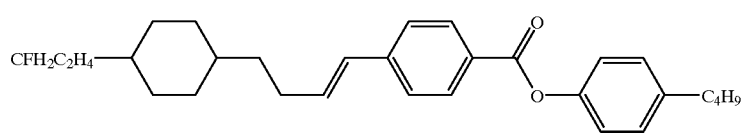 |
| 105 | 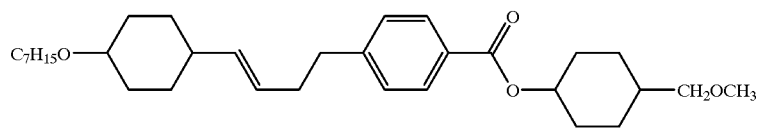 |

-continued

| No. | |
|---|---|
| 106 | 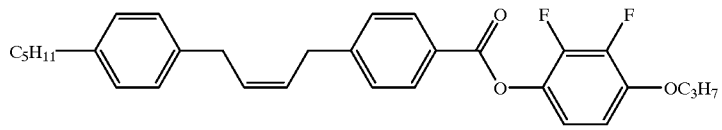 |
| 107 | 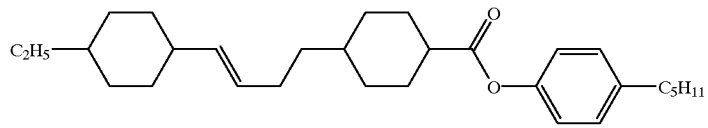 |
| 108 | 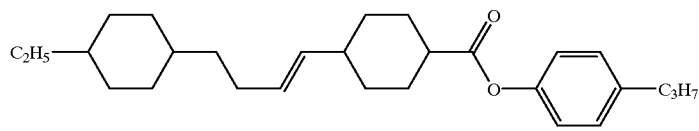 |

EXAMPLE 4

Preparation of (E)-3,5-difluoro-4-trifluoromethoxyphenyl 4-(2-(trans-4-(trans-4-propylcyclohexyl)cyclohexyl)vinyl) benzoate (Compound expressed by the general formula (1) wherein Ra is $C_3H_7$, Rb is $OCF_3$, m is 1, both $A_1$ and $A_2$ are trans-1,4-cyclohexylene group, $A_3$ is 1,4-phenylene group, $A_4$ is 3-fluoro-1,4-phenylene group, $Z_1$ is a covalent bond, $Z_2$ is —CH=CH—, and $Z_3$ is —COO—; Compound No. 109)

(E)-4-(2-(trans-4-(trans-4-pentylcyclohexyl)cyclohexyl)vinyl)benzoic acid in an amount of 1,3 g (3.7 mmol), 0.8 g (3.7 mmol) of 3,5-difluoro-4-trifluoromethoxyphenol, 0.1 g (1.1 mmol) of DMAP, and 30 ml of dichloromethane were mixed. To this mixture was added dropwise 5 ml of solution of 1.0 g (4.8 mmol) of DCC in dichloromethane while being cooled with ice in 5 min, and stirred as it was for 12 hours. Separated crystals were filtered off, and 80 ml of toluene was added to the filtrate, washed with 2N-NaOH five times and with water thrice, and then dried over anhydrous magnesium sulfate. The solvent was distilled off under a reduced pressure. The residue thus obtained was subjected to silica gel column chromatography (eluent: toluene) to obtain 1.7 g of a crude (E)-3,5-difluoro-4-trifluoromethoxyphenyl 4-(2-(trans-4-(trans-4-propylcyclohexyl)cyclohexyl)vinyl) benzoate.

This crude product was recrystallized from a mixed solvent of heptane/ethyl acetate to obtain 1.5 g of the subjective compound (yield 74.3%).

Mass spectrum data of this compound well supported its structure.

Mass spectrometry: 550 ($M^+$).

According the methods of Example 4, the following compounds (Compounds No. 110 to No. 149) are prepared.

| No. | |
|---|---|
| 110 | 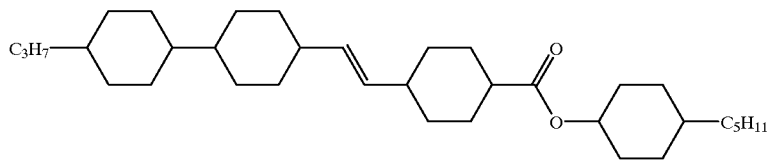 |
| 111 | 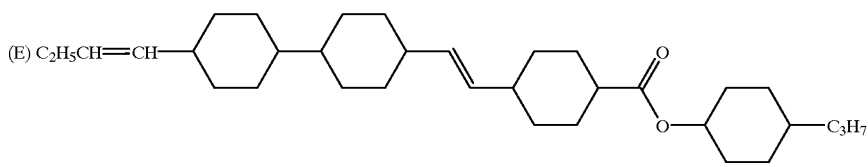 |

-continued
| No. | |
|---|---|
| 112 | 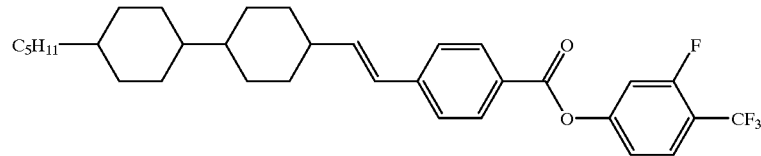 |
| 113 | 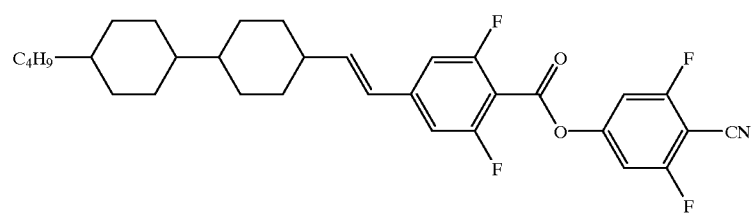 |
| 114 | 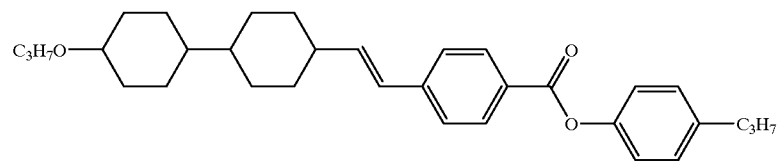 |
| 115 | 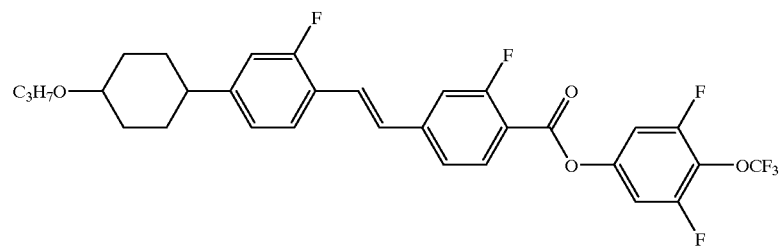 |
| 116 | 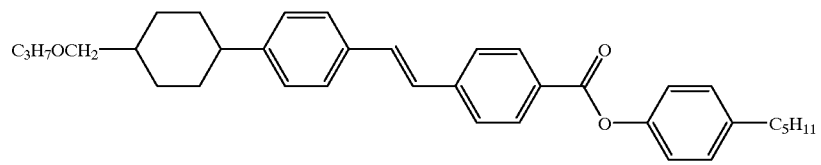 |
| 117 | 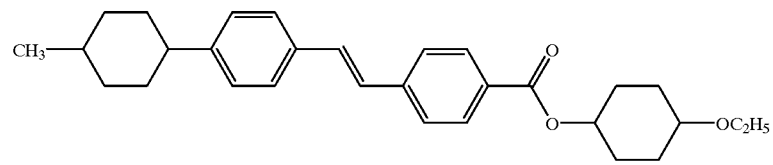 |
| 118 | 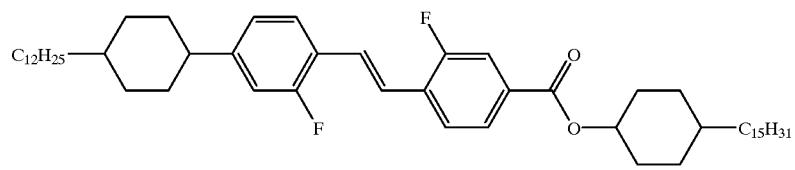 |
| 119 | 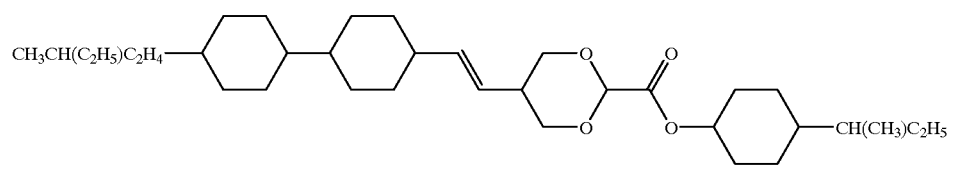 |

-continued
| No. | |
|---|---|
| 120 | 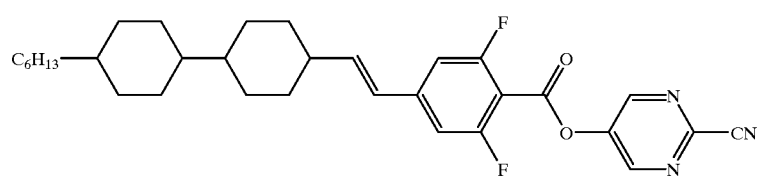 |
| 121 | 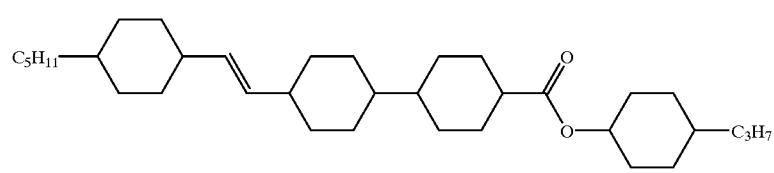 |
| 122 | 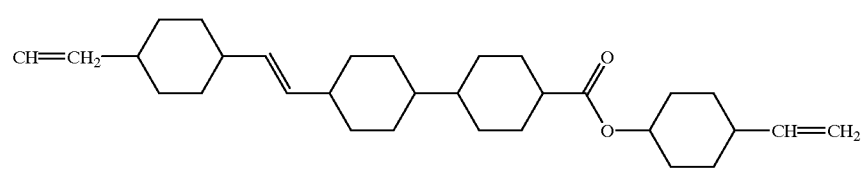 |
| 123 | 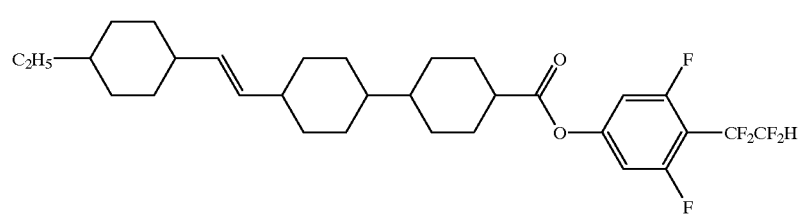 |
| 124 | 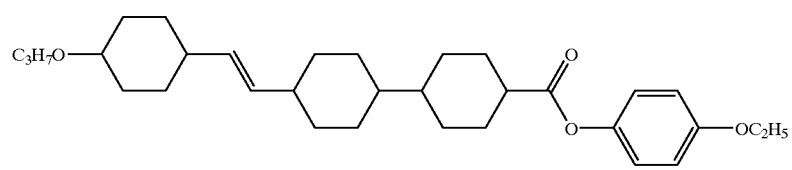 |
| 125 | 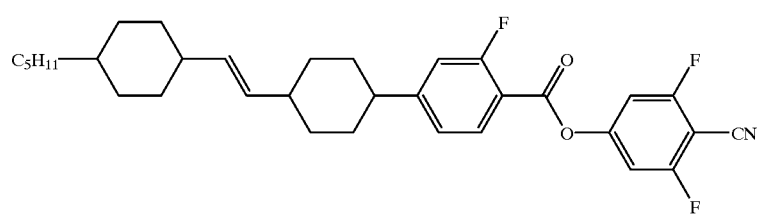 |
| 126 | 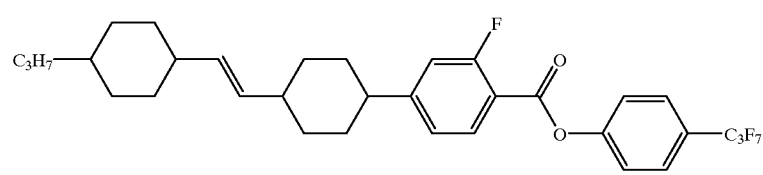 |
| 127 | 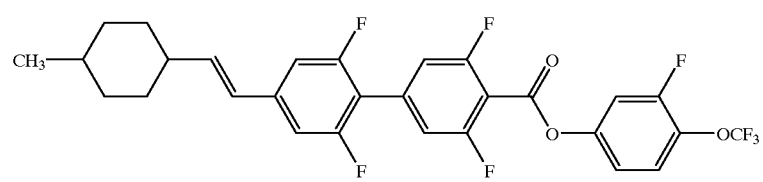 |

| No. | |
|---|---|
| 128 | 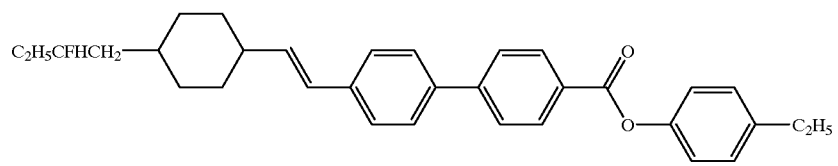 |
| 129 | 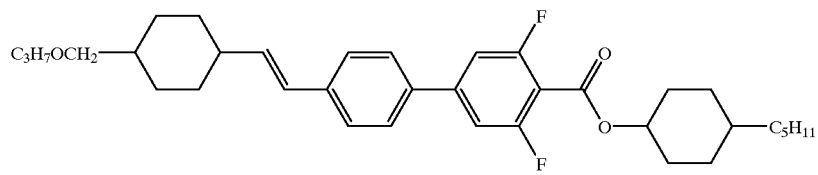 |
| 130 | 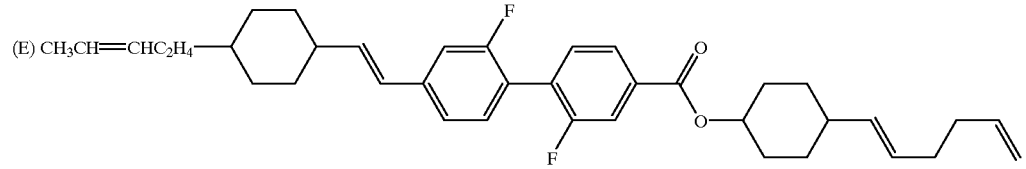 |
| 131 | 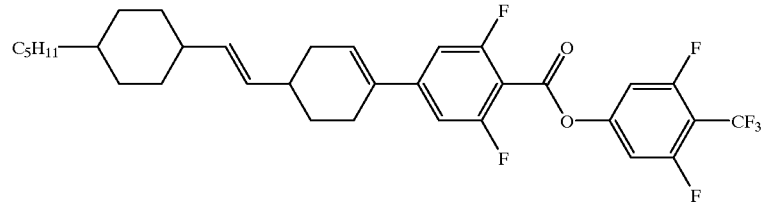 |
| 132 | 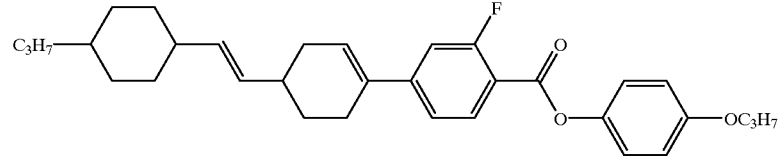 |
| 133 | 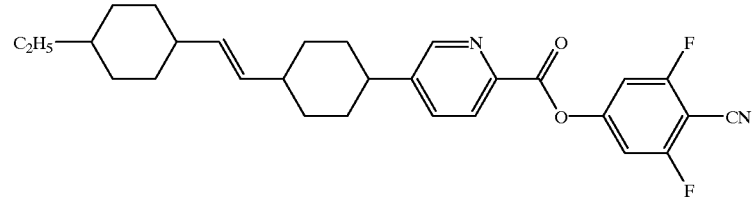 |
| 134 | 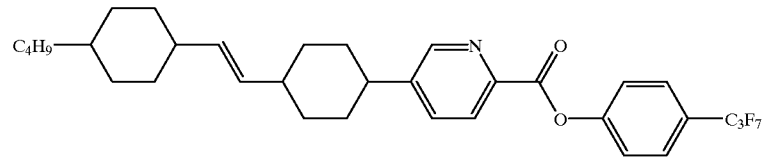 |
| 135 | 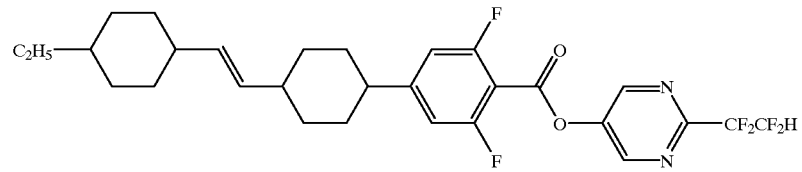 |

-continued
| No. | |
|---|---|
| 136 | 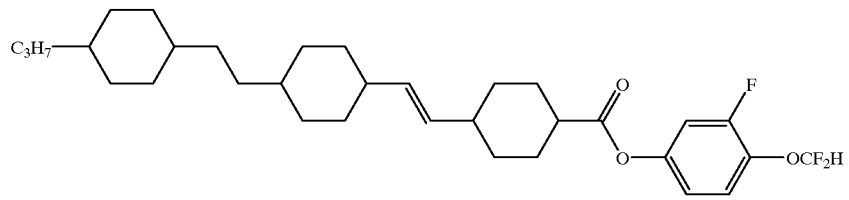 |
| 137 | 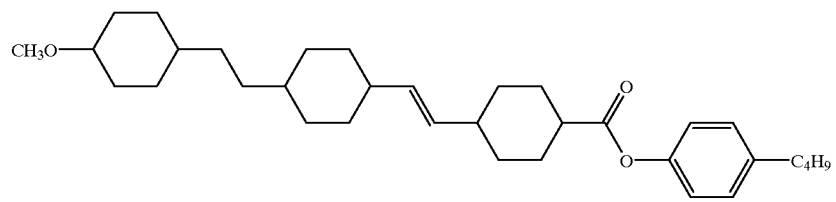 |
| 138 | 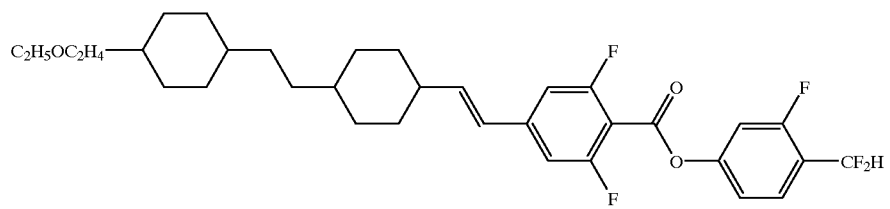 |
| 139 | 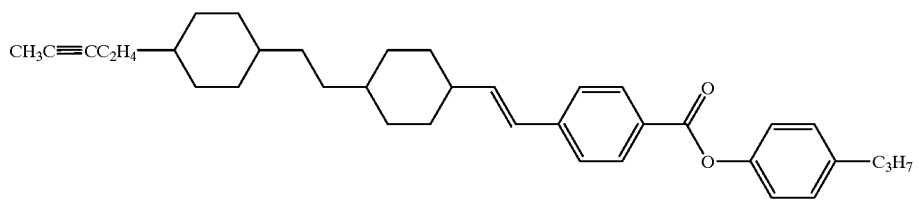 |
| 140 | 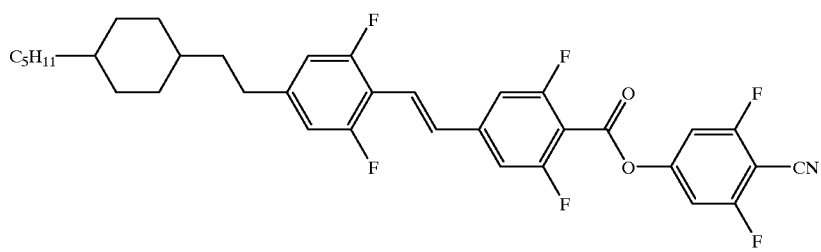 |
| 141 | 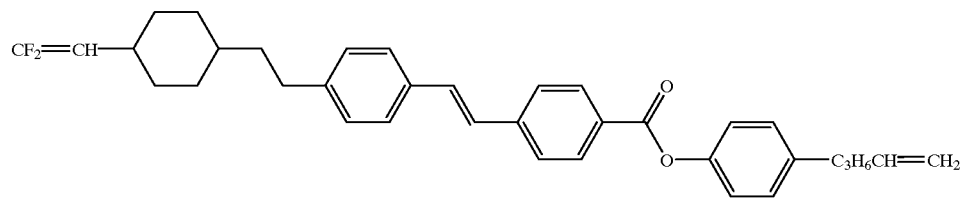 |

-continued

| No. | |
|---|---|
| 142 | 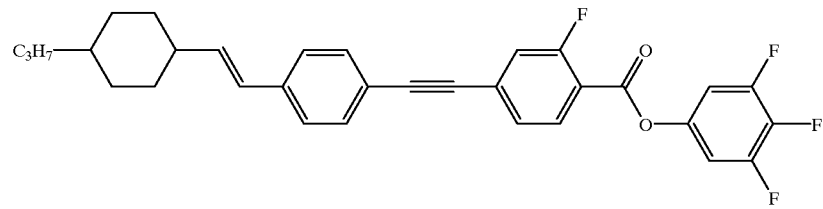 |
| 143 | 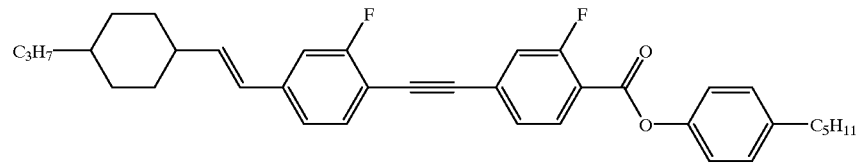 |
| 144 | 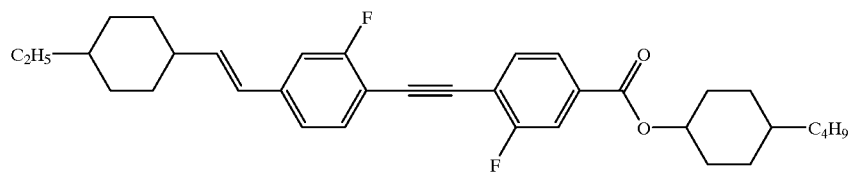 |
| 145 | 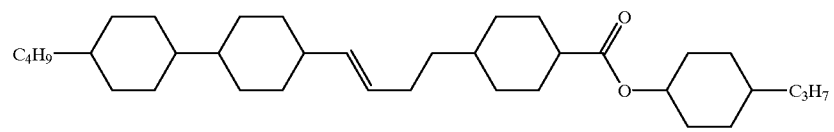 |
| 146 | 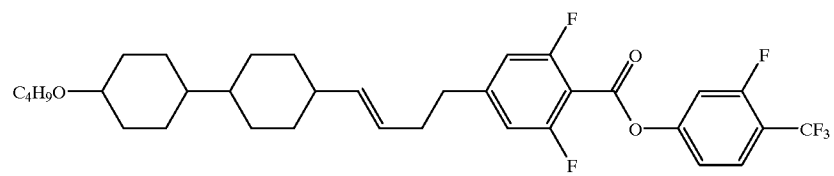 |
| 147 | 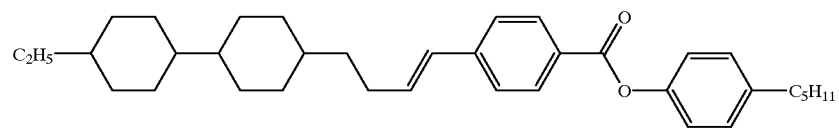 |
| 148 | 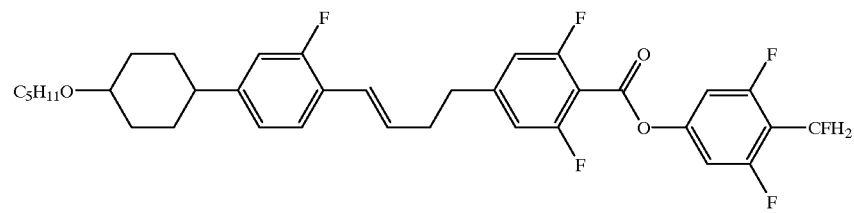 |
| 149 | 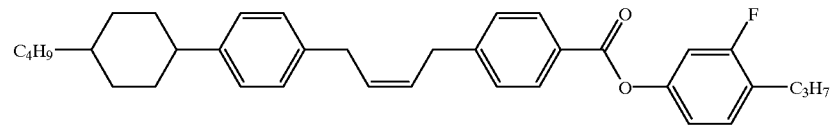 |

Example in which the liquid crystalline compounds of the present invention were used as component of liquid crystal compositions are shown below. In each of Use Examples, NI indicates a phase transition temperature of nematic phase-isotropic phase (° C.); $\Delta\epsilon$, dielectric anisotropy value; $\Delta n$, optical anisotropy value; $\eta$, viscosity at 20° C. (mPa·s); and $V_{10}$, threshold voltage (V).

EXAMPLE 5 (Use Example 1)

Liquid crystal composition ZLI-1132 (mother liquid crystal) produced by Merck and comprising the following cyanophenyl-cyclohexane type liquid crystalline compounds in the amount each shown below

| | |
|---|---|
| 4-(trans-4-propylcyclohexyl)benzonitrile | 24% by weight, |
| 4-(trans-4-pentylcyclohexyl)benzonitrile | 36% by weight, |
| 4-(trans-4-heptylcyclohexyl)benzonitrile and | 25% by weight, |
| 4-(trans-4-pentylcyclohexyl)-4'-cyanobiphenyl | 15% by weight | have the following physical properties:
NI: 72.4, $\Delta\epsilon$: 11.0, $\Delta n$: 0.137, $\eta$: 26.7, $V_{10}$ at a cell thickness of 9 $\mu$m: 1.78

To the mother liquid crystal (ZLI-1132) in an amount of 85% by weight was mixed 15% by weight of (E)-3,5-difluoro-4-cyanophenyl 4-(2-(trans-4-propylcyclohexyl)vinyl)benzoate (Compound No. 1) to prepare a liquid crystal composition. Physical properties of this liquid crystal composition were as follows:
NI: 86.5, $\Delta\epsilon$: 16.1, $\Delta n$: 0.217, $\eta$: 43.7, $V_{10}$ at a cell thickness of 8.8 $\mu$m: 1.42

While this liquid crystal composition was left in a freezer at −20° C., separation of crystals was not observed even after the lapse of 60 days.

EXAMPLE 6 (Use Example 2)

Example 5 was repeated to prepare a liquid crystal composition with the exception that (E)-3-fluoro-4-trifluoromethoxyphenyl trans-4-(2-(trans-4-pentylcyclohexyl)vinyl)cyclohexanecarboxylate (Compound No. 51) was used in place of (E)-3,5-difluoro-4-cyanophenyl 4-(2-(trans-4-propylcyclohexyl)vinyl)benzoate (Compound No. 1). Physical properties of this liquid crystal composition were as follows:
NI: 78.5, $\Delta\epsilon$: 10.4, $\Delta n$: 0.129, $\eta$: 28.1, $V_{10}$ at a cell thickness of 8.7 $\mu$m: 1.77

While this liquid crystal composition was left in a freezer at −20° C., separation of crystals was not observed even after the lapse of 60 days.

EXAMPLE 7 (Use Example 3)

Physical properties of the primary liquid crystal composition shown in Composition Example 17 were as follows:
NI: 100.6, $\Delta\epsilon$: 10.3, $\Delta n$: 0.170, $\eta$: 25.5, $V_{10}$: 1.36

To the primary liquid crystal composition described above in an amount of 100 parts by weight was added and dissolved 0.8 part of the optically active compound expressed by the formula (Op-4) described above to prepare a secondary liquid crystal composition, and the pitch (P) of the secondary liquid crystal composition was determined. The result was as follows:
P=10.5 $\mu$m

EXAMPLE 8 (Use Example 4)

Physical properties of the primary liquid crystal composition shown in Composition Example 18 were as follows:
NI: 98.4, $\Delta\epsilon$: 30.2, $\Delta n$: 0.152, $\eta$: 88.0, $V_{10}$: 0.99

EXAMPLE 9 (Use Example 5)

Physical properties of the primary liquid crystal composition shown in Composition Example 19 were as follows:
NI: 94.5, $\Delta\epsilon$: 6.3, $\Delta n$: 0.200, $\eta$: 36.1, $V_{10}$: 2.41

EXAMPLE 10 (Use Example 6)

Physical properties of the primary liquid crystal composition shown in Composition Example 20 were as follows:
NI: 66.9, $\Delta\epsilon$: 11.9, $\Delta n$: 0.118, $\eta$: 40.6, $V_{10}$: 0.97

EXAMPLE 11 (Use Example 7)

Physical properties of the primary liquid crystal composition shown in Composition Example 21 were as follows:
NI: 81.0, $\Delta\epsilon$: 9.2, $\Delta n$: 0.142, $\eta$: 20.7, $V_{10}$: 1.42

EXAMPLE 12 (Use Example 8)

Physical properties of the primary liquid crystal composition shown in Composition Example 22 were as follows:
NI: 104.6, $\Delta\epsilon$: 25.1, $\Delta n$: 0.128, $\eta$: 39.2, $V_{10}$: 0.82

EXAMPLE 13 (Use Example 9)

Physical properties of the primary liquid crystal composition shown in Composition Example 23 were as follows:
NI: 92.4, $\Delta\epsilon$: 27.9, $\Delta n$: 0.142, $\eta$: 40.7, $V_{10}$: 1.21

EXAMPLE 14 (Use Example 10)

Physical properties of the primary liquid crystal composition shown in Composition Example 24 were as follows:
NI: 69.1, $\Delta\epsilon$: 13.7, $\Delta n$: 0.119, $\eta$: 35.7, $V_{10}$: 0.86

EXAMPLE 15 (Use Example 11)

Physical properties of the primary liquid crystal composition shown in Composition Example 25 were as follows:
NI: 68.4, $\Delta\epsilon$: 6.2, $\Delta n$: 0.157, $\eta$: 20.2, $V_{10}$: 1.89

EXAMPLE 16 (Use Example 12)

Physical properties of the primary liquid crystal composition shown in Composition Example 26 were as follows:
NI: 103.2, $\Delta\epsilon$: 4.6, $\Delta n$: 0.100, $\eta$: 19.6, $V_{10}$: 2.54

EXAMPLE 17 (Use Example 13)

Physical properties of the primary liquid crystal composition shown in Composition Example 27 were as follows:
NI: 110.4, $\Delta\epsilon$: 9.7, $\Delta n$: 0.099, $\eta$: 34.8, $V_{10}$: 1.15

To the primary liquid crystal composition described above in an amount of 100 parts by weight was added and dissolved 0.3 part of the optically active compound expressed by the formula (Op-8) described above to prepare a secondary liquid crystal composition, and the pitch (P) of the secondary liquid crystal composition was determined. The result was as follows:
P=77.6 $\mu$m

EXAMPLE 18 (Use Example 14)

Physical properties of the primary liquid crystal composition shown in Composition Example 28 were as follows:
NI: 94.6, $\Delta\epsilon$: 11.3, $\Delta n$: 0.122, 17: 37.2, $V_{10}$: 0.81

EXAMPLE 19 (Use Example 15)

Physical properties of the primary liquid crystal composition shown in Composition Example 29 were as follows:
NI: 96.4, $\Delta\epsilon$: 7.4, $\Delta n$: 0.133, $\eta$: 26.0, $V_{10}$: 1.62

EXAMPLE 20 (Use Example 16)

Physical properties of the primary liquid crystal composition shown in Composition Example 30 were as follows:

NI: 99.6, Δε: 9.3, Δn: 0.117, η: 36.2, $V_{10}$: 1.59

EXAMPLE 21 (Use Example 17)

Physical properties of the primary liquid crystal composition shown in Composition Example 31 were as follows:

NI: 88.2, Δε: 9.6, Δn: 0.096, η: 21.5, $V_{10}$: 1.05

EXAMPLE 22 (Use Example 18)

Physical properties of the primary liquid crystal composition shown in Composition Example 32 were as follows:

NI: 101.7, Δε: 8.5, Δn: 0.133, η: 17.6, $V_{10}$: 2.06

EXAMPLE 23 (Use Example 19)

Physical properties of the primary liquid crystal composition shown in Composition Example 33 were as follows:

NI: 85.8, Δε: 10.8, Δn: 0.094, η: 31.6, $V_{10}$: 1.94

While primary liquid crystal compositions shown in Examples 7 through 23 were left in separate freezers at −20° C., respectively, development of smectic phase or separation of crystals was not observed after the lapse of 60 days with any of the primary liquid crystal compositions.

COMPARATIVE EXAMPLE 1

Example 6 was repeated with the exception that the compound containing no alkenylene group and expressed by the formula (d)

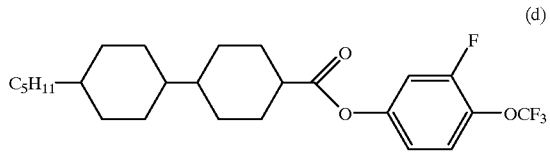

was used in place of (E)-3-fluoro-4-trifluoromethoxyphenyl trans-4-(2-(trans-4-pentylcyclohexyl)vinyl)cyclohexanecarboxylate (Compound No. 51), to obtain a liquid crystal composition. Physical properties of this liquid crystal composition were as follows:

Δε: 10.5, η: 28.8, $V_{10}$ at a cell thickness of 8.7 μm: 1.78

From the comparison of these physical properties with those shown in Example 6, it can be understood that the compound (Compound No. 51) (comprising alkenylene group) of the present invention has a lower viscosity than the compound comprising no alkenylene group and expressed by the formula (d), and that the compound of the present invention has a lower threshold voltage ($V_{10}$) than the compound of the formula (d) whereas the former has a lower Δε than the latter. These results are contrary to the ones expected based on technical common sense (reference is made to the Reference Example described below), and thus those results were unable to anticipate.

REFERENCE EXAMPLE

Liquid crystal composition ZLI-1083 (base mixture) produced by Merck and comprising the following cyanophenyl-cyclohexane type liquid crystalline compounds in the amount each shown below

| | |
|---|---|
| 4-(trans-4-propylcyclohexyl)benzonitrile | 30% by weight, |
| 4-(trans-4-pentylcyclohexyl)benzonitrile and | 40% by weight, |
| 4-(trans-4-heptylcyclohexyl)benzonitrile | 30% by weight, | have the following physical properties:

NI: 52.3, Δε: 10.7, Δn: 0.119, η: 21.7, $V_{10}$ at a cell thickness of 9 μm: 1.60

To compositions each consisting of the base mixture (ZLI-1083) in an amount of 85% by weight was mixed 15% by weight of either compound expressed by the formula (e) or (f)

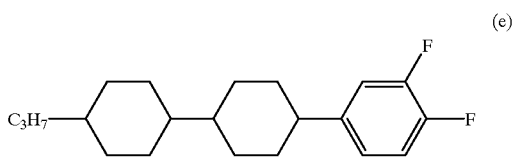

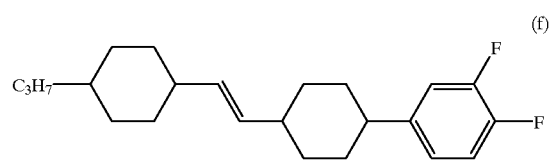

as known reference compound, to prepare two final liquid crystal compositions. Physical properties of the final liquid crystal compositions obtained were as follows:

| | η | Δε | $V_{10}$ |
|---|---|---|---|
| Compound expressed by the formula (e) | 21.2 | 10.4 | 1.59 |
| Compound expressed by the formula (f) | 23.3 | 10.6 | 1.82 |

As will clearly be seen from the results shown above, compounds in which alkenylene group is introduced between six-membered rings (cf. compound expressed by the formula (f)) have a higher viscosity and a higher threshold voltage ($V_{10}$) compared with the compounds in which alkenylene group is not introduced (cf. compound expressed by the formula (e)).

INDUSTRIAL APPLICABILITY

As described above, the compounds of the present invention are wide in temperature range of liquid crystal phase, are low in viscosity, have a low threshold voltage, are excellent in stability, are readily mixed with various liquid crystal materials, and are excellent in solubility even at low temperatures.

Accordingly, when the compounds of the present invention are used as component of liquid crystal compositions, liquid crystal compositions having the characteristics described above can be produced, and besides, liquid crystal compositions having desired physical properties can be provided by selecting proper rings, substituents and/or bonding groups as molecule constituting element of the compounds.

We claim:
1. A vinylene compound expressed by the general formula (1)

$$Ra-A_1-Z_1-A_2-Z_2-A_3-(Z_3-A_4)_m-Rb \quad (1)$$

wherein Ra represents an alkyl group having 1 to 20 carbon atoms one or more —$CH_2$— in which alkyl group may be replaced by —O—, —S—, —CO—, —CH=CH—, or —C≡C—, but in no case —O— and/or —S— continues, and one or more hydrogen atoms in which alkyl group may be replaced by a halogen atom; Rb represents Ra, a halogen atom, or cyano group; $A_1$, $A_2$, $A_3$, and $A_4$ independently represent trans-1,4-cyclohexylene group, cyclohexenylene group, 1,4-phenylene group one or more hydrogen atoms on which ring may be replaced by a halogen atom or cyano group, pyridine-2,5-diyl group, pyrimidine-2,5-diyl group, or 1,3-dioxane-2,5-diyl group; and $Z_1$, $Z_2$, and $Z_3$ independently represent a vinylene group, —COO—, —OCO—, —$(CH_2)_2$—, —C≡C—, —$CH_2O$—, —$OCH_2$—, or a covalent bond provided that at least one of $Z_1$ to $Z_3$ is a vinylene group a ring pair holding the vinylene group therebetween is under the following condition, and at least one of $Z_1$ to $Z_3$ represents —COO— or —OCO—; and m is 0 or 1;

condition for the ring pair: at least one of the rings of the pair is selected from trans-1,4-cyclohexylene group, cyclohexenylene group, or 1,3-dioxane-2,5-diyl group.

2. The vinylene compound according to claim 1 wherein m is 0.
3. The vinylene compound according to claim 1 wherein m is 1.
4. The vinylene compound according to claim 2 wherein $Z_1$ is vinylene.
5. The vinylene compound according to claim 2 wherein $Z_2$ is vinylene.
6. The vinylene compound according to claim 3 wherein $Z_1$ is vinylene.
7. The vinylene compound according to claim 3 wherein $Z_2$ is vinylene.
8. The vinylene compound according to claim 4 wherein $A_1$ and $A_2$ are independently trans-1,4-cyclohexylene group, or 1,4-phenylene group one or more hydrogen atoms on which ring may be replaced by a halogen atom or cyano group.
9. The vinylene compound according to claim 6 wherein $A_1$ and $A_2$ are independently trans-1,4-cyclohexylene group, or 1,4-phenylene group one or more hydrogen atoms on which ring may be replaced by a halogen atom or cyano group.
10. The vinylene compound according to claim 5 wherein $A_1$ and $A_2$ are independently trans-1,4-cyclohexylene group, or 1,4-phenylene group one or more hydrogen atoms on which ring may be replaced by a halogen atom or cyano group.
11. The vinylene compound according to claim 7 wherein $A_1$ and $A_2$ are independently trans-1,4-cyclohexylene group, or 1,4-phenylene group one or more hydrogen atoms on which ring may be replaced by a halogen atom or cyano group.
12. A liquid crystal composition comprising at least two components, at least one of which is a vinylene compound defined in any one of claims 1 to 9, 10 or 11.
13. A liquid crystal composition comprising, as a first component, at least one vinylene compound defined in any one of claims 1 to 9, 10 11 and comprising, as a second component, at least one compound selected from the group consisting of the compounds expressed by any one of the general formulas (2), (3), and (4)

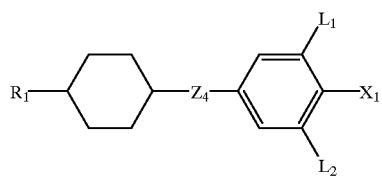

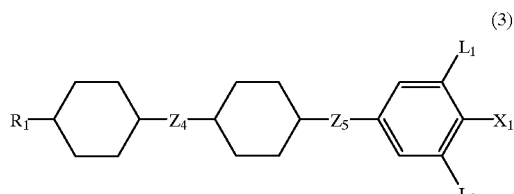

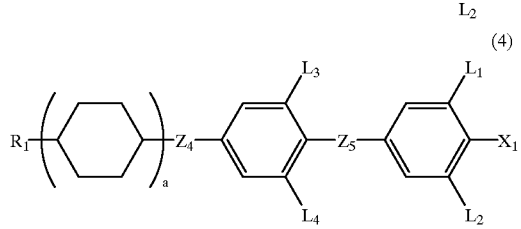

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent —$(CH_2)_2$—, —CH=CH—, or a covalent bond; and a is 1 or 2.

14. A liquid crystal composition comprising, as a first component, at least one vinylene compound defined in any one of claims 1 to 9, 10 or 11 and comprising, as a second component, at least one compound selected from the group consisting of the compounds expressed by any one of the general formulas (5), (6), (7), (8), and (9)

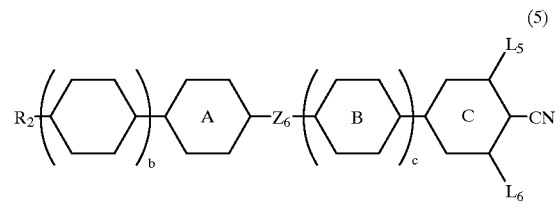

wherein $R_2$ represents F, an alkyl group having 1 to 10 carbon atoms, or an alkenyl group having 2 to 10 carbon atoms any methylene group (—$CH_2$—) in which alkyl or alkenyl group may be replaced by oxygen atom (—O—), but in no case two or more methylene groups are continuously replaced by oxygen atom; ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —$(CH_2)_2$—, —COO—, or a covalent bond; $L_5$ and $L_6$ independently represent H or F; and b and c are independently 0 or 1, (6)

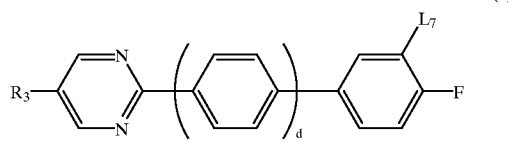

wherein $R_3$ represents an alkyl group having 1 to 10 carbon atoms, $L_7$ represents H or F; and d is 0 or 1, (7)

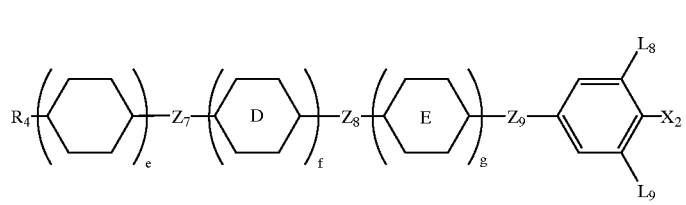

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or a covalent bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$; and e, f, and g are independently 0 or 1, (8)

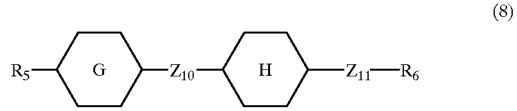

wherein $R_5$ and $R_6$ independently represent an alkyl group having 1 to 10 carbon atoms or an alkenyl group having 2 to 10 carbon atoms any methylene group (—$CH_2$—) in which alkyl or alkenyl group may be replaced by oxygen atom (—O—), but in no case two or more methylene groups are continuously replaced by oxygen atom; ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents —C≡C—, —COO—, —$(CH_2)_2$—, —CH=CH—C≡C—, or a covalent bond; and $Z_{11}$ represents —COO— or a covalent bond, wherein $R_7$ and $R_8$ independently represent an alkyl group having 1 to 10 carbon atoms or an alkenyl group having 2 to 10 carbon atoms any methylene group (—$CH_2$—) in which alkyl or alkenyl group may be replaced by oxygen atom (—O—), but in no case two or more methylene group are continuously replaced by oxygen atom; ring I represents trans-1,4-cyclohexylene group, 1,4-phenylene group, or pyrimidine-2,5-diyl group; ring J represents trans-1,4-cyclohexylene group, 1,4-phenylene group one or more hydrogen atoms on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —$(CH_2)_2$—, or a covalent bond; $Z_{13}$ represents —CH=CH—, —C≡C—, —COO—, or a covalent bond; and h is 0 or 1.

15. A liquid crystal display device comprising the liquid crystal composition defined in claim 12.

16. A liquid crystal display device comprising the liquid crystal composition defined in claim 13.

17. A liquid crystal display device comprising the liquid crystal composition defined in claim 14.

18. A liquid crystal composition comprising, as a first component, at least one vinylene compound defined in any one of claims 1 to 9, 10 or 11, comprising, as a part of a second component, at least one compound selected from the group consisting of the compounds expressed by any one of the general formulas (2), (3), and (4), and comprising, as another part of the second component, at least one compound selected from the group consisting of the compounds expressed by any one of the general formulas (5), (6), (7), (8), and (9)

(2)

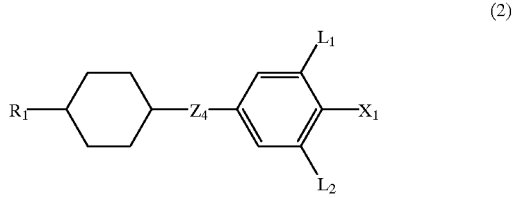

(9)

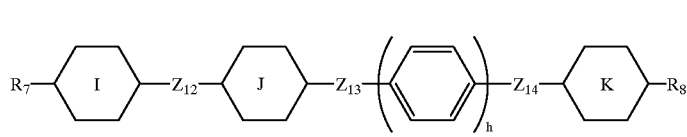

(3)

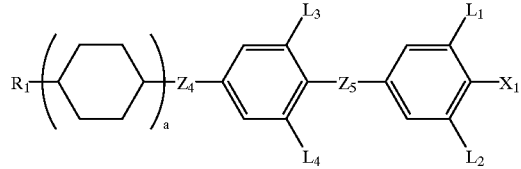

(4)

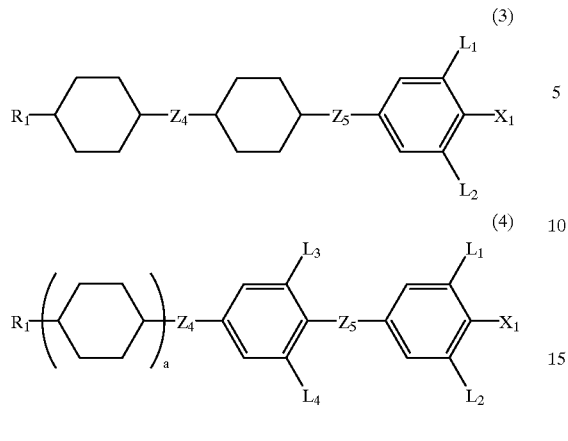

wherein $R_1$ represents an alkyl group having 1 to 10 carbon atoms; $X_1$ represents F, Cl, $OCF_3$, $OCF_2H$, $CF_3$, $CF_2H$, or $CFH_2$; $L_1$, $L_2$, $L_3$, and $L_4$ independently represent H or F; $Z_4$ and $Z_5$ independently represent —$(CH_2)_2$—, —CH=CH—, or a covalent bond; and a is 1 or 2, (5)

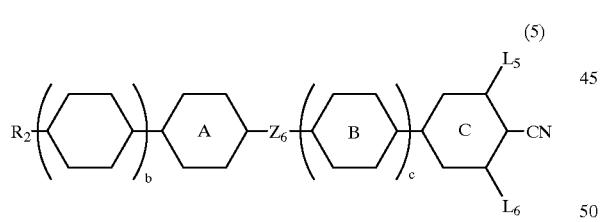

wherein $R_2$ represents F, an alkyl group having 1 to 10 carbon atoms, or an alkenyl group having 2 to 10 carbon atoms any methylene group (—$CH_2$—) in which alkyl or alkenyl group may be replaced by oxygen atom (—O—), but in no case two or more methylene groups are continuously replaced by oxygen atom; ring A represents trans-1,4-cyclohexylene group, 1,4-phenylene group, or 1,3-dioxane-2,5-diyl group; ring B represents trans-1,4-cyclohexylene group, 1,4-phenylene group, or pyrimidine-2,5-diyl group; ring C represents trans-1,4-cyclohexylene group or 1,4-phenylene group; $Z_6$ represents —$(CH_2)_2$—, —COO—, or a covalent bond; $L_5$ and $L_6$ independently represent H or F; and b and c are independently 0 or 1, (6)

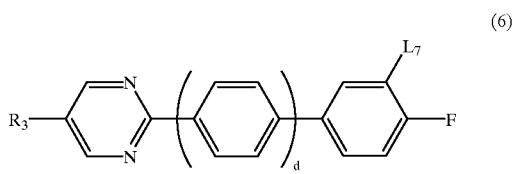

wherein $R_3$ represents an alkyl group having 1 to 10 carbon atoms, $L_7$ represents H or F; and d is 0 or 1, (7)

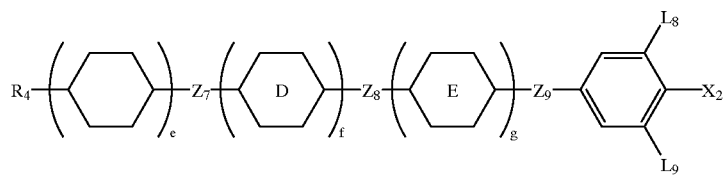

wherein $R_4$ represents an alkyl group having 1 to 10 carbon atoms; ring D and ring E independently represent trans-1,4-cyclohexylene group or 1,4-phenylene group; $Z_7$ and $Z_8$ independently represent —COO— or a covalent bond; $Z_9$ represents —COO— or —C≡C—; $L_8$ and $L_9$ independently represent H or F; $X_2$ represents F, $OCF_3$, $OCF_2H$, $CF_3$, $CF_2H$, or $CFH_2$; and e, f, and g are independently 0 or 1, (8)

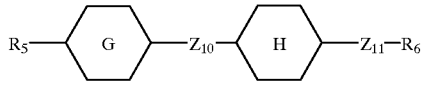

wherein $R_5$ and $R_6$ independently represent an alkyl group having 1 to 10 carbon atoms or an alkenyl group having 2 to 10 carbon atoms any methylene group (—$CH_2$—) in which alkyl or alkenyl group may be replaced by oxygen atom (—O—), but in no case two or more methylene groups are continuously replaced by oxygen atom; ring G represents trans-1,4-cyclohexylene group, 1,4-phenylene group, or pyrimidine-2,5-diyl group; ring H represents trans-1,4-cyclohexylene group or 1,4-phenylene group; $Z_{10}$ represents —C≡C—, —COO—, —$(CH_2)_2$—, —CH=C—H—C≡C—, or a covalent bond; and $Z_{11}$ represents —COO— or a covalent bond,

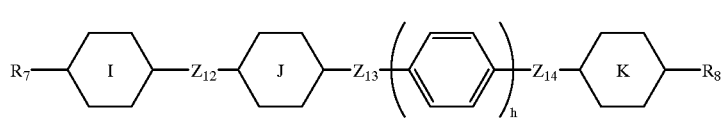

(9)

wherein $R_7$ and $R_8$ independently represent an alkyl group having 1 to 10 carbon atoms or an alkenyl group having 2 to 10 carbon atoms any methylene group (—$CH_2$—) in which alkyl or alkenyl group may be replaced by oxygen atom (—O—), but in no case two or more methylene group are continuously replaced by oxygen atom; ring I represents trans-1,4-cyclohexylene group, 1,4-phenylene group, or pyrimidine-2,5-diyl group; ring J represents trans-1,4-cyclohexylene group, 1,4-phenylene group one or more hydrogen atoms on which ring may be replaced by F, or pyrimidine-2,5-diyl group; ring K represents trans-1,4-cyclohexylene group or 1,4-phenylene group; $Z_{12}$ and $Z_{14}$ independently represent —COO—, —$(CH_2)_2$—, or a covalent bond; $Z_{13}$ represents —CH=CH—, —C≡C—, —COO—, or a covalent bond; and h is 0 or 1.

19. A liquid crystal display device comprising the liquid crystal composition defined in claim 18.

* * * * *